(12) United States Patent
Gavaris et al.

(10) Patent No.: US 11,650,154 B2
(45) Date of Patent: May 16, 2023

(54) SYSTEMS AND METHODS FOR DETERMINING SAMPLE OSMOLARITY

(71) Applicant: LACRISCIENCES, LLC, Washington, DC (US)

(72) Inventors: Paul T. Gavaris, Washington, DC (US); Chris D. Geddes, Bel Air, MD (US); Ali H. Ghovanlou, Potomac, MD (US)

(73) Assignee: LACRISCIENCES, LLC, Washington, DC (US)

( * ) Notice: Subject to any disclaimer, the term of this patent is extended or adjusted under 35 U.S.C. 154(b) by 181 days.

(21) Appl. No.: 17/245,748

(22) Filed: Apr. 30, 2021

(65) Prior Publication Data

US 2021/0247311 A1     Aug. 12, 2021

Related U.S. Application Data

(63) Continuation of application No. 16/820,435, filed on Mar. 16, 2020, now Pat. No. 11,016,025, which is a
(Continued)

(51) Int. Cl.
*G01N 21/552* (2014.01)
*G01N 33/48* (2006.01)
(Continued)

(52) U.S. Cl.
CPC .......... *G01N 21/554* (2013.01); *A61B 3/101* (2013.01); *A61B 5/1455* (2013.01);
(Continued)

(58) Field of Classification Search
CPC .... G01N 21/554; G01N 21/553; G01N 33/84; G01N 2800/16; A61B 3/101; A61B 5/1455
See application file for complete search history.

(56) References Cited

U.S. PATENT DOCUMENTS 5,923,031 A   7/1999 Naya
6,139,797 A   10/2000 Suzuki et al.
(Continued)

FOREIGN PATENT DOCUMENTS

CN   102253014 A   11/2011
CN   102692397     2/2015
(Continued)

OTHER PUBLICATIONS

Robelek et al., "Label-free and time-resolved measurements of cell volume changes by surface plasmon resonance (SPR) spectroscopy," (2010) Biosensors and Bioelectronics 25(5):1221-1224.
(Continued)

*Primary Examiner* — Jamil Ahmed
(74) *Attorney, Agent, or Firm* — Haynes and Boone LLP

(57) ABSTRACT

Systems and methods for determining the osmolarity of a sample are provided. Aspects of the subject methods include contacting a sensing surface of a surface plasmon resonance based sensor with a sample, and generating one or more data sets at at least two wavelengths over a time interval, wherein the data sets are used to determine the osmolarity of the sample. The subject methods find use in determining the osmolarity of a sample, such as a biological sample (e.g., a tear fluid), and in the diagnosis and/or monitoring of various diseases and disorders, such as, e.g., dry eye disease.

20 Claims, 61 Drawing Sheets

Panel A

The Surface Plasmon Resonance Technique for Tear Osmolarity Measurement

Panel B

Typical SPR Image

The angular location of the central minima of the SPR curve is proportional to the refractive index of the tear fluid in contact with the gold sensing surface.

Related U.S. Application Data continuation of application No. 15/774,580, filed as application No. PCT/US2016/061424 on Nov. 10, 2016, now Pat. No. 10,591,414.

(60) Provisional application No. 62/253,595, filed on Nov. 10, 2015.

(51) Int. Cl.
*A61B 3/10* (2006.01)
*G01N 33/84* (2006.01)
*A61B 5/1455* (2006.01)

(52) U.S. Cl.
CPC ........... *G01N 21/553* (2013.01); *G01N 33/84* (2013.01); *G01N 2800/16* (2013.01)

(56) References Cited

U.S. PATENT DOCUMENTS

| | | |
|---|---|---|
| 6,326,612 B1 | 12/2001 | Elkind et al. |
| 6,415,235 B1 | 7/2002 | Bartholomew et al. |
| 7,149,868 B2 | 12/2006 | Codner et al. |
| 7,395,103 B2 | 7/2008 | Cappo et al. |
| 7,675,624 B2 | 3/2010 | Chinowsky et al. |
| 8,249,682 B2 | 8/2012 | Cappo et al. |
| 2001/0040130 A1 | 11/2001 | Lorch et al. |
| 2002/141060 A1 | 10/2002 | Lu et al. |
| 2003/0059342 A1 | 3/2003 | Elkind |
| 2003/0103208 A1 | 6/2003 | Quinn et al. |
| 2004/0017572 A1 | 1/2004 | Anafi et al. |
| 2004/0086872 A1 | 5/2004 | Childers et al. |
| 2004/0100634 A1 | 5/2004 | Bartholomew et al. |
| 2004/0135272 A1 | 7/2004 | Lu et al. |
| 2004/0263854 A1 | 12/2004 | Anafie et al. |
| 2005/0046854 A1 | 3/2005 | Kunuki et al. |
| 2005/0159657 A1 | 7/2005 | Cappo et al. |
| 2005/0200852 A1 | 9/2005 | Kimura |
| 2005/0200853 A1 | 9/2005 | Mori et al. |
| 2006/0012795 A1 | 1/2006 | Niemax et al. |
| 2006/0127278 A1 | 6/2006 | Gast et al. |
| 2006/0188401 A1 | 8/2006 | Robotti et al. |
| 2007/0109541 A1 | 5/2007 | Imato et al. |
| 2008/0030737 A1 | 2/2008 | Su et al. |
| 2009/0005660 A1 | 1/2009 | Cappo et al. |
| 2009/0323073 A1 | 12/2009 | Luber et al. |
| 2010/0128269 A1 | 5/2010 | Chinowsky et al. |
| 2010/0267163 A1 | 10/2010 | Ran et al. |
| 2010/0285612 A1 | 11/2010 | Iwasaki et al. |
| 2011/0188043 A1 | 8/2011 | Davidov et al. |
| 2011/0211189 A1 | 9/2011 | Ryan et al. |
| 2013/0344623 A1 | 12/2013 | Ran et al. |
| 2014/0185051 A1 | 7/2014 | Guan et al. |
| 2015/0109614 A1* | 4/2015 | De Oliveira Garcia Da Fonseca ............... G01N 33/553 356/128 |
| 2015/0146180 A1 | 5/2015 | Lee et al. |
| 2015/0247797 A1 | 9/2015 | Oberg |
| 2015/0300954 A1 | 10/2015 | Chan et al. |
| 2016/0313246 A1 | 10/2016 | Wong et al. |
| 2018/0321150 A1 | 11/2018 | Gavaris et al. |

FOREIGN PATENT DOCUMENTS

| | | |
|---|---|---|
| JP | 55-31963 | 3/1980 |
| JP | H01-026347 | 9/1990 |
| JP | H10-267841 | 10/1998 |
| JP | H11183372 A | 7/1999 |
| JP | H11326194 | 11/1999 |
| JP | 2002323446 | 11/2002 |
| JP | 2002214134 A | 12/2002 |
| JP | 2003075334 | 3/2003 |
| JP | 2004053372 A | 2/2004 |
| JP | 2005077317 | 3/2005 |
| JP | 2006078364 | 3/2006 |
| JP | 2007170866 | 7/2007 |
| JP | 2007225389 | 9/2007 |
| JP | 2007527278 | 9/2007 |
| JP | 2007333612 | 12/2007 |
| JP | 2009-236709 | 10/2009 |
| JP | 2012181024 | 9/2012 |
| JP | 2012523576 | 10/2012 |
| JP | 2013512435 | 4/2013 |
| WO | 2001088525 A1 | 11/2001 |
| WO | 2005/067651 | 7/2005 |
| WO | 2014189067 | 11/2014 |

OTHER PUBLICATIONS

PCT/US2016/036834, International Preliminary Report on Patentability, dated Dec. 21, 2017.

PCT/US2016/036834, International Search Report dated Sep. 28, 2016.

Kim et al., "Novel Miniature SPR Immunosensor Equipped with All-in-one Multi-microchannel Sensor Chip for Detecting Low-molecular-weight Analytes," (2007) Biosensor and Bioelectronics 23(5):701-707.

* cited by examiner

| Capture Number | Pixel 1948 Y₁ Value | Pixel 1949 Y₂ Value | -Y₂/Y₁ | Zero Crossing |
|---|---|---|---|---|
| 1 | -0.0333 | 0.0065 | 0.1964 | 1948.8358 |
| 2 | -0.0299 | 0.0075 | 0.2505 | 1948.7997 |
| 3 | -0.0401 | 0.0030 | 0.0746 | 1948.9306 |
| 4 | -0.0287 | 0.0145 | 0.5051 | 1948.6644 |
| 5 | -0.0360 | 0.0087 | 0.2413 | 1948.8056 |
| 6 | -0.0296 | 0.0135 | 0.4552 | 1948.6872 |
| 7 | -0.0346 | 0.0077 | 0.2238 | 1948.8171 |
| 8 | -0.0358 | 0.0064 | 0.1802 | 1948.8473 |
| 9 | -0.0316 | 0.0151 | 0.4788 | 1948.6762 |
| 10 | -0.0358 | 0.0103 | 0.2886 | 1948.7760 |
| Average | -0.0335 | 0.0093 | Average | 1948.7840 |
|  |  |  | Minimum | 1948.6644 |
|  |  |  | Maximum | 1948.9306 |
|  |  |  | Delta | 0.2662 |
|  |  |  | Std. Dev. | 0.0852 |

The index of refraction uncertainty is $3.113 \times 10^{-5} \times \pm 0.1331 = \pm 4.143 \times 10^{-6}$ RIU The corresponding osmolarity range is $\pm 4.14 \times 10^{-6} / 2.42 \times 10^{-5} = \pm 0.171$ mOsm

FIG. 13

SPR line

The solution of $ax^2+bx+c=0$ is:

$$x = \frac{-b \pm \sqrt{b^2 - 4ac}}{2a}$$

---

The solution of $ax^3+bx^2+cx+d=0$ is:

$$x = \{q + [q^2 + (r-p^2)^3]^{1/2}\}^{1/3} + \{q - [q^2 + (r-p^2)^3]^{1/2}\}^{1/3} + p$$

where $$p = -b/(3a), \quad q = p^3 + (bc-3ad)/(6a^2), \quad r = c/(3a)$$

FIG. 20

Snell's Law

$n_1 \sin \theta_I = n_2 \sin \theta_T$

Total internal reflection occurs when $\theta_T > 90°$, and the critical angle $\theta_C$ occurs when $\theta_T = 90°$. In this case:

$n_1 \sin \theta_C = n_2$

Rearranging terms yields the equation for the critical angle $\theta_C$:

$\theta_C = \sin^{-1}(n_2/n_1)$

SYSTEMS AND METHODS FOR DETERMINING SAMPLE OSMOLARITY

CROSS REFERENCE TO RELATED APPLICATIONS

This application claims priority benefit of the filing date of U.S. Provisional Patent Application Ser. No. 62/253,595, filed on Nov. 10, 2015, the disclosure of which application is herein incorporated by reference in its entirety.

FIELD OF THE INVENTION

The present invention relates to systems and methods for determining the osmolarity of a sample, such as a biological sample (e.g., a tear fluid).

BACKGROUND OF THE INVENTION

Dry eye disease, or Keratoconjunctivitis Sicca (KCS) is one of the most frequently established diagnoses in ophthalmology. Current estimates hold that roughly 40-60 million people in the United States exhibit dry eye symptoms. The lack of accurate statistical data about the occurrence of dry eye is due largely to a lack of state-of-the-art diagnostic equipment. A more disturbing trend, however, is the misdiagnosis of dry eye or its escape from early detection altogether, since symptomatic patients are not always easily identified.

Pursuing more effective diagnosis will strengthen the paradigm of ophthalmic care, a fact recognized by the pharmaceutical industry. The first prescription pharmaceuticals for treating dry eye are now appearing on the market, with more on the way, and yet the methods for diagnosis and monitoring treatment remain problematic.

There is no "gold standard" test that both diagnoses dry eye and monitors the effectiveness of treatment efforts. One popular method is a matrix of subjective observation of symptoms and objective tests (such as Schirmer testing, staining techniques and tear break-up time), none of which is specific to the detection of dry eye or the measurement of its severity. Considering recent pharmaceutical advancements aimed at treating dry eye, timely and parallel advancements in diagnostic technologies are needed.

The osmolarity of a tear—the degree of dissolved solids therein—is popularly accepted by experts in the field as an indicator of the presence and severity of dry eye. The instrument most commonly associated with the measurement of tear osmolarity is the osmometer; however, technical limitations have restricted the use of tear osmometers to primarily research environments.

An osmometer is a device that measures the concentration of dissolved solutes in a liquid, such as water. Though it is widely used in other fields, osmometers are used in medicine in applications such as determining osmol gap in toxicology and trauma cases, monitoring mannitol treatment infusions, and monitoring the absorption in glycine ingestion with irrigation fluids in surgical procedures, among others.

Despite the suitability of this technology for measuring tear osmolarity, current devices present certain limitations that prevent their widespread use in a clinical environment. The most prevalent problem has to do with sample size. Nearly all commercially available osmometers are designed (and perhaps technologically limited) to measure milliliter-size samples. Tear samples extracted from patients tend to be in the nanoliter volumes, and further complicating matters, dry eye patients generally have fewer tears, making handling of samples even more difficult. Osmometers designed to measure nanoliter sample sizes are not available commercially and are too cumbersome for practical use in a clinical environment. The result is that practicing ophthalmologists are left with a haphazard methodology and inadequate tools to accurately detect this prevalent condition.

Dry eye disease is a complex group of diseases characterized by a decreased production of one or more of the three components of the tear film: the lipid layer, the aqueous layer, and the mucin layer. A deficiency in one of the tear film components may lead to a loss of the tear film stability. Normal sight relies on a moist ocular surface and requires a sufficient quality of tears, normal composition of the tear film, regular blinking and normal lid closure as prerequisites. If left untreated, dry eye syndrome can cause progressive pathological changes in the conjunctival and corneal epithelium, discomfort, corneal ulceration's and even ultimately lead to blindness.

Standard treatment has been tear replacement therapy, which attempts to either mimic the human tear film or present a more sophisticated hypo-osmolar version of the tear film. Unfortunately, as dry eye syndrome progresses beyond the mild stage, this common therapy becomes less effective. Further, these treatments do not address the etiology of dry eye.

The precise mechanisms that give rise to dry eye are currently unknown and have been the subject of debate over the years. Recently, several different mechanisms have been proposed as a possible etiology of dry eye, with a general ideology that it is usually caused by a problem with the quality of the tear film that lubricates the ocular surface. More recent research has proposed that dry eye may be a result of a decrease in hormonal status with aging (being more prominent in postmenopausal women), or have an immune basis and acquired inflammatory condition of the ocular surface. Other causes of dry eye symptoms can occur from certain medications (e.g., antihistamines, beta-blockers), associations with certain systemic inflammatory diseases (e.g., rheumatoid arthritis), mechanical causes (e.g., incomplete closure of eyelids), infectious causes (e.g., viral infections) and certain neurological causes (e.g., LASIK procedures). Despite recent gains in knowledge of possible pathogenic factors of dry eye, there has been a lack of consensus as to the appropriate diagnostic criteria, the specific aims of objective diagnostic testing, the role subjective symptoms play in diagnosis, and the interpretation of results.

The symptoms of dry eye vary considerably from one individual to another. Most patients complain of a foreign body sensation, burning and general ocular discomfort. The discomfort is typically described as a scratchy, dry, sore, gritty, smarting or burning feeling. Discomfort is the hallmark of dry eye because the cornea is richly supplied with sensory nerve fibers.

Despite its high prevalence, dry eye is not always easy to diagnose. The vast majority of patients have symptoms that are mild to moderate in severity. Although these patients are genuinely suffering discomfort, objective signs of dry eye may be missed, and without proper diagnosis, patients may not receive the attention and treatment that this condition warrants. The signs and symptoms of dry eye can be misinterpreted as evidence of other conditions, such as infectious, allergic, or irritative conjunctivitis. Given these complications in diagnosis, it is estimated that the diagnosis rate of dry eye is approximately 20%.

Diagnosis of dry eye typically begins with clinical examination. A Schrimer test is usually performed where standardized strips of filter paper are placed at the junction between the middle and lateral third of the lower lid. If less than 5 millimeters has been wetted after 5 minutes, there is reason to believe aqueous tear deficiency is present. Though the test is quick, inexpensive and results are available immediately, it provides only a rough estimate and is unreliable in moderate dry eye.

Dye staining is another method of diagnosing dry eye, with either fluorescein or Rose Bengal, and a trained physician can look for patterns under slit lamp observation indicating dryness. Another test, tear break-up time, is a measure of the stability of the tear film. A normal tear film begins to break up after approximately 10 seconds, and this time is reduced in patients with dry eye.

The osmometer generally used in measuring tear osmolarity is the Clifton Direct Reading Nanoliter Osmometer (Clifton Technical Physics, Hartford, N.Y.) developed in the 1960's. Although not necessarily originally intended for use in measuring tears, it is one of the few instruments capable of measuring nanoliter volumes of solution and has found its way into ophthalmology.

The Clifton Osmometer was produced in limited quantities over the years, and is not routinely used outside a research laboratory. It is based on the well-known measurement technique called freezing point depression. The Clifton Osmometer measures the osmolarity of a sample by measuring the freezing point depression. In freezing point depression measurements, water (which normally freezes at 0° C.), experiences a depression in its freezing temperature in presence of dissolved solutes, the mathematical relationship of which is defined by Raoult's Law.

Though the test can be accurate, it requires a very skilled operator to make the measurement. The test monitors the depression in freezing temperature by examining a fractional volume of a teardrop under a microscope. Due to its limitations and lack of availability, there appears to be only a few units left in the field. Furthermore each measurement can take over fifteen minutes, which, coupled with the small sample volumes, make the use of the Clifton Osmometer an extremely tedious and inconvenient process. The amount of time required and the operating skill demanded are unacceptable to a busy practice or clinic, even if the units were available.

There is a need for simple and accurate sensors, systems and methods that can determine the osmolarity of a sample, such as, e.g., a biological sample, e.g., a tear fluid, and to use the osmolarity data to diagnose and/or monitor treatment efforts for various diseases and disorders, such as, e.g., dry eye disease.

SUMMARY

Systems and methods for determining the osmolarity of a sample are provided. Aspects of the subject methods include contacting a sensing surface of a sensor with a sample, and generating one or more data sets over a time interval, wherein the data sets are used to determine the osmolarity of the sample. The subject methods find use in determining the osmolarity of a sample, such as a biological sample (e.g., a tear fluid), and in the diagnosis and/or monitoring of various diseases and disorders, such as, e.g., dry eye disease.

Aspects of the invention include systems comprising: (i) a sensor comprising a sensing surface comprising a coated region, wherein the sensor is configured to: direct a first optical signal to interact with the sensing surface at a first incident angle; and direct a second optical signal to interact with the sensing surface at a second incident angle; and (ii) an optical chassis comprising: an optical signal generating component; a detection component; a processor; a controller; and a computer-readable medium comprising instructions that, when executed by the processor, cause the controller to: direct an optical signal having a first wavelength to interact with the sensing surface at the first incident angle to generate a first surface plasmon resonance (SPR) signal; generate a series of images of the first SPR signal over a first time interval using the detection component; determine a series of pixel positions that correspond to a minimum value of the first SPR signal over the first time interval; direct an optical signal having a second wavelength to interact with the sensing surface at the first incident angle to generate a second SPR signal; generate a series of images of the second SPR signal over a second time interval using the detection component; determine a series of pixel positions that correspond to a minimum value of the second SPR signal over the second time interval; compare the series of pixel positions that correspond to the minimum value of the first SPR signal over the first time interval to the pixel position of at least one reference feature to generate a first reference-corrected SPR function; compare the series of pixel positions that correspond to the minimum value of the second SPR signal over the second time interval to the pixel position of the at least one reference feature to generate a second reference-corrected SPR function; and compare one or more characteristics of the first reference-corrected SPR function and the second reference-corrected SPR function to determine a reference-corrected SPR delta pixel value.

In some embodiments, the first incident angle ranges from about 40 to about 70 degrees. In some embodiments, the first incident angle ranges from about 62 to about 67 degrees. In some embodiments, the first incident angle is about 64 degrees. In some embodiments, the computer-readable medium further comprises instructions that, when executed by the processor, cause the controller to compare the reference-corrected SPR delta pixel value to a calibration data set.

In some embodiments, the computer-readable medium further comprises instructions that, when executed by the processor, cause the controller to: direct an optical signal having a first wavelength to interact with the sensing surface at a second incident angle to generate a third surface plasmon resonance (SPR) signal; generate an image of the third SPR signal using the detection component; determine a pixel position of a minimum value of the third SPR signal on the generated image; direct an optical signal having a second wavelength to interact with the sensing surface at the second incident angle to generate a fourth SPR signal; generate an image of the fourth SPR signal using the detection component; determine a pixel position of a minimum value of the fourth SPR signal on the generated image; and compare the pixel position of the minimum value of the third SPR signal to the pixel position of the minimum value of the fourth SPR signal to determine an SPR delta pixel value.

In some embodiments, the second incident angle ranges from about 40 to about 70 degrees. In some embodiments, the second incident angle ranges from about 40 to about 45 degrees. In some embodiments, the second incident angle is about 42 degrees.

In some embodiments, the computer-readable medium further comprises instructions that, when executed by the processor, cause the controller to compare the SPR delta pixel value to a calibration data set.

In some embodiments, the computer-readable medium further comprises instructions that, when executed by the processor, cause the controller to: direct the optical signal having the first wavelength to interact with the sensing surface at the second incident angle to generate a first critical angle signal; generate an image of the first critical angle signal using the detection component; determine a pixel position of a maximum value of the first critical angle signal on the generated image; direct an optical signal having a second wavelength to interact with the sensing surface at the first incident angle to generate a second critical angle signal; generate an image of the second critical angle signal using the detection component; determine a pixel position of a maximum value of the second critical angle signal on the generated image; and compare the pixel position of the maximum values of first and second critical angle signals to determine a critical angle delta pixel value.

In some embodiments, the sensor comprises a coated region and a non-coated region, and wherein the first and second critical angle signals are generated from the non-coated region. In some embodiments, the reference feature comprises a pixel position of one or more opto-mechanical reference features. In some embodiments, the reference feature comprises the pixel position of the minimum value of the third SPR signal, the pixel position of the minimum value of the fourth SPR signal, the SPR delta pixel value, or a combination thereof. In some embodiments, the reference feature comprises the pixel position of the maximum value of the first critical angle signal, the pixel position of the maximum value of the second critical angle signal, the critical angle delta pixel value, or a combination thereof. In some embodiments, the characteristic of the first and second reference-corrected SPR functions comprises a derivative of the first and second reference-corrected SPR functions. In some embodiments, the characteristic of the first and second reference-corrected SPR functions comprises a plateau value of the first and second reference-corrected SPR functions. In some embodiments, the sensor is configured to be removably coupled to the optical chassis. In some embodiments, the system is a benchtop system. In some embodiments, the system is a hand-held system.

Aspects of the invention include methods for determining the osmolarity of a sample, the method comprising: contacting a sensing surface of a system as described herein with the sample; directing the optical signal having the first wavelength to interact with the sensing surface at the first incident angle to generate a first surface plasmon resonance (SPR) signal; generating a series of images of the first SPR signal over a first time interval using the detection component; determining a series of pixel positions that correspond to a minimum value of the first SPR signal over the first time interval; directing the optical signal having the second wavelength to interact with the sensing surface at the first incident angle to generate a second SPR signal; generating a series of images of the second SPR signal over a second time interval using the detection component; determining a series of pixel positions that correspond to a minimum value of the second SPR signal over the second time interval; comparing the series of pixel positions that correspond to the minimum value of the first SPR signal over the first time interval to the pixel position of at least one reference feature to generate a first reference-corrected SPR function; comparing the series of pixel positions that correspond to the minimum value of the second SPR signal over the second time interval to the pixel position of the at least one reference feature to generate a second reference-corrected SPR function; comparing one or more characteristics of the first reference-corrected SPR function and the second reference-corrected SPR function to determine a reference-corrected SPR delta pixel value; and comparing the reference-corrected SPR delta pixel value to a calibration data set to determine the osmolarity of the sample.

In some embodiments, the methods further comprise: contacting the sensing surface with a reference medium; directing the optical signal having the first wavelength to interact with the sensing surface at the second incident angle to generate a third surface plasmon resonance (SPR) signal; generating an image of the third SPR signal using the detection component; determining a pixel position of a minimum value of the third SPR signal on the generated image; directing the optical signal having the second wavelength to interact with the sensing surface at the second incident angle to generate a fourth SPR signal; generating an image of the fourth SPR signal using the detection component; determining a pixel position of a minimum value of the fourth SPR signal on the generated image; and comparing the pixel position of the minimum value of the third SPR signal to the pixel position of the minimum value of the fourth SPR signal to determine an SPR delta pixel value.

In some embodiments, the methods further comprise comparing the SPR delta pixel value to the reference-corrected SPR delta pixel value. In some embodiments, the methods further comprise comparing the SPR delta pixel value to a calibration data set. In some embodiments, the methods further comprise: directing the optical signal having the first wavelength to interact with the sensing surface at the second incident angle to generate a first critical angle signal; generating an image of the first critical angle signal using the detection component; determining a pixel position of a maximum value of the first critical angle signal on the generated image; directing the optical signal having the second wavelength to interact with the sensing surface at the second incident angle to generate a second critical angle signal; generating an image of the second critical angle signal using the detection component; determining a pixel position of a maximum value of the second critical angle signal on the generated image; and comparing the pixel position of the maximum values of first and second critical angle signals to determine a critical angle delta pixel value. In some embodiments, the methods further comprise comparing the critical angle delta pixel value to the reference-corrected SPR delta pixel value. In some embodiments, the methods further comprise comparing the critical angle delta pixel value to the SPR delta pixel value. In some embodiments, the methods further comprise comparing the critical angle delta pixel value to a calibration data set.

In some embodiments, the images of the SPR signals are captured in a single image frame. In some embodiments, the images of the SPR signals and the images of the critical angle signals are captured in a single image frame.

In some embodiments, the methods further comprise: comparing the reference-corrected SPR delta pixel value, the SPR delta pixel value, or the critical angle delta pixel value to an external environment parameter to generate an external environment corrected delta pixel value; and comparing the external environment corrected delta pixel value to a calibration data set. In some embodiments, the external environment parameter is selected from the group comprising: temperature, pressure, humidity, light, environmental composition, or any combination thereof.

In some embodiments, the optical signals having a first and a second wavelength are directed to interact with the sensing surface simultaneously. In some embodiments, the optical signals having a first and second wavelength are directed to interact with the sensing surface in a gated manner. In some embodiments, the calibration data set is stored in a read-only memory of a processor of the system.

In some embodiments, the sample is a biological sample. In some embodiments, the biological sample is a tear fluid. In some embodiments, the reference medium is air.

In some embodiments, the first time interval ranges from about 0.001 seconds to about 90 seconds. In some embodiments, the second time interval ranges from about 0.001 seconds to about 90 seconds.

BRIEF DESCRIPTION OF THE DRAWINGS

FIG. 13 is a table showing the location of SPR minima for 10 SPR images sequentially acquired at approximately 1.0 second intervals.

FIG. 20 shows quadratic and cubic equation solutions that can be used to determine the pixel position corresponding to SPR minimum value.

DETAILED DESCRIPTION

Figure 1:
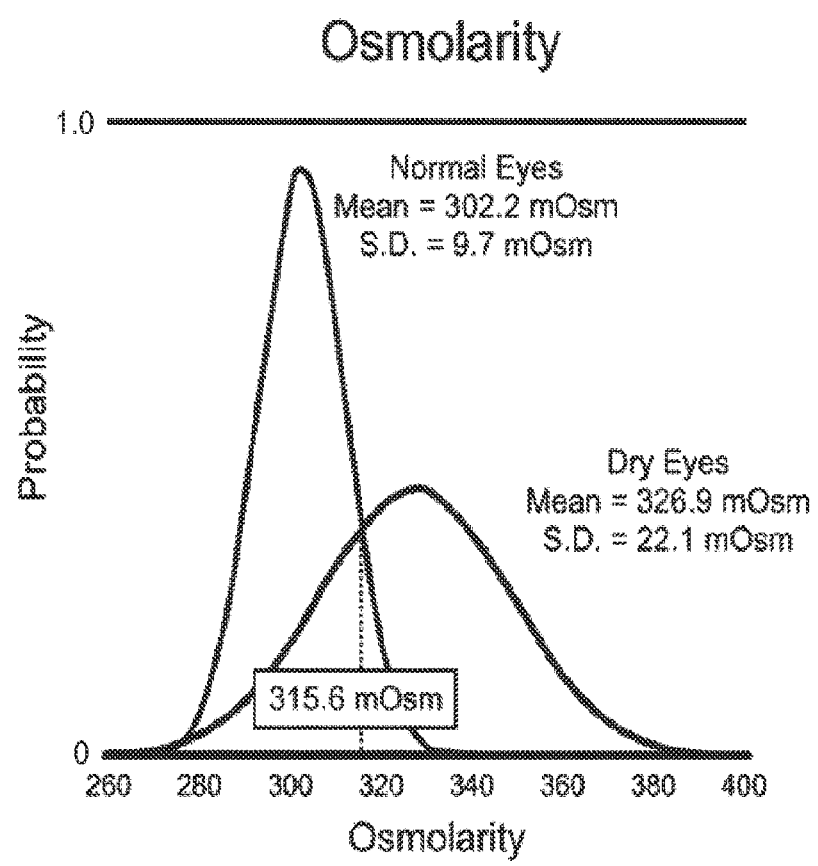
FIG. 1 is a graph showing a relationship between tear osmolarity and probability for normal eyes and dry eyes.

Systems and methods for determining the osmolarity of a sample are provided. Aspects of the subject methods include contacting a sensing surface of a sensor with a sample, and generating one or more data sets over a time interval, wherein the data sets are used to determine the osmolarity of the sample. The subject methods find use in determining the osmolarity of a sample, such as a biological sample (e.g., a tear fluid), and in the diagnosis and/or monitoring of various diseases and disorders, such as, e.g., dry eye disease.

Before the present invention is described in greater detail, it is to be understood that this invention is not limited to particular aspects described, as such may, of course, vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which can be readily separated from or combined with the features of any of the other several aspects without departing from the scope or spirit of the present invention. Any recited method can be carried out in the order of events recited or in any other order which is logically possible.

Definitions

The term "sensing surface" as used herein refers to a surface of a sensor that is configured to contact an external medium.

The terms "incident angle" or "angle of incidence" as used interchangeably herein refer to an angle that is formed between a beam of light that is directed toward a planar surface, and a line that is perpendicular to the same planar surface.

The term "facet" as used herein refers to a substantially planar portion of a surface (e.g., an interior surface or an exterior surface) of a sensor.

The term "semitransparent film" as used herein refers to a film that is partially transparent to light and facilitates surface plasmon/polariton generation.

The terms "reflective coating" and "reflective film", as used interchangeably herein, refer to a coating or a film, respectively, that are capable of reflecting light or other radiation. The terms "semitransparent film" and "reflective film" or "reflective coating" as used herein are not mutually exclusive, and a given film can be both a semitransparent film as well as a reflective film.

The term "noble metal" as used herein refers to a metallic element that is resistant to corrosion in moist air. Non-limiting examples of noble metals include Copper (Cu), Ruthenium (Ru), Rhodium (Rh), Palladium (Pd), Silver (Ag), Rhenium (Re), Osmium (Os), Iridium (Ir), Platinum (Pt), Gold (Au), Mercury (Hg), or combinations thereof.

The term "adhesion layer" as used herein refers to a layer of material that is formed on a sensing surface or on a facet, and which facilitates adhesion of a coating material (e.g., a reflective film or a semitransparent film) to the sensing surface or facet.

The term "coated region" as used herein with reference to a sensing surface or facet means a region of the sensing surface or facet that is covered with a coating (e.g., a semitransparent film, a reflective coating, and/or an adhesion layer). The term "non-coated region" as used herein with reference to a sensing surface or facet means a region of the sensing surface or facet that is not covered with a coating.

The term "optical chassis" as used herein refers to a structure that supports and/or contains one or more optical components.

The term "optical signal" as used herein refers to a signal that comprises photons.

The term "critical angle" as used herein refers to an angle of incidence above which (e.g., at an angle of incidence having a larger angular value than the critical angle) total internal reflection occurs.

The term "pixel position" as used herein refers to the position of a pixel on a coordinate system, such as, e.g., an x,y coordinate plane.

The term "compare" as used herein with respect to comparing pixel positions refers to measuring a difference in position of two or more pixels on a coordinate plane. Comparing of pixel positions can be qualitative or quantitative.

The term "reference feature" as used herein refers to one or more data points that do not vary with time, or a component that is configured or adapted to generate one or more data points that do not vary with time.

The term "opto-mechanical reference" or "OMR" refers to a component that is configured or adapted to place a physical obstruction in the path of one or more optical signals and to thereby generate one or more reference signals that do not vary with time, and that can be detected and analyzed by a detection component.

The terms "delta pixel position" or "delta pixel value" as used herein refer to a numerical value that represents a difference in position between two pixels on a coordinate system.

The term "external environment parameter" as used herein refers to a characteristic of an environment that is external to a subject sensor or system. A non-limiting example of an external environment parameter is the temperature of a room in which a sensor is operated.

The term "corrected" as used herein with respect to a data value refers to a data value that has undergone a mathematical manipulation, e.g., has been multiplied or divided by a numerical value to correct or normalize the data value based on a given parameter (e.g., an external environment parameter, or a reference value).

The term "reference-corrected" as used herein with respect to a data value or a mathematical function (e.g., an SPR function) refers to a data value or mathematical function that has undergone a mathematical manipulation, e.g., has been multiplied or divided by at least one numerical value obtained from one or more reference features to correct or normalize the data value based on the at least one numerical value obtained from the reference feature.

The term "calibration data set" as used herein refers to a collection of one or more data points that represent a relationship between a measurement standard and a characteristic that is measured by a subject sensor and/or system.

The term "function" as used herein refers to a mathematical operation, or graphical representation thereof, wherein a unique y coordinate value is assigned to every x coordinate value.

The term "minimum value" as used herein refers to the lowest numerical value of a function in an image frame and on a given coordinate system.

The term "maximum value" as used herein refers to the highest numerical value of a function in an image frame and on a given coordinate system.

The term "derivative" as used herein refers to a rate of change of a function. The value of a derivative of a function is the slope of the tangent line at a point on a graph representing the function.

The term "plateau value" as used herein refers to a y-value of a function over a region where the function has a substantially constant, or steady-state, y-value.

The term "quality parameter" as used herein refers to an aspect of a subject sensor or system that is required for optimal functioning of the sensor or system.

The term "surface plasmon resonance" or "SPR" as used herein refers to a resonant oscillation of conduction electrons at an interface between a negative and a positive permittivity material that is stimulated by incident light.

The term "optical signal manipulation component" as used herein refers to a component that is capable of manipulating one or more features of an optical signal. An optical signal manipulation component can include any number of individual components, which individual components can act in parallel and/or in series to manipulate one or more characteristics of an optical signal. Non-limiting examples of optical signal manipulation components include: beam splitters, spatial filters, filters that reduce external ambient light, lenses, polarizers, and optical waveguides.

The term "removably couple" as used herein refers to connecting two or more components in such a way that the connection is reversible, and the components can be separated from one another.

The term "retention component" as used herein refers to a component that is configured to retain one or more components in a fixed position with respect to another component.

The term "alignment component" as used herein refers to a component that is configured to provide functional and/or structural alignment between two or more components that are operably coupled.

The term "kinematic mounting component" as used herein refers to a mounting component that provides a number of constraints that is equal to the number of degrees of freedom in the component being mounted.

The term "benchtop system" as used herein refers to a system that is configured to be disposed on a surface of, e.g., a laboratory benchtop, or another suitable substrate, during operation.

The term "hand-held system" as used herein refers to a system, or a component thereof, that is configured to be held in a user's hand during operation.

The terms "subject" or "patient" as used herein refer to any human or non-human animal.

Sensors and Systems

Aspects of the invention include sensors and systems configured to carry out the subject methods, e.g., to determine the osmolarity of a sample. In certain embodiments, the subject systems include an optical sensor having at least one sensing surface and configured to direct a first optical signal to interact with the sensing surface at a first incident angle, and to direct a second optical signal to interact with the sensing surface at a second incident angle. In some embodiments, the subject systems further include an optical chassis that includes an optical signal generation component and a detection component. Each of these components is now further described in greater detail.

Sensors

As summarized above, aspects of the invention include sensors that include at least one sensing surface, and that are configured to direct a first optical signal to interact with the sensing surface at a first incident angle, and to direct a second optical signal to interact with the sensing surface at a second incident angle. By directing optical signals to interact with the sensing surface at two different incident angles, the subject sensors are capable of generating data from the sensing surface for two or more different media (e.g., air and water), and detecting the data using the same detection component. As such, data obtained from different media can be captured in the same field of view, or image frame, of a detection component, and can then be analyzed by the detection component. Analysis of the data can then be used to determine one or more characteristics of the media. The inclusion of data from the sensing surface for different media in the same field of view, or image frame, of the detection component provides an internal reference within the data that can be used in analysis (e.g., can be used for calibration of the sensor and/or for analyzing an unknown sample). As described further herein, in some embodiments, a sensor can include a reference feature that can be used in data analysis. In some embodiments, a sensor comprises a reference feature that creates a reference signal in an image frame of the detection component, and one or more pixel positions of the reference signal can be used as an internal reference for purposes of data analysis (e.g., can be used for calibration of the sensor and/or for analyzing a known or unknown sample).

Figure 2:
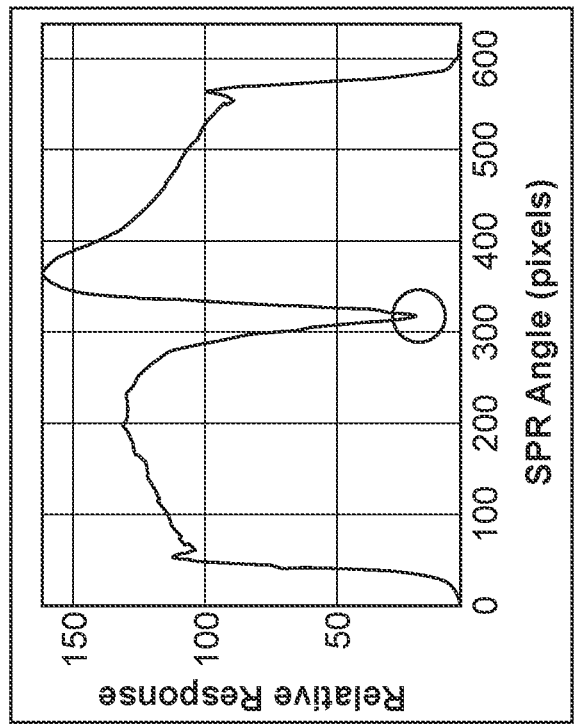
FIG. 2, Panel A is an illustration demonstrating the Surface Plasmon Resonance (SPR) technique for measuring the osmolarity of a tear fluid. Panel B is a graph showing relative response as a function of SPR angle.
Figure 2:
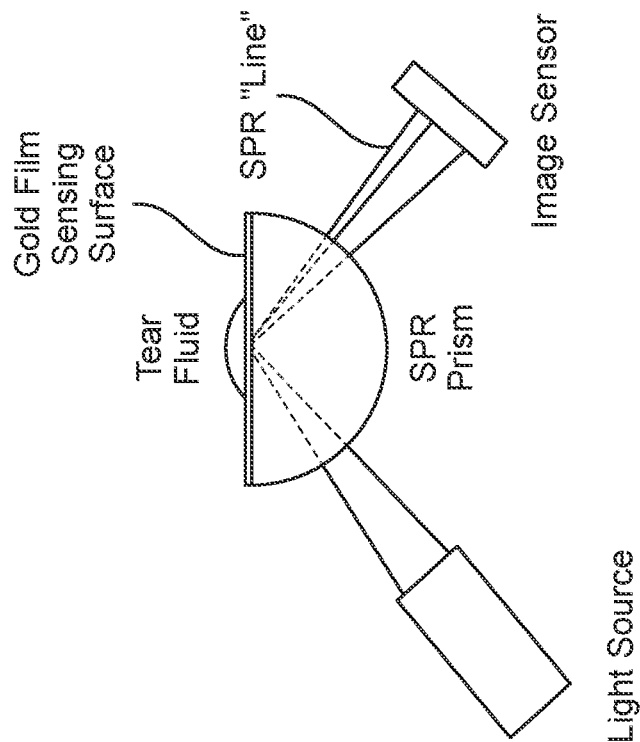

The subject sensors include at least one sensing surface that comprises a semitransparent film, wherein the semitransparent film comprises a noble metal. The semitransparent film facilitates surface plasmon resonance (SPR)-based analysis of a medium in contact with the sensing surface. SPR is a phenomenon that occurs when light is incident on a sensing surface at a particular angle, so that the reflected light is extinguished. At a particular angle of incident light, the intensity of the reflected light shows a characteristic curve of diminishing intensity, well defined by mathematical equations. The angle of incident light that corresponds to a reflectivity minimum of the curve is influenced by the characteristics of the semitransparent film and the external medium that is in contact therewith. FIG. 2, Panel A provides an illustrative overview of the SPR technique for tear osmolarity measurement. FIG. 2, Panel B provides a graph of an SPR signal (i.e., an SPR signal curve, or function), demonstrating the relative minimum of the SPR curve, and indicating the position corresponding to a reflectivity minimum of the SPR signal curve. In some embodiments, aspects of the invention include determining a pixel position corresponding to a reflectivity minimum of an SPR signal curve represented on an image that is generated by a detection component (described further herein).

In some embodiments, the semitransparent film on the sensing surface can range in thickness from about 0.5 nm up to about 200 nm, such as about 1 nm, 5 nm, 10 nm, 15 nm, 20 nm, 25 nm, 30 nm, 35 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 60 nm, 65 nm, 70 nm, 75 nm, 80 nm, 85 nm, 90 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, or 195 nm. A semitransparent film can be deposited on a surface of a sensor using any suitable technique, for example, thin film deposition techniques (e.g., atomic layer deposition (ALD), chemical vapor deposition (CVD), evaporative deposition, metal organic chemical vapor deposition (MOCVD), sputtering, etc.), or any combination thereof. Non-limiting examples of noble metals that can be used in a semitransparent film in accordance with embodiments of the subject sensors include Copper (Cu), Ruthenium (Ru), Rhodium (Rh), Palladium (Pd), Silver (Ag), Rhenium (Re), Osmium (Os), Iridium (Ir), Platinum (Pt), Gold (Au), Mercury (Hg), or any combination thereof. In some embodiments, a semitransparent film on a sensing surface can be composed of a plurality of discrete layers of material, wherein the material in each layer can be selected from the noble metals described above, or any combination thereof (e.g., alloys thereof, such as alloys of 2, 3, 4, 5, 6, 7, or 8 or more different noble metals). In some embodiments, a sensing surface can comprise a substrate, such as, e.g., a microscope slide, having one side that is at least partially coated with a semitransparent film. In such embodiments, the substrate can be operably coupled to the sensor to provide a sensing surface.

In some embodiments, a sensor can include an adhesion layer that is deposited on a sensing surface between the sensor (or substrate) and a semitransparent film. An adhesion layer in accordance with embodiments of the invention serves to promote adhesion of the semitransparent film to the sensing surface, and can modulate one or more properties of an optical signal passing through the sensor. For example, in some embodiments, an adhesion layer can comprise a material that improves a desired property of an optical signal that passes through the adhesion layer. In some embodiments, the thickness and material composition of an adhesion layer are selected to favorably manipulate a property of an optical signal that passes through the adhesion layer. In some embodiments, a material having a desired refractive index (RI) is selected to modulate a characteristic of an optical signal that passes through the adhesion layer. In some embodiments, the adhesion layer comprises a material that modulates a characteristic of an optical signal passing therethrough, e.g., reduces the amount of noise in the optical signal.

In some embodiments, an adhesion layer can range in thickness from about 0.5 nm up to about 200 nm, such as about 1 nm, 1.5 nm, 2 nm, 2.5 nm, 3 nm, 3.5 nm, 4 nm, 4.5 nm, 5 nm, 5.5 nm, 6 nm, 6.5 nm, 7 nm, 7.5 nm, 8 nm, 8.5 nm, 9 nm, 9.5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, or 195 nm. An adhesion layer can be deposited on a surface of the sensor using any suitable technique, for example, thin film deposition techniques (e.g., atomic layer deposition (ALD), chemical vapor deposition (CVD), evaporative deposition, metal organic chemical vapor deposition (MOCVD), sputtering, etc.), or any combination thereof. Non-limiting examples of materials that can be used in an adhesion layer in accordance with embodiments of the subject sensors include Chromium (Cr), $TiO_2$, $TO_x$, $SiO_2$, $SiO_x$, or any combination thereof (e.g., mixtures or alloys thereof).

Sensing surfaces in accordance with embodiments of the invention can have any suitable size and shape. In some embodiments, a sensing surface can be square, rectangular, trapezoidal, octagonal, elliptical, or circular in shape, or any combination thereof. The surface area of a sensing surface can vary, and in some embodiments can range from about 1 $mm^2$ up to about 10 $mm^2$, such as about 2 $mm^2$, 3 $mm^2$, 4 $mm^2$, 5 $mm^2$, 6 $mm^2$, 7 $mm^2$, 8 $mm^2$, or 9 $mm^2$.

In certain embodiments, a sensing surface can comprise a coated region and a non-coated region. In some embodiments, a coated region comprises a percentage of the area of the sensing surface that ranges from about 10% up to 100%, such as about 15%, 20%, 25%, 30%, 35%, 40%, 45%, 50%, 55%, 60%, 65%, 70%, 75%, 80%, 85%, 90%, or 95% of the area of the sensing surface. In certain embodiments, an entire sensing surface is coated with a semitransparent film.

A coated region in accordance with embodiments of the invention can have any suitable shape. In some embodiments, a coated region of a sensing surface can be square, rectangular, trapezoidal, octagonal, elliptical, or circular in shape, or any combination thereof. In some embodiments, a sensing surface can comprise a plurality of discrete coated regions, such as 2, 3, 4, 5, 6, 7, 8, 9 or 10 discrete coated regions. A coated region of a sensing surface can be located in any suitable position on a sensing surface. For example, in some embodiments, a coated region can be centered on a sensing surface, while in some embodiments, a coated region can be, e.g., located on one particular side of a sensing surface, located along one or more sides of a sensing surface, or the like. In some embodiments, approximately half of the sensing surface comprises a coated region, while approximately half of the sensing surface comprises a non-coated region. In some embodiments, approximately two thirds (approximately 66%) of the sensing surface comprises a coated region, while approximately one third (approximately 33%) of the sensing surface comprises a non-coated region. In certain embodiments, the entire surface of a sensing surface is a coated region (i.e., 100% of the sensing surface is coated with a semitransparent film).

In some embodiments, a non-coated region of a sensing surface facilitates analysis of a critical angle associated with the sensor. The critical angle is the incident angle above which total internal reflection occurs. The critical angle is influenced by the characteristics of the material from which the sensor is made, and is not influenced by the external medium that is in contact with a sensing surface of the sensor. As such, the critical angle for a given sensor can serve as an internal reference during analysis. In some embodiments, aspects of the invention include determining a critical angle for a sensor, as well as determining a pixel position corresponding to the critical angle on an image that is generated by a detection component (described further herein).

Sensors in accordance with embodiments of the invention can have any suitable size and shape. In some embodiments, a sensor has a hemi-cylinder shape, having a planar surface and a curved surface, wherein the sensing surface is disposed on the planar surface. In some embodiments, a sensor comprises a conical or frustoconical shape. In some embodiments, a sensor can have a concave shape, such that the sensor comprises an interior surface (e.g., a surface inside the concavity) and an exterior surface. In some embodiments, a sensor can have a frustoconical, concave shape.

In some embodiments, a sensor can have a length dimension that ranges from about 1 to about 20 cm, such as 2 cm, 3 cm, 4 cm, 5 cm, 8 cm, 10 cm, 12 cm, 14 cm, 16 cm, or 18 cm. In some embodiments, a sensor can have a width dimension that ranges from about 1 to about 20 cm, such as 2 cm, 3 cm, 4 cm, 5 cm, 8 cm, 10 cm, 12 cm, 14 cm, 16 cm, or 18 cm. In some embodiments, a sensor can have a height dimension that ranges from about 1 to about 20 cm, such as 2 cm, 3 cm, 4 cm, 5 cm, 8 cm, 10 cm, 12 cm, 14 cm, 16 cm, or 18 cm. In some embodiments, a sensor can have a diameter that ranges from about 1 to about 20 cm, such as 2 cm, 3 cm, 4 cm, 5 cm, 8 cm, 10 cm, 12 cm, 14 cm, 16 cm, or 18 cm.

In some embodiments, a sensor can comprise one or more facets that are configured to direct an optical signal in a given direction (e.g., to reflect off the facet at a given angle). Facets in accordance with embodiments of the invention can have any suitable area, and in some embodiments can range in area from about 1 $mm^2$ up to about 100 $mm^2$, such as about 5 $mm^2$, 10 $mm^2$, 15 $mm^2$, 20 $mm^2$, 25 $mm^2$, 30 $mm^2$, 35 $mm^2$, 40 $mm^2$, 45 $mm^2$, 50 $mm^2$, 55 $mm^2$, 60 $mm^2$, 65 $mm^2$, 70 $mm^2$, 75 $mm^2$, 80 $mm^2$, 85 $mm^2$, 90 $mm^2$, or 95 $mm^2$. Facets in accordance with embodiments of the sensor can have any suitable shape, and in some embodiments can be square, rectangular, trapezoidal, octagonal, elliptical, or circular in shape, or any combination thereof.

Sensors in accordance with embodiments of the invention can have any suitable number of facets on a given surface of the sensor. For example, in some embodiments, a sensor can have a number of facets ranging from 1 up to 10, such as 2, 3, 4, 5, 6, 7, 8 or 9 facets on a given surface of the sensor. In certain embodiments, a sensor can have one or more facets on an internal surface, such as 1, 2, 3, 4, 5, 6, 7, 8, 9, or 10 facets on an internal surface, and can also have one or more facets on an external surface, such as 1, 2, 3, 4, 5, 6, 7, 8, 9, or 10 facets on an external surface. In some embodiments, a facet can be coated with an optically reflective material to enhance the ability of the facet to reflect an optical signal. In some embodiments, a plurality of facets can have a different shape and/or area. In some embodiments, a plurality of facets can have the same shape and/or area.

In certain embodiments, one or more facets can be coated with a reflective coating (e.g., a reflective film, or an optically reflective material). In some embodiments, all of the facets of a sensor can be coated with a reflective coating. In some embodiments, certain facets on a sensor are coated with a reflective coating, whereas other facets on the same sensor are not coated with a reflective coating. In some embodiments, the entire surface of a selected facet can be coated with a reflective coating. In some embodiments, only a portion or section of the surface of a particular facet is coated with a reflective coating. In a preferred embodiment, a plurality of "shoulder" facets are coated with a reflective gold coating. For example, in one preferred embodiment, the facets that are labeled in FIG. 43 (as well as those that are symmetrically located on the opposite side of the sensing surface) are coated with a reflective coating (e.g., a reflective gold coating).

In some embodiments, a reflective coating on the surface of a facet can range in thickness from about 0.1 nm up to about 1,000 nm (1 µm), such as about 0.5 nm, about 1 nm, about 5 nm, about 10 nm, about 20 nm, about 30 nm, about 40 nm, about 50 nm, about 60 nm, about 70 nm, about 80 nm, about 90 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, or about 950 nm or more. A reflective coating can be deposited on a surface of a facet using any suitable technique, such as, for example, thin film deposition techniques (e.g., atomic layer deposition (ALD), chemical vapor deposition (CVD), evaporative deposition, metal organic chemical vapor deposition (MOCVD), sputtering, etc.), or any combination thereof. Non-limiting examples of noble metals that can be used in a reflective film in accordance with embodiments of the subject sensors include Copper (Cu), Ruthenium (Ru), Rhodium (Rh), Palladium (Pd), Silver (Ag), Rhenium (Re), Osmium (Os), Iridium (Ir), Platinum (Pt), Gold (Au), Mercury (Hg), or any combination thereof. In a preferred embodiment, a reflective coating comprises gold (Au).

In some embodiments, a sensor can include an adhesion layer that is deposited on one or more facets and is positioned between the sensor (or substrate) and a reflective coating on the facet. An adhesion layer in accordance with embodiments of the invention serves to promote adhesion of the reflective coating to the facet, and can modulate one or more properties of an optical signal that is reflected off the facet. For example, in some embodiments, an adhesion layer can comprise a material that improves a desired property of an optical signal that is reflected off a particular facet. In some embodiments, the thickness and material composition of an adhesion layer are selected to favorably manipulate a property of an optical signal that is reflected off a particular facet.

In some embodiments, an adhesion layer can range in thickness from about 0.5 nm up to about 200 nm, such as about 1 nm, 1.5 nm, 2 nm, 2.5 nm, 3 nm, 3.5 nm, 4 nm, 4.5 nm, 5 nm, 5.5 nm, 6 nm, 6.5 nm, 7 nm, 7.5 nm, 8 nm, 8.5 nm, 9 nm, 9.5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, or 195 nm. An adhesion layer can be deposited on a surface of the sensor (e.g., on a facet of the sensor) using any suitable technique, for example, thin film deposition techniques (e.g., atomic layer deposition (ALD), chemical vapor deposition (CVD), evaporative deposition, metal organic chemical vapor deposition (MOCVD), sputtering, etc.), or any combination thereof. Non-limiting examples of materials that can be used in an adhesion layer in accordance with embodiments of the subject sensors include Chromium (Cr), $TiO_2$, $TO_x$, $SiO_2$, $SiO_x$, or any combination thereof (e.g., mixtures or alloys thereof).

In some embodiments, a sensor can include one or more identification components that are configured to communicate identifying information to another component of a system (e.g., to a component of an optical chassis, to a processor, etc.). For example, in some embodiments, a sensor can include an identification component that provides an optical chassis with information regarding, e.g., a type of semitransparent film disposed on the sensing surface of the sensor, a configuration of coated and non-coated regions on a sensing surface of the sensor, a configuration of facets in the sensor, etc. In some embodiments, a system is configured to respond to identifying information communicated by a sensor. For example, in certain embodiments, a system can be configured to receive identifying information from a sensor, and in response, configure the system to carry out a particular method of analysis (e.g., configure the system to generate one or more optical signals having a particular wavelength or wavelengths). Identification components in accordance with embodiments of the invention can have any suitable structure, and can include, for example, bar codes, magnetic strips, computer-readable chips, and the like. Systems in accordance with embodiments of the invention can be configured with a corresponding identification component that is configured to receive and/or identify identification information from an identification component on a sensor.

Aspects of the subject sensors include retention components that are configured to retain a sensor in a fixed position with respect to another component of a subject system (e.g., an optical chassis, described further herein). Retention components in accordance with embodiments of the invention can have any suitable shape and dimensions, and can take the form of, e.g., tabs or flanges that extend from one or more portions of a subject sensor. In some embodiments, a sensor can include a retention component that is configured to removably couple the sensor to another component, such as, e.g., an optical chassis. In some embodiments, a sensor is configured to be removably coupled and/or de-coupled to an optical chassis in a touchless, or aseptic manner, meaning that an operator can accomplish the coupling of the sensor to the optical chassis without compromising the sterility of the sensor, and can accomplish de-coupling the sensor from the optical chassis without having to physically contact the sensor.

Aspects of the subject systems include one or more sensor mounting components that are configured to facilitate aseptic handling of a sensor, as well as coupling (e.g., removable coupling) of the sensor to an optical chassis. For example, in certain embodiments a sensor mounting component is configured to hold a sensor in an aseptic manner, allow a user to couple the sensor to an optical chassis, and then disengage from the sensor, leaving the sensor coupled to the optical chassis in an aseptic manner. Sensor mounting components in accordance with embodiments of the invention can have any suitable dimensions, and in some embodiments include a surface that is complementary to at least a portion of a sensor. In some embodiments, a sensor mounting component is configured to cover at least a portion of an external surface of a sensor so that the covered portion of the sensor is not accessible to an external environment until the sensor mounting component is disengaged from the sensor. In some embodiments, a sensor mounting component is adapted for sterilization via any suitable technique, and is adapted to maintain its functionality after the sterilization has been completed. Sterilization techniques are well known in the art and include, e.g., heat sterilization, gamma irradiation, chemical sterilization (e.g., ethylene oxide gas sterilization), and many others. Aspects of the invention include sensor mounting components that are adapted for sterilization without altering their functionality in any appreciable manner. In some embodiments, a sensor mounting component is configured to allow sterilization of a sensor while the sensor and the sensor mounting component are coupled to one another.

Aspects of the subject sensors include one or more kinematic mounting components that are configured to provide a number of constraints that is equal to the number of degrees of freedom of the component being mounted. For example, for a three dimensional object having six degrees of freedom, kinematic mounting components that provide six constraints can be used to mount a sensor on an optical chassis (described further below).

Aspects of the subject sensors include one or more alignment components that are configured to align the sensor with one or more components of an optical chassis (described further below). In some embodiments, an alignment component can comprise a tapered centering component that is configured to align a sensor with an optical chassis.

The subject sensors can be made from any of a variety of suitable materials, including but not limited to glass, optical grade plastics, polymers, combinations thereof, and the like. Non-limiting examples of suitable materials include polymethylmethacrylate (PMMA), polycarbonate (PC), polystyrene (PS), cyclo-olefin polymers (e.g., ZEONEX® E48R), sapphire, diamond, quartz, zircon (zirconium), and the like, or any combination thereof. In some embodiments, a material that is used to make a subject sensor can have a refractive index that ranges from about 1.2 up to about 2.0, such as 1.21, 1.22, 1.23, 1.24, 1.25, 1.26, 1.27, 1.28, 1.29, 1.3, 1.31, 1.32, 1.33, 1.34, 1.35, 1.36, 1.37, 1.38, 1.39, 1.4, 1.41, 1.42, 1.43, 1.44, 1.45, 1.46, 1.47, 1.48, 1.49, 1.5, 1.51, 1.52, 1.53, 1.54, 1.55, 1.56, 1.57, 1.58, 1.59, 1.6, 1.61, 1.62, 1.63, 1.64, 1.65, 1.66, 1.67, 1.68, 1.69, 1.7, 1.71, 1.72, 1.73, 1.74, 1.75, 1.76, 1.77, 1.78, 1.79, 1.8, 1.81, 1.82, 1.83, 1.84, 1.85, 1.86, 1.87, 1.88, 1.89, 1.9, 1.91, 1.92, 1.93, 1.94, 1.95, 1.96, 1.97, 1.98, or 1.99. Those of skill in the art will recognize that any material having suitable optical properties can be used in the subject sensors. Sensors in accordance with embodiments of the invention can be fabricated using any suitable technique, such as machining, 3D-printing, and/or molding (e.g., injection molding). In some embodiments, a sensor can be fabricated using a suitable technique, and can then be further processed to deposit one or more compositions on a surface of the sensor (e.g., a semitransparent film, adhesion layer, or a reflective coating). In some embodiments, a sensor is disposable, and can be discarded after one or more uses. In some embodiments, a sensor is adapted for repeated use, for example, is adapted to be cleaned and sterilized following use, and then used again.

As reviewed above, aspects of the invention include sensors that are configured to direct a first optical signal to interact with a sensing surface at a first incident angle, and to direct a second optical signal to interact with the sensing surface at a second incident angle so that data from the sensing surface for two different test media (e.g., air and a biological sample, e.g., a tear film) can be captured in the same field of view, or image frame, of a detection component. In some embodiments, a sensor is configured to direct a first optical signal to interact with a sensing surface over a narrow range of first incident angles, and to direct a second optical signal to interact with the sensing surface over a narrow range of second incident angles in order to generate data in the same field of view, or image frame, of a detection component, as reviewed above. In some embodiments, a narrow range of incident angles spans a number of degrees ranging from about 2 to about 10 degrees, such as about 3, 4, 5, 6, 7, 8 or 9 degrees.

Without being held to theory, a range of first and second incident angles that are chosen for a sensor depends on the optical properties of the material that is used to fabricate the sensor, as well as the external medium to be analyzed by the sensor. As such, a first and second incident angle, or a first and second narrow range of incident angles, can differ for sensors that are composed of different materials, and a range of incident angles for a given sensor can be based on the anticipated refractive index of a sample being analyzed (e.g., a biological sample). In some embodiments, a sensor is configured to have a dynamic range of incident angles of clinical significance, wherein the sensor is configured to direct one or more optical signals to interact with a sensing surface over a range of incident angles that facilitate analysis of a sample and provide data having clinical significance (e.g., data that facilitate the determination of the osmolarity of a biological sample, e.g., a tear film). Those of skill in the art will appreciate that different first and second incident angles, or ranges thereof, can be selected based on, e.g., the optical properties of the material that is used to fabricate the sensor, the properties of the external media that will be brought into contact with the sensing surface (e.g., a biological sample and/or a reference medium), the properties of the semitransparent film, and/or the properties of the adhesion layer (if present), in order to generate data in the same field of view of a detection component from the sensing surface for different test media, or different combinations of reference and test media (e.g., air and water, air and tear fluid, etc.). In some embodiments, a range of incident angles broadly spans about 35 degrees to about 75 degrees, such as about 36, 37, 38, 39, 40, 41, 42, 43, 44, 45, 46, 47, 48, 49, 50, 51, 52, 53, 54, 55, 56, 57, 57, 59, 60, 61, 62, 63, 64, 65, 66, 67, 68, 69, 70, 71, 72, 73 or 74 degrees.

In some embodiments, a sensor, when coupled with an optical chassis (as described below) can be formed into a benchtop system that is configured for use in a laboratory setting, e.g., in a clinical laboratory setting. In some embodiments, a sensor, when coupled with an optical chassis (as described below) can be formed into a hand-held system. In a preferred embodiment, a hand-held system has dimensions that are similar to those of a pen. In use, a hand-held system can be held by, e.g., a physician, and contacted with a sample undergoing analysis.

In some embodiments, a sensor is adapted for sterilization via any suitable technique, and is adapted to maintain its functionality after the sterilization has been completed. Sterilization techniques are well known in the art and include, e.g., heat sterilization, gamma irradiation, chemical sterilization (e.g., ethylene oxide gas sterilization), and many others. Aspects of the invention include sensors that are adapted for sterilization without altering their functionality in any appreciable manner.

Aspects of the invention include kits that contain a plurality of sensors. In some embodiments, a kit can contain a plurality of identical sensors. In some embodiments, a kit can contain two or more sensors having different characteristics (e.g., a plurality of a first type of sensor, and a plurality of a second type of sensor). Kits in accordance with embodiments of the invention can comprise any suitable packaging, for example, can comprise airtight packaging (e.g., hermetically sealed packaging), vacuum sealed packaging, and the like. In certain embodiments, a kit can be sterile (e.g., the contents of the kit are sterile, and the kit packaging is configured to maintain the sterility of the contents). In some embodiments, a kit can comprise a plurality of sensors, wherein each individual sensor is separately sealed in sterile packaging. In some embodiments, a kit is not sterile, but is adapted for sterilization so that the kit can be sterilized at a point of use, e.g., at a clinician's office or at a hospital. In some embodiments, a kit can further include one or more sensor mounting components, as described herein.

In some embodiments, a sensor is storage stable and can be stored for an extended period of time, such as one to two years or more, while maintaining its functionality. In certain embodiments, a sensor can be provided in a kit with suitable packaging so that the sensor remains storage stable for an extended period of time. For example, in some embodiments, a sensor can be provided in airtight packaging or vacuum sealed packaging to facilitate storage stability for an extended period of time.

In one preferred embodiment, a sensor is fabricated from a cyclo-olefin polymer and has a frustoconical, concave shape, having an interior surface and an exterior surface, wherein the sensor comprises two facets on the interior surface and four facets on the exterior surface, as well as a sensing surface located on the exterior surface, and wherein the facets are configured to direct a first optical signal to interact with the sensing surface at an incident angle of about 42 degrees, and to direct a second optical signal to interact with the sensing surface at an incident angle of about 64 degrees. In this preferred embodiment, data from both air and water, or from both air and tear fluid, can be collected in the same field of view, or image frame, of a detection component, thereby providing an internal reference within the image that can be used in analysis.

In another preferred embodiment, a sensor is fabricated from a cyclo-olefin polymer and has a frustoconical, concave shape, having an interior surface and an exterior surface, wherein the sensor comprises two facets on the interior surface and four facets on the exterior surface, as well as a sensing surface located on the exterior surface of the sensor, and wherein the facets are configured to direct a first optical signal to interact with a sensing surface over a narrow range of incident angles that ranges from about 40 to about 45 degrees, and is configured to direct a second optical signal to interact with the sensing surface over a narrow range of incident angles that ranges from about 62 to about 67 degrees.

Figure 22:
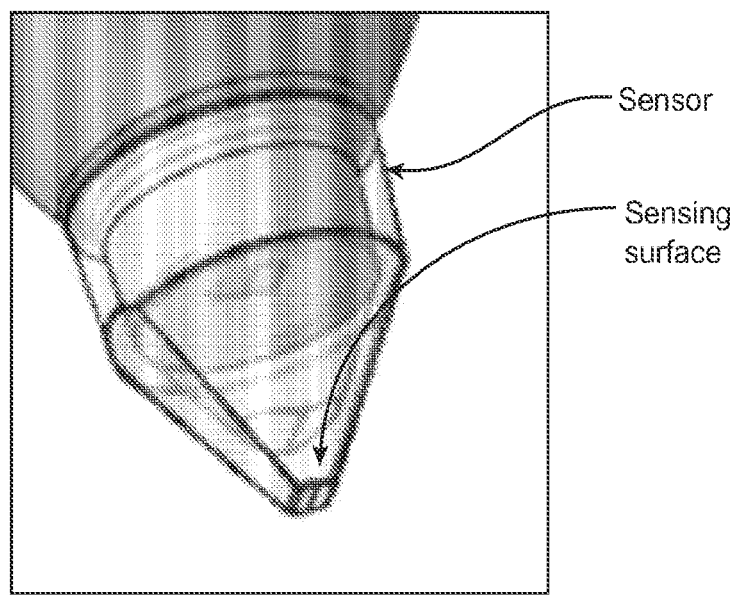
FIG. 22 is an illustration of an example of an injection molded sensor. The sensor and the sensing surface are referenced.

Turning now to FIG. 22, an illustration of a sensor in accordance with one embodiment of the invention is provided. The depicted embodiment is an injection molded clear plastic sensor with a sensing surface that comprises a gold film.

Figure 23:
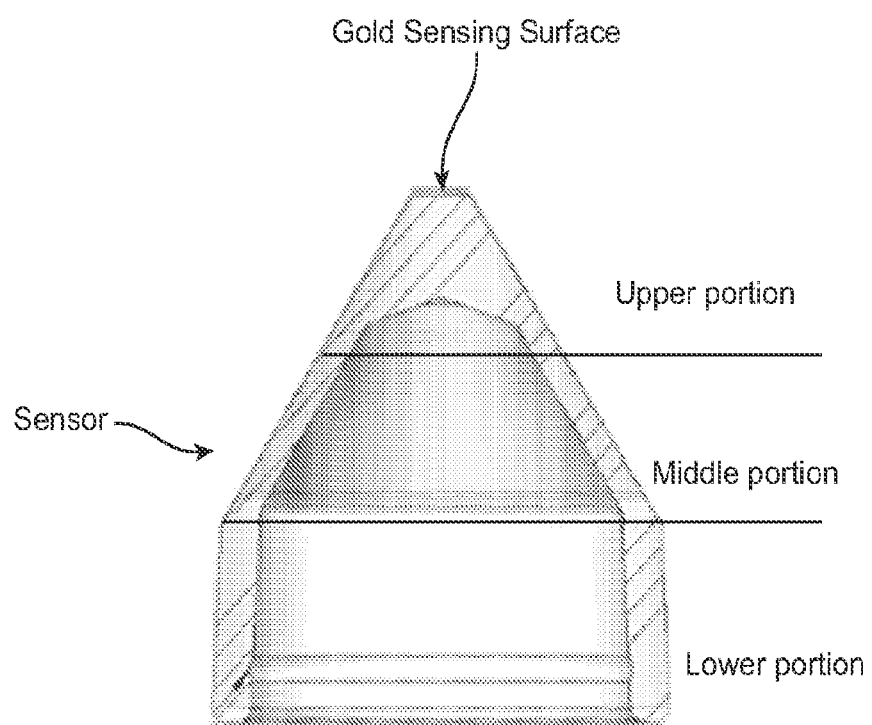
FIG. 23 is an illustration of another example of an injection molded sensor.

FIG. 23 is an illustration of another sensor in accordance with embodiments of the invention. In the depicted embodiment, the sensor comprises a sensing surface with a gold film. An upper portion of the depicted sensor functions as an SPR prism. A middle portion of the depicted sensor is a skirt portion, and the a lower portion of the depicted sensor is a base portion that connects to an optical chassis (described further herein).

Figure 24:
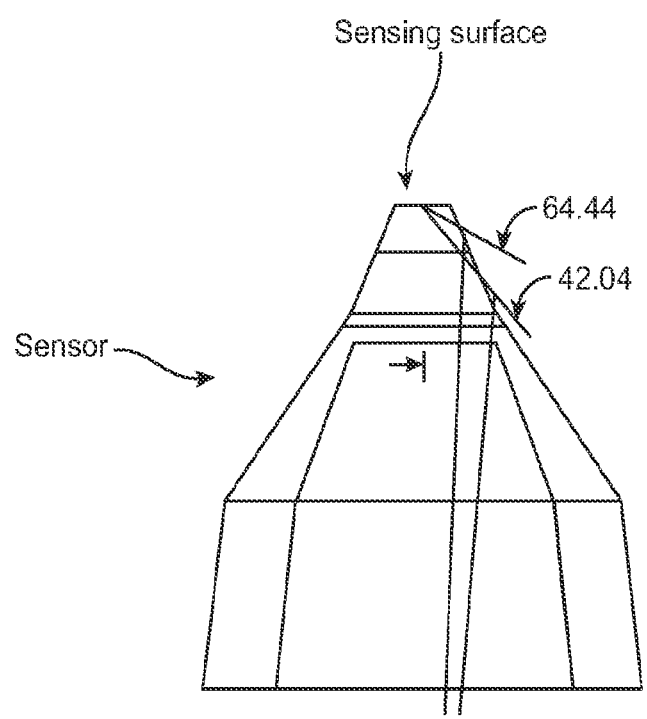
FIG. 24 is an illustration of another example of an injection molded sensor. The depicted sensor is configured to direct a first optical signal to interact with a sensing surface at an incident angle of 42.04 degrees, and to direct a second optical signal to interact with the sensing surface at an incident angle of 64.44 degrees.

FIG. 24 is another illustration of a sensor in accordance with embodiments of the invention. In the depicted embodiment, the sensor is configured to direct a first optical signal to interact with the sensing surface at an incident angle of about 42.04 degrees, and is configured to direct a second optical signal to interact with the sensing surface at an incident angle of about 64.44 degrees.

Figure 25:
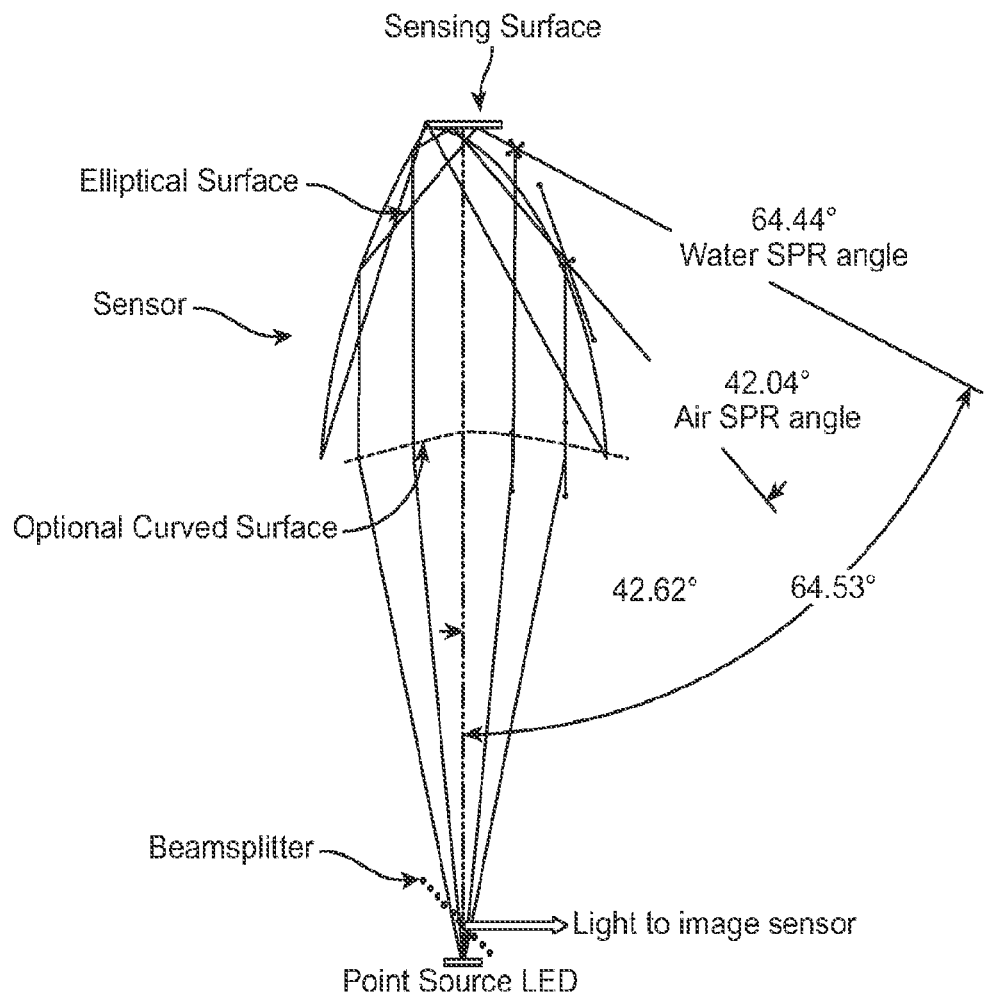
FIG. 25 is an illustration of another example of an injection molded sensor. The depicted sensor is configured to direct a first optical signal to interact with a sensing surface at an incident angle of 42.04 degrees, and to direct a second optical signal to interact with the sensing surface at an incident angle of 64.44 degrees.

FIG. 25 is another illustration of a sensor in accordance with embodiments of the invention. In the depicted embodiment, the sensor is configured to direct a first optical signal to interact with the sensing surface at an incident angle of about 42.04 degrees, and is configured to direct a second optical signal to interact with the sensing surface at an incident angle of about 64.44 degrees. Further indicated are: a gold coating on the sensing surface, an elliptical outer surface of the sensor, an optional curved lower surface of the sensor, a point source LED and a beam splitter.

Figure 42:
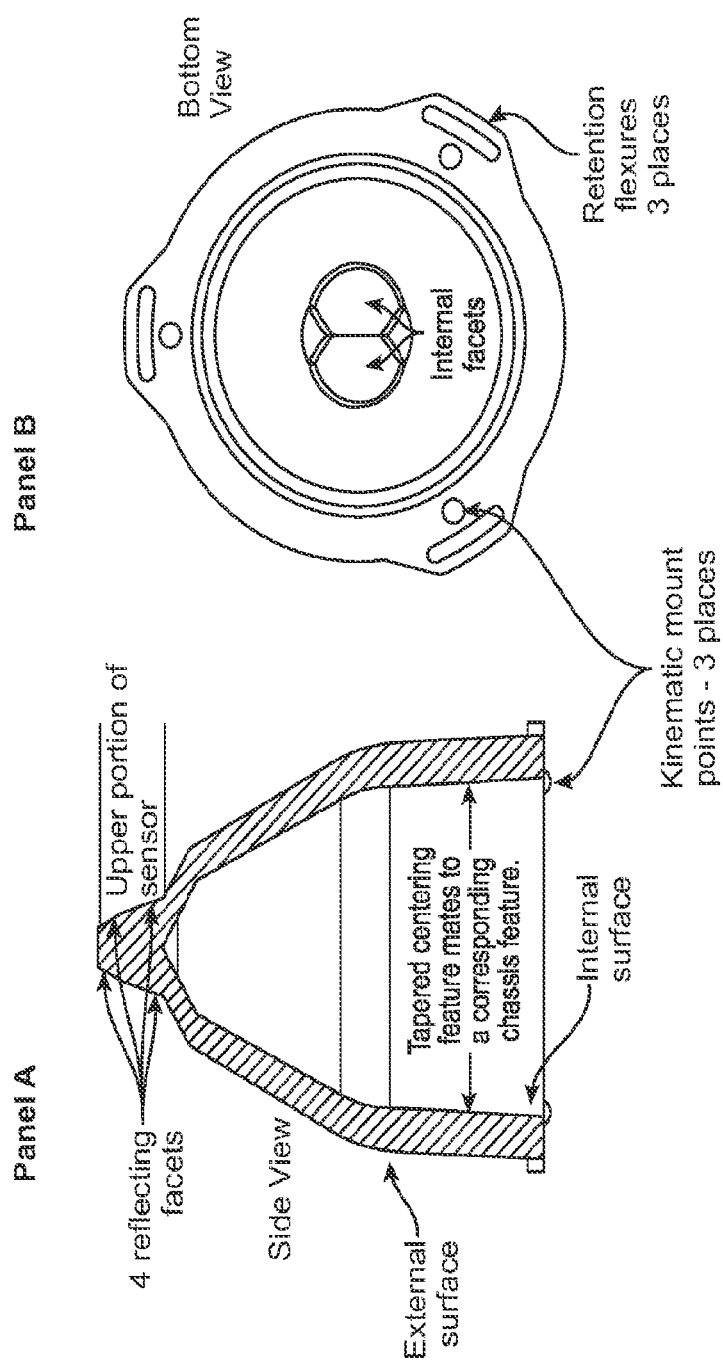
FIG. 42, Panel A is a side view illustration of a sensor. Panel B is a bottom view illustration of a sensor.

FIG. 42, Panel A is a side view of a sensor in accordance with embodiments of the invention having a frustoconical, concave shape with an internal surface and an external surface. In the depicted embodiment, an outer surface of the sensor has 4 reflecting facets and a tapered centering component that mates to an optical chassis. Panel B is a bottom view of the sensor, showing 2 facets on the internal surface of the sensor. Also depicted are retention components and kinematic mounting components.

Figure 43:
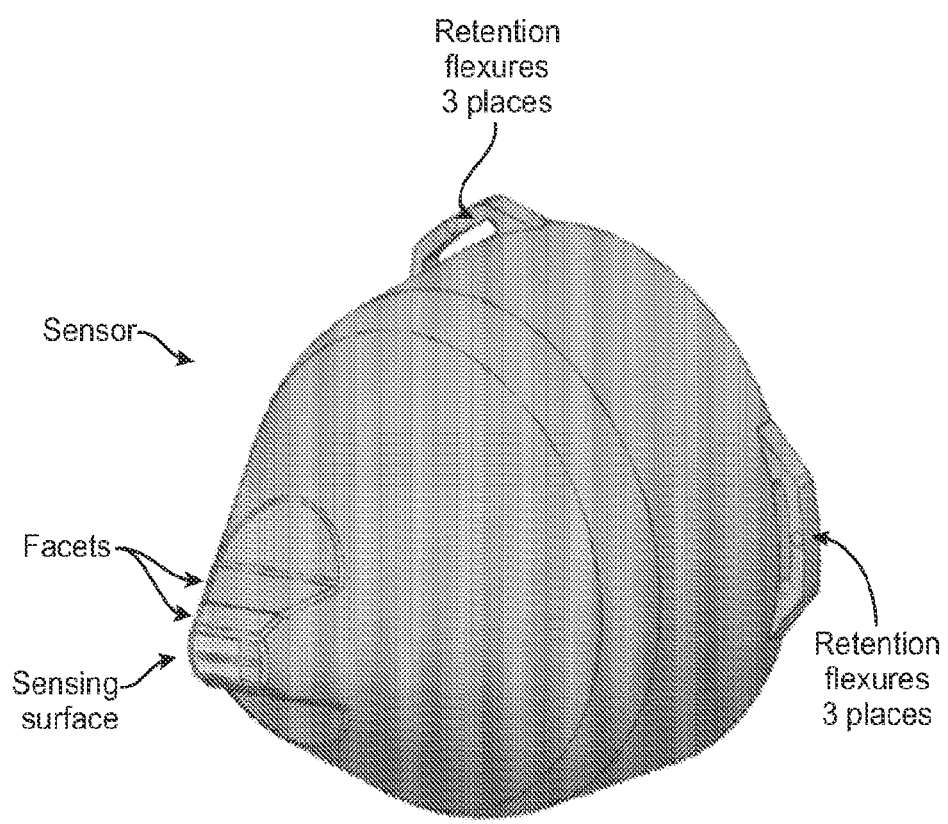
FIG. 43 is a perspective illustration of a sensor.

FIG. 43 is a perspective view of the sensor depicted in FIG. 42. A plurality of retention fixtures are visible, as well as the sensing surface and 4 reflecting facets on the external surface of the sensor.

Figure 44:
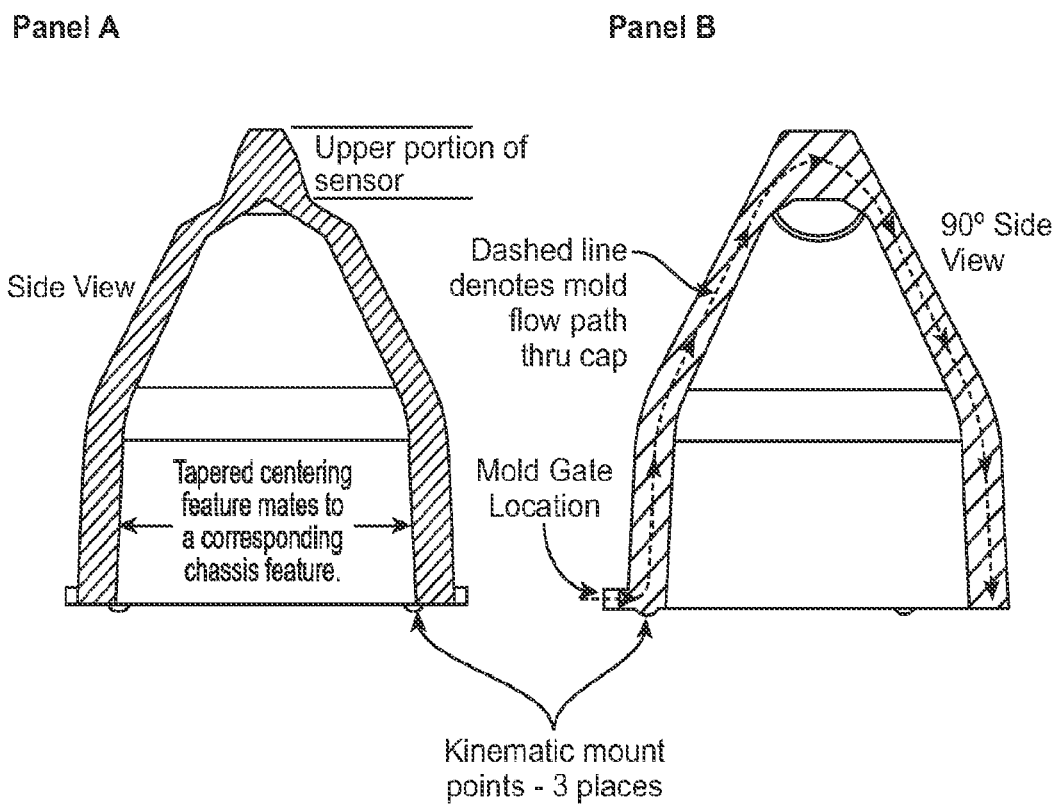
FIG. 44, Panels A and B show side view illustrations of a sensor.

FIG. 44, Panel A is a side view of a sensor in accordance with embodiments of the invention having a frustoconical, concave shape with an internal surface and an external surface. In the depicted embodiment, an outer surface of the sensor has 4 reflecting facets and a tapered centering component that mates to an optical chassis. Panel B is side view of a sensor, showing a dashed line that indicates the flow of material through a mold during the process of fabricating the sensor. Also depicted are kinematic mounting locations.

Figure 45:
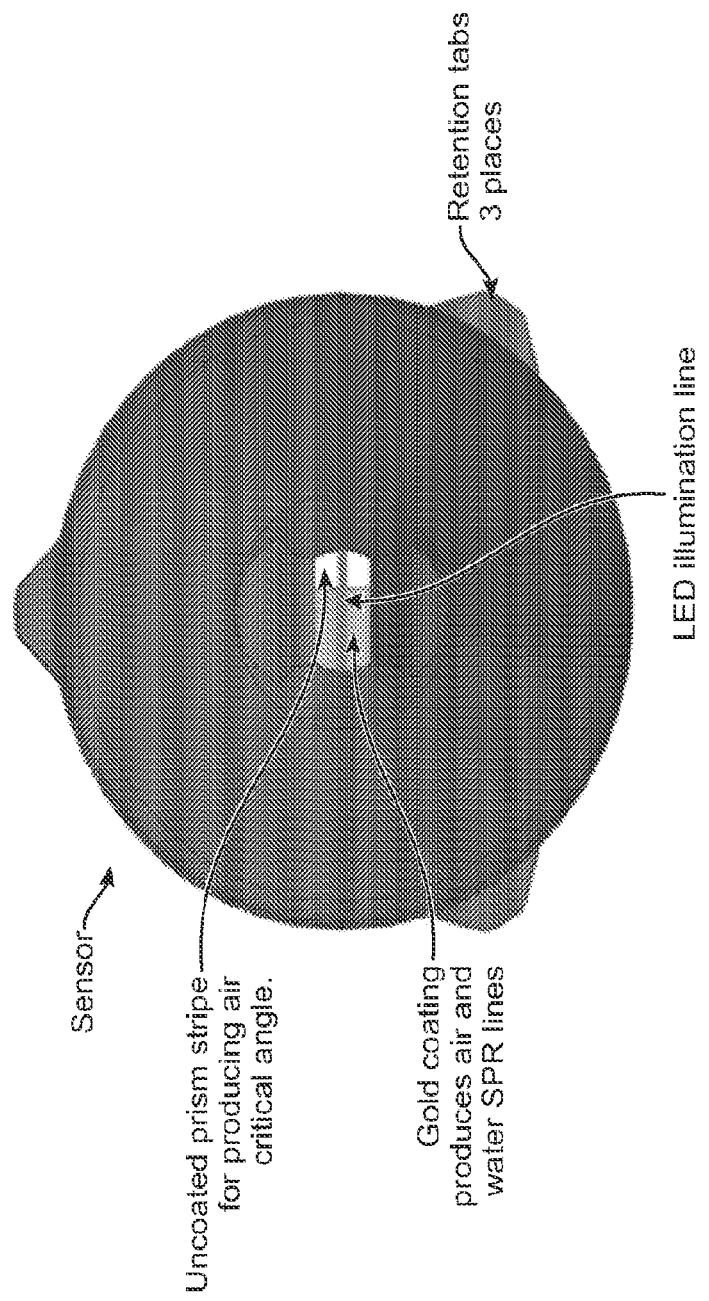
FIG. 45 is and end view illustration of a sensor.

FIG. 45 is a top, end view of a sensor in accordance with embodiments of the invention. The depicted sensor includes a sensing surface that comprises coated and non-coated regions. Also depicted are three retention components, or tabs, that are configured to removably couple the sensor to an optical chassis.

Figure 47:
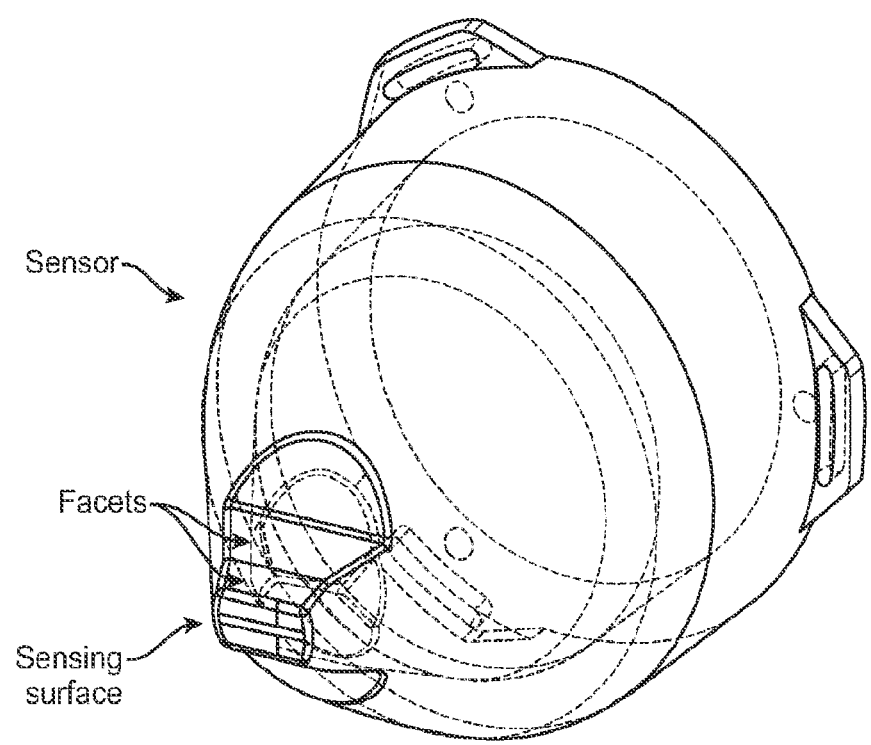
FIG. 47 is a transparent rendering of a sensor.

FIG. 47 is a transparent, perspective view of a sensor in accordance with embodiments of the invention.

Optical Chassis

As summarized above, aspects of the invention include an optical chassis that comprises an optical signal generating component and a detection component. In some embodiments, an optical chassis can comprise an optical signal manipulation component. Each of these aspects are described in greater detail below.

Aspects of the invention include one or more optical signal generating components that are configured to generate an optical signal. In some embodiments, an optical signal generating component can include an optical source that generates an optical signal, such as, e.g., a laser, a light emitting diode (LED), a point-source LED, or a white light source with a spectral filter. In some embodiments, an optical chassis can include a number of optical signal generating components ranging from 1 to 10, such as 2, 3, 4, 5, 6, 7, 8 or 9 optical signal generating components.

Optical signal generating components in accordance with embodiments of the invention can be configured to generate light having any suitable wavelength (e.g., may have any suitable emission spectrum), ranging from UV light, to visible light, to infrared light. In some embodiments, an optical signal can have a wavelength that ranges from about 300 nm to about 1,500 nm, such as about 325, 350, 375, 387, 393, 400, 425, 433, 445, 450, 467, 475, 488, 490, 492, 494, 495, 500, 502, 505, 510, 516, 517, 520, 525, 545, 550, 567, 573, 574, 575, 585, 596, 600, 603, 605, 611, 625, 633, 645, 650, 655, 667, 670, 673, 675, 690, 694, 700, 725, 750, 775, 800, 825, 850, 855, 875, 900, 925, 940, 950, 975, 1,000, 1,025, 1,033, 1,050, 1,060, 1,075, 1,100, 1,125, 1,150, 1,175, 1,200, 1,225, 1,250, 1,270, 1,275, 1,300, 1,325, 1,350, 1,375, 1,400, 1,425, 1,450, or 1,475 nm. In some embodiments, an optical signal can have a wavelength of about 855 nm. In some embodiments, an optical source can have a wavelength of about 950 nm.

Optical signal generating components in accordance with embodiments of the invention can be configured to generate optical signals in a variety of ways. For example, in some embodiments, an optical signal generating component is configured to generate an optical signal in a continuous manner. In some embodiments, one or more optical signal generating components can be configured to simultaneously generate optical signals having two different wavelengths. In some embodiments, an optical signal generating component is configured to generate flashing optical signals that can be measured in a gated manner. In some embodiments, an optical signal generating component is configured to generate an optical signal having a single wavelength. In some embodiments, an optical signal generating component is configured to generate a plurality of optical signals having different wavelengths, such that the same optical signal generating component can generate optical signals of two or more different wavelengths.

In some embodiments, an optical chassis comprises an opto-mechanical reference (OMR) component that is configured or adapted to place a physical obstruction in the path of one or more optical signals. The physical obstruction creates one or more reference signals that can be detected and analyzed by a detection component. In some embodiments, an OMR is configured to create a vertical or a horizontal obstruction within one or more optical signals, such that a vertical or horizontal shadow, or blocked region of the optical signal, can be detected by a detection component. In some embodiments, an OMR is configured to create a combination of vertical and horizontal obstructions within one or more optical signals, such that a combination of vertical and horizontal shadows, or blocked regions of the optical signal, can be detected by a detection component. In some embodiments, an opto-mechanical component is configured to create a circular or elliptical obstruction within one or more optical signals, such that a circular or elliptical shadow, or blocked region of the optical signal, can be detected by a detection component. Aspects of the subject methods involve detecting a pixel position of one or more features of an OMR signal, and using the pixel position of the one or more features of the OMR signal in a calibration, quality control, and/or data analysis procedure.

Aspects of the invention include a detection component that is configured to detect one or more optical signals from the subject sensors, and to generate data therefrom. In some embodiments, a detection component is configured to detect one or more optical signals from a subject sensor, and to generate an image (e.g., a digital image) of the data for analysis. In some embodiments, a detection component is configured to generate a plurality of images from one or more optical signals. In some embodiments, a detection component is configured to generate a plurality of images per second, such as 10, 20, 30, 40, 50, 60, 70, 80, 90, or a 100 or more images per second. In some embodiments, a detection component comprises a video recording component (e.g., a video camera) that is configured to generate a video of one or more optical signals that are received from a sensor. In some embodiments, a detection component is configured to capture one or more image frames of a video, and to subject the one or more image frames to further processing, as described further below. In certain embodiments, a detection component is configured to begin capturing data before a sample is contacted with the sensing surface of a subject sensor, and to rapidly capture data immediately following contact of the sample with the sensing surface. In some embodiments, a detection component is configured to begin capturing data concurrently with contact between the sample and the sensing surface, and to rapidly capture data immediately following contact of the sample with the sensing surface.

Detection components in accordance with embodiments of the invention are configured to receive an optical signal as an input, and to direct the optical signal to a detector for analysis. In some embodiments, a detection component may be configured to only allow light of a certain wavelength, or of a certain wavelength range, to enter the detection component. For example, in some embodiments, a detection component can include one or more optical filters that are configured to only allow light of a certain wavelength range to enter the detection component.

In some embodiments, a detection component can include one or more detectors comprising a photodiode. Photodiodes in accordance with embodiments of the invention are configured to absorb photons of light and convert the light into electrical current that can be measured. In some embodiments, a photodiode may include one or more optical filters, lenses, or any other suitable components that may be used to convert light energy into electrical current for measurement.

In some embodiments, a detection component can include one or more photomuplier tubes (PMTs). PMTs in accordance with embodiments of the invention are configured to detect incident photons by multiplying a current produced by an incident light signal.

In some embodiments, a detection component can include one or more avalanche photodiodes (APDs) or single photon avalanche diodes (SPADs), also known as Gieger-mode avalanche photodiodes, or G-APDs. APDs and SPADs in accordance with embodiments of the invention can detect optical signals (such as low intensity signals) down to the single photon level by exploiting a photon-triggered avalanche current in a semiconductor device to detect incident electromagnetic radiation.

In some embodiments, a detection component can include one or more streak cameras that operate by transforming a temporal profile of a light pulse into a spatial profile on a detector by causing a time-varying deflection of the light pulse across the detector.

In some embodiments, a detection component can include one or more detectors with an image sensor. Image sensors in accordance with embodiments of the invention are configured to convert an optical image into an electronic signal. Examples of image sensors include, but are not limited to, charge coupled devices (CCDs) and complementary metal-oxide semiconductor (CMOS) or N-type metal-oxide semiconductor devices. In some embodiments, an image sensor can be an active pixel sensor (APS).

In some embodiments, a detection component can include one or more cameras. In some embodiments, a camera is a CCD camera or a scientific CMOS camera (sCMOS) providing extremely low noise, rapid frame rates, wide dynamic range, high quantum efficiency (QE), high resolution, and a large field of view. Such cameras are commercially available from scientific technology vendors.

In some embodiments, a detection component can include one or more linear array sensors (LASs). Linear array sensors in accordance with embodiments of the invention comprise a linear array of integrating photosensing pixels, which are configured to measure incident light over a defined exposure time, and to generate a voltage or digital output that represents the light exposure of each pixel in the array. LASs are known in the art and are generally available in a variety of dimensions and pixel resolutions (DPI). In some embodiments, an analog output of an LAS can be directly interfaced to an analog-to-digital converter (ADC) to carry out digital signal processing.

In some embodiments, a detection component is configured to generate an image of one or more optical signals received from a subject sensor, and to convert or render the image into a digital image comprising a plurality of pixels that are organized on a coordinate system in an imaging array. In some embodiments, a digital image can have a two-dimensional coordinate system, e.g., an x,y coordinate system associated therewith, wherein each pixel in the digital image is assigned an x,y coordinate. In certain embodiments, a detection component can generate a gray-scale digital image, wherein each pixel in the digital image is assigned a gray-scale value corresponding to a range of gray shades from white to black. In some embodiments, a detection component can generate a color digital image, wherein each pixel in the digital image is assigned a color. In some embodiments, a number of pixels in the x direction of the imaging array ranges from about 500 to about 4,000 or more, such as about 1,000, 1,500, 2,000, 2,500, 3,000, or 3,500 or more. In some embodiments, a number of pixels in they direction of the imaging array ranges from about 500 to about 4,000 or more, such as about 1,000, 1,500, 2,000, 2,500, 3,000, or 3,500. Any detection component capable of generating an image from one or more signals that are received from a subject sensor can be used in accordance with the subject systems and methods.

Aspects of the subject systems include optical signal manipulation components that are configured to manipulate one or more characteristics of an optical signal. Examples of optical signal manipulation components include, but are not limited to, mirrors, lenses (e.g., cylindrical lenses, doublet lenses, collimating lenses), beam splitters, prisms (e.g., beam translating prisms), diffraction gratings, photomultiplier tubes, optical filters (e.g., optical filters that reduce external ambient light, such as, e.g., long pass filters, baffle components, and the like that can reduce or eliminate ambient light), beam shaping optics, optical waveguides, polarizers, spatial filters/spatial apertures, and the like. Optical signal manipulation components in accordance with embodiments of the invention can include any suitable number of individual components, including, in some embodiments, a plurality of the same individual component (e.g., a plurality of photomultiplier tubes, a plurality of polarizers, etc.).

In some embodiments, aspects of the subject systems include one or more spatial apertures. Spatial apertures (also known as spatial filters) in accordance with embodiments of the invention are components that are configured to remove aberrations in a light beam due to imperfections or variations in one or more optical components of the system. In some embodiments, a spatial aperture includes an aperture, or opening, that is placed in the optical path of an optical signal and allows a desired portion of the optical signal to pass through the aperture, while blocking light that corresponds to an undesired portion or structure of the optical signal. Spatial apertures in accordance with embodiments of the invention can include a small circular aperture, or "pinhole" aperture, that allows light to pass through. In some embodiments, a spatial aperture has an aperture whose diameter ranges from 50 μm to 500 μm, such as 100, 150, 200, 250, 300, 350, 400 or 450 μm. In certain embodiments, a spatial aperture may include an aperture whose size is variable, and the subject methods may include varying the size (e.g., varying the diameter) of the spatial aperture. In certain embodiments, a spatial aperture may include an aperture whose size can be varied from 50 μm to 500 such as 100, 150, 200, 250, 300, 350, 400 or 450 μm.

In certain embodiments, an optical signal manipulation component can be used to shape an optical signal from an optical source to create a collimated optical signal. In certain embodiments, one or more optical components may be used to shape an optical signal into a collimated optical signal. For example, in some embodiments, an optical collimating lens or a collection of lenses may be positioned in the path of an optical signal and used to shape the optical signal from the optical source into a collimated optical signal.

In some embodiments, an optical signal manipulation component can include one or more polarizers that are configured to polarize an optical signal. Polarization can be p-polarization (i.e., transverse magnetic (TM) polarization), or can be s-polarization (i.e., transverse electric (TE) polarization), or any combination thereof. In some embodiments, an optical signal manipulation component can include an elliptical polarizer and/or a circular polarizer that are configured to polarize an optical signal.

Aspects of the invention include a controller, processor and computer readable medium that are configured or adapted to control and/or operate one or more components of the subject systems or sensors. In some embodiments, a system includes a controller that is in communication with one or more components of the subject systems or sensors, as described herein, and is configured to control aspects of the systems and/or execute one or more operations or functions of the subject systems, e.g., to carry out one or more methods described herein. In some embodiments, a system includes a processor and a computer-readable medium, which may include memory media and/or storage media. Applications and/or operating systems embodied as computer-readable instructions (or "firmware", i.e., permanent software that is programmed into a read-only memory) on computer-readable memory can be executed by the processor to provide some or all of the functionalities described herein, including, by not limited to, carrying out one or more of the method steps described herein, acquiring and processing data obtained from the subject sensors and/or systems, and/or applying one or more algorithms or other manipulations to the data for analysis. In some embodiments, firmware can include instructions for executing one or more image capture sequences that capture one or more images of a medium that is placed in contact with a sensing surface. In some embodiments, a system can include software that has instructions for executing one or more algorithms that can be used for processing of one or more images, analyzing of data from one or more images (e.g., to determine an osmolarity of a test sample), or any combination thereof. In some embodiments, a system can be configured to carry out one or more methods automatically. For example, in some embodiments, a system can be configured to automatically execute one or more image capture sequences and/or image or data processing algorithms in response to a particular event, e.g., coupling of a sensor to an optical chassis, receipt of a user input (e.g., receipt of an activation signal from a user), etc.

In some embodiments, a system includes a user interface, such as a graphical user interface (GUI), and/or one or more user input devices that are adapted or configured to receive input from a user, and to execute one or more of the methods as described herein. In some embodiments, a GUI is configured to display data or information to a user.

In some embodiments, a system includes one or more temperature control elements that are configured to control the temperature of one or more portions of a sensor, and/or one or more components of an optical chassis. For example, in some embodiments, a system includes a temperature controller that is configured to maintain a sensor or an optical chassis within a target temperature range. Temperature control elements in accordance with embodiments of a system may include resistive heaters, thermoelectric heaters or coolers, fans, and the like.

In some embodiments, a system includes one or more environmental analysis components that are configured to measure one or more characteristics of an external environment. For example, in some embodiments, a system can include a temperature sensor (e.g., a thermometer or thermocouple) that can measure a temperature of the environment. In some embodiments, a system can include a pressure sensor (e.g., a barometer) that can measure a pressure (e.g., a barometric pressure) of the environment. In some embodiments, a system can include a humidity sensor (e.g., a hygrometer, a humidity sensor) that can measure a humidity of the external environment. In some embodiments, a system can include a light sensor that can measure the amount of light in an environment is which the sensor is operated. In some embodiments, a system can include an environmental composition sensor that can measure the composition of the environment (e.g., the presence and/or concentration of one or more chemical species) in which the sensor is operated. In certain aspects, the subject systems are configured to account for, or correct for, one or more characteristics of an external environment, or a combination of multiple external environment characteristics, when analyzing a sample. For example, in some embodiments, a processor is configured to correct for, e.g., an external temperature when analyzing a sample. In some embodiments, a processor is configured to correct for, e.g., a combination of humidity and environmental composition when analyzing a sample.

Aspects of the subject systems also include data exchange features, such as, e.g., USB ports, Ethernet ports, or other data ports that are configured to establish a connection that can be used to exchange/transmit data between two or more components of a system. Aspects of the subject systems also include wireless transmission components, such as WiFi components, that are configured to wirelessly transmit data between two or more components of a system. For example, in some embodiments, a system can transmit data obtained from a sensor to a database or repository for storage.

Aspects of the subject systems also include one or more computer processors, data storage, and/or database components that can be used to store and/or analyze data that is acquired by the subject systems. Such components can be physically connected to other components of the subject systems, such as, e.g., via a USB connection, or can be configured to wirelessly communicate with other components of the subject systems, e.g., via WiFi connection, or via the Internet. In some embodiments, computer processors, data storage and/or database components of the subject systems may be remotely located, e.g., may be located at a physical location that is different from the physical location of a sensor.

Aspects of the subject systems can also include one or more power components, such as batteries and/or power cables that are configured to provide electrical power to the subject systems. Power components in accordance with embodiments of the invention may be modular and may be configured to be removably coupled to the subject systems for purposes of providing power thereto, for example, one or more batteries or battery packs that are configured to be inserted into or otherwise coupled to the subject systems. In some embodiments, the subject systems include power cables that are configured to establish electrical contact with standard power outlets. In some embodiments, a system can include a base unit that is configured to re-charge one or more components of the system (e.g., an optical chassis, or a component thereof).

In some embodiments, a system can include one or more antisepticizing components that are configured to sanitize one or more components of a system. For example, in some embodiments, a system can include a UV light antisepticizing component that is configured to illuminate one or more portions of a system with UV light. In some embodiments, an antisepticising component can be disposed in a base unit that is configured to re-charge one or more components of a system, as described above.

In some embodiments, the various features of the subject systems are formed into a single device that includes a housing formed from suitable materials, such as plastic, metal, glass or ceramic materials, and any combinations thereof. For example, in some embodiments, a system that includes a sensor and an optical chassis, as described herein, is formed from a plastic housing, and various additional components of the system are located within the housing. In some embodiments, a system is formed into a single benchtop system that can be used to carry out the subject methods, as described further below. In some embodiments, a system is formed into a single, hand-held system that can be carried by a user. In certain embodiments, a hand-held system is wireless. In certain embodiments, a hand-held system includes a rechargeable battery component. In a preferred embodiment, the features of a system are formed into a wireless, rechargeable, pen-sized device that can be used to carry out the methods described herein.

In one preferred embodiment, an optical chassis includes four point source LEDs as optical signal generating components, wherein two of the point source LEDs are configured to emit light having a wavelength of about 855 nm, and two of the point source LEDs are configured to emit light having a wavelength of about 950 nm. In one preferred embodiment, an optical chassis includes a CMOS digital image sensor having about 2592×1944 active pixels, and that converts incident light into a digital electronic signal by determining an intensity value of light at each pixel and assigning a gray-scale value to each pixel.

Aspects of the invention include one or more signal processing components that are configured to analyze data obtained from a detection component. For example, in some embodiments, a signal processing component is configured to identify a region of interest (ROI) of an image that is generated by a detection component. In some embodiments, a signal processing component is configured to generate a mathematical function that corresponds to an average pixel intensity along a given coordinate direction of an image. For example, in some embodiments, a signal processing component is configured to calculate an average of a vertical column pixel intensity for each pixel position along the x coordinate of an image, and to generate a mathematical function representing the results. Once generated, the mathematical function can be analyzed to determine, e.g., an x coordinate that corresponds to a relative minimum or relative maximum value of the mathematical function.

In certain embodiments, a signal processing component is configured to apply one or more noise reduction techniques that serve to reduce or eliminate noise from a signal. For example, in some embodiments, a signal processing component is configured to apply a Gaussian blur algorithm to reduce noise in a signal. In some embodiments, a signal processing component is configured to use derivative signal processing to precisely locate a zero crossing value of a derivative signal.

In some embodiments, a signal processing component is configured to acquire and analyze a plurality of data from a sample over a time interval that ranges from about 0.001 seconds up to about 90 seconds, such as about 0.002 seconds, about 0.003 seconds, about 0.004 seconds, about 0.005 seconds, about 0.006 seconds, about 0.007 seconds, about 0.008 seconds, about 0.009 seconds, about 0.01 seconds, about 0.02 seconds, about 0.03 seconds, about 0.04 seconds, about 0.05 seconds, about 0.06 seconds, about 0.07 seconds, about 0.08 seconds, about 0.09 seconds, about 0.1 seconds, about 0.2 seconds, about 0.3 seconds, about 0.4 seconds, about 0.5 seconds, about 0.6 seconds, about 0.7 seconds, about 0.8 seconds, about 0.9 seconds, about 1 second, about 2 seconds, about 3 seconds, about 4 seconds, about 5 seconds, about 6 seconds, about 7 seconds, about 8 seconds, about 9 seconds, about 10 seconds, about 15 seconds, about 20 seconds, about 25 seconds, about 30 seconds, about 35 seconds, about 40 seconds, about 45 seconds, about 50 seconds, about 55 seconds, about 60 seconds, about 65 seconds, about 70 seconds, about 75 seconds, about 80 seconds, or about 85 seconds.

Figure 26:
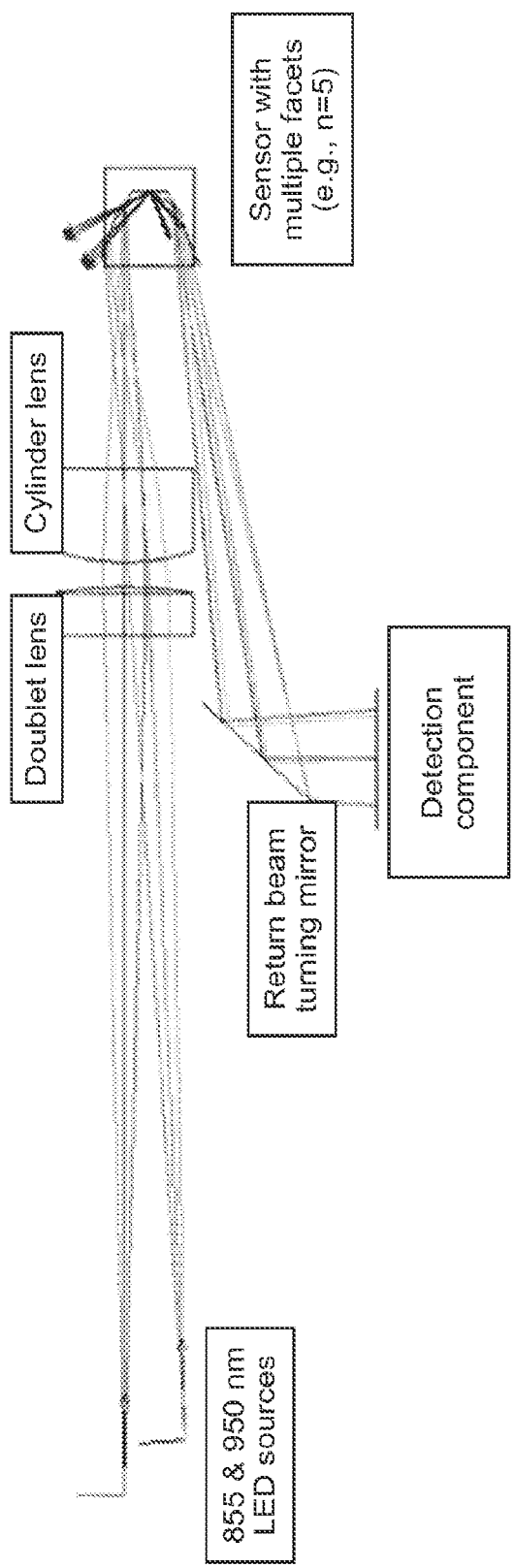
FIG. 26 is an illustration showing various light paths moving through a plurality of optical chassis components and a sensor.

Referring now to FIG. 26, an optical chassis and sensor in accordance with embodiments of the invention are depicted. In this illustration, various light paths originating at an LED and traveling through the system are depicted. The depicted embodiment includes 855 nm and 950 nm wavelength LED optical sources and a 5 facet sensor. In addition, the depicted optical chassis includes a doublet lens, a cylinder lens, a beam turning mirror and a detection component.

Figure 27:
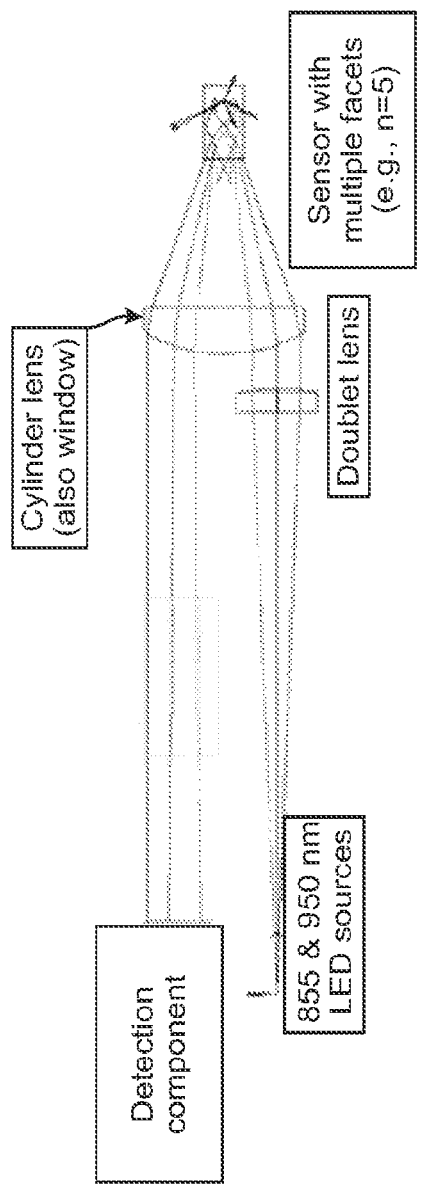
FIG. 27 is another illustration showing various light paths moving through a plurality of optical chassis components and a sensor.

FIG. 27 depicts another optical chassis and sensor in accordance with embodiments of the invention. In this illustration, various light paths originating at an LED and traveling through the system are depicted. The depicted embodiment includes 855 nm and 950 nm wavelength LED optical sources and a sensor. In addition, the depicted optical chassis includes a cylinder lens, a doublet lens and a detection component.

Figure 28:
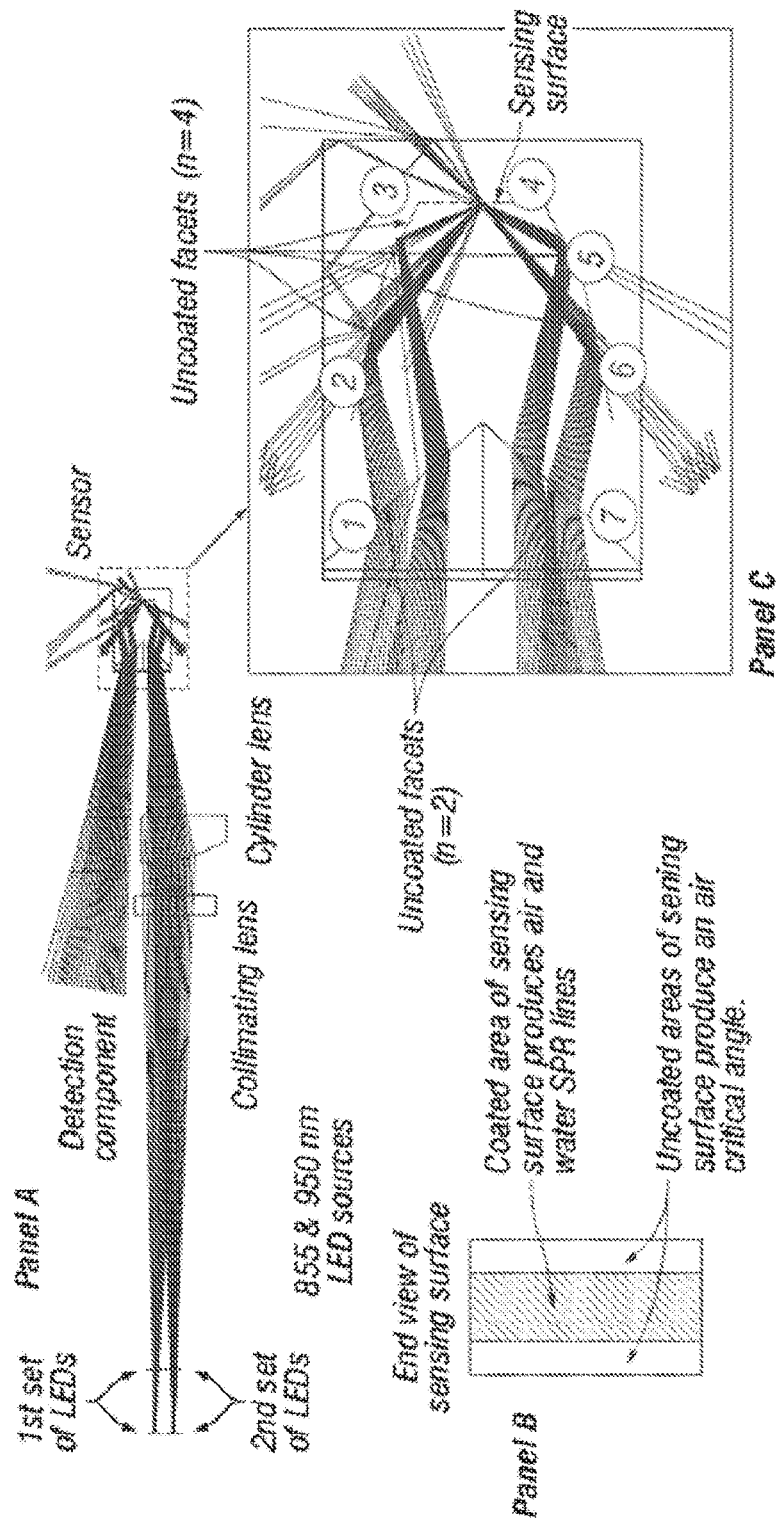
FIG. 28, Panel A is another illustration showing various light paths moving through a plurality of optical chassis components and a sensor. Panel B shows an end view of a sensing surface, showing a coated region and a non-coated region. Panel C is a close-up illustration of various light paths interacting with various facets and a sensing surface of a sensor.

FIG. 28, Panel A depicts another optical chassis and sensor in accordance with embodiments of the invention. In this illustration, two light paths originating at an LED and traveling through the system are depicted. The depicted embodiment includes 855 nm and 950 nm wavelength optical sources (each optical source comprising a set of two LEDs) and a sensor with a plurality of internal and external facets, as well as a sensing surface. In addition, the depicted optical chassis includes a cylinder lens, a collimating lens and detection component. Panel B shows a top, end view of the sensing surface of the depicted sensor. The sensing surface comprises a coated region with a gold coating (e.g., a gold semitransparent film coating) disposed in a rectangular orientation along the center line of the sensing surface. On either side of the coated region, the sensing surface comprises a non-coated region. Panel C shows a close up illustration of the sensor and its internal facets (n=2) (labeled with circled numerals 1 and 7), its external facets (n=4) (labeled with circled numerals 2, 3, 5 and 6), as well as the sensing surface (labeled with circled numeral 4).

Figure 32:
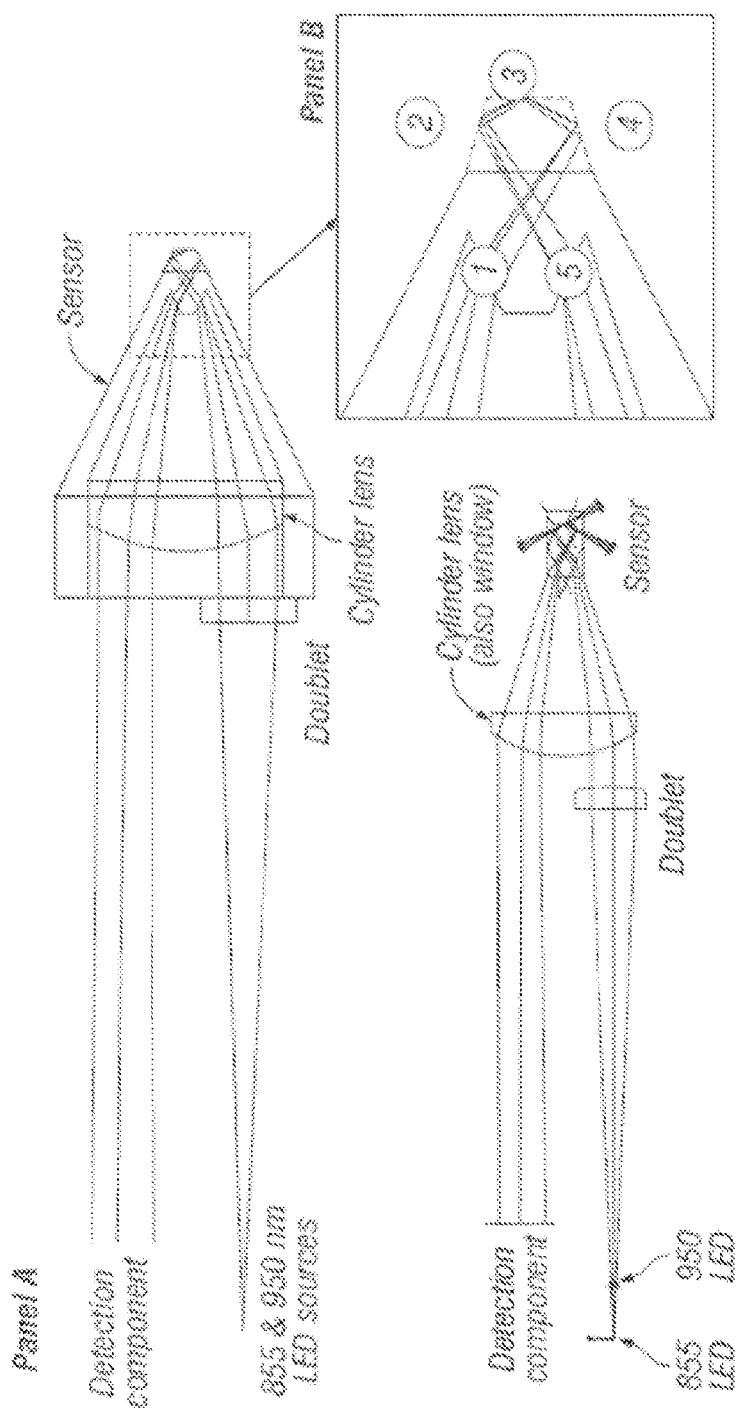
FIG. 32, Panel A is another illustration showing various light paths moving through a plurality of optical chassis components and a sensor. Panel B is a close-up illustration of various light paths interacting with various facets and a sensing surface of a sensor.

FIG. 32, Panel A depicts another optical chassis and sensor in accordance with embodiments of the invention. In this illustration, various light paths originating at an LED and traveling through the system are depicted. The depicted embodiment includes 855 nm and 950 nm wavelength LED optical sources and a sensor. In addition, the depicted optical chassis includes a cylinder lens, a doublet lens and a detection component. Panel B is a close up illustration of the internal facets of the sensor (n=2) (labeled with circled numerals 1 and 5), external facets of the sensor (n=2) (labeled with circled numerals 2 and 4), and a sensing surface, labeled with circled numeral 3. In the depicted embodiment, facet 2 is uncoated, facet 4 is coated with a reflective coating, and the sensing surface 3 is coated with a semitransparent film.

Figure 34:
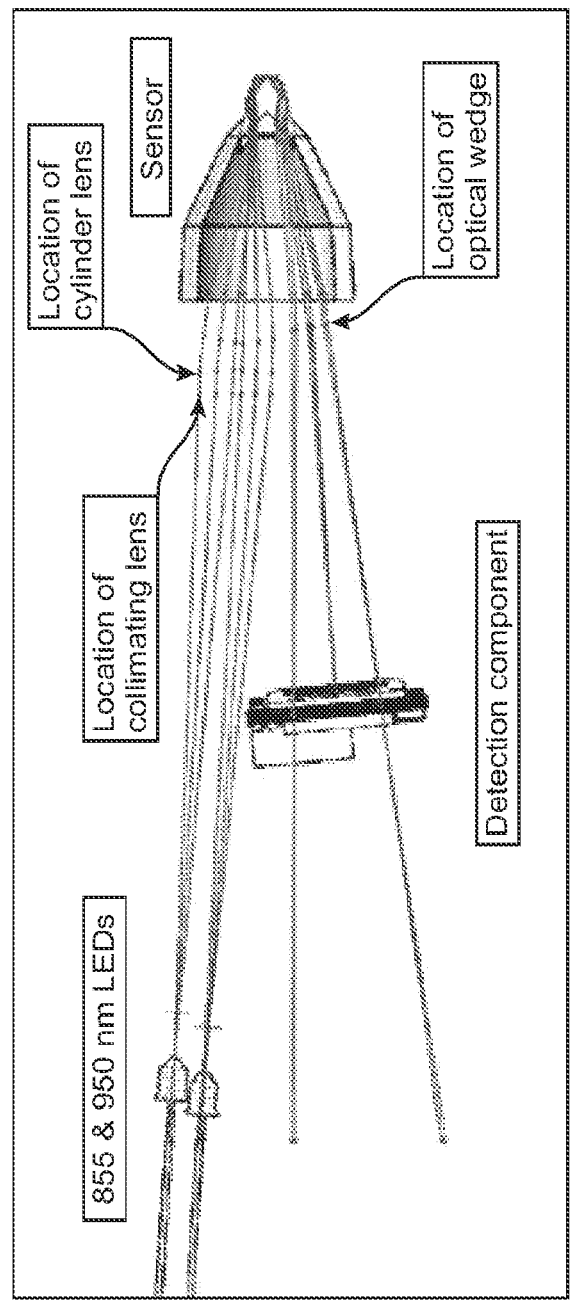
FIG. 34 is another illustration showing various light paths moving through a plurality of optical chassis components and a sensor.

FIG. 34 depicts another optical chassis and sensor in accordance with embodiments of the invention. In this illustration, various light paths originating at an LED and traveling through the system are depicted. The depicted embodiment includes 855 nm and 950 nm wavelength LED optical sources and a sensor. In addition, the illustration depicts the position of a cylinder lens, a collimating lens, an optical wedge, and a detection component (e.g., a XIMEA® imager).

Figure 35:
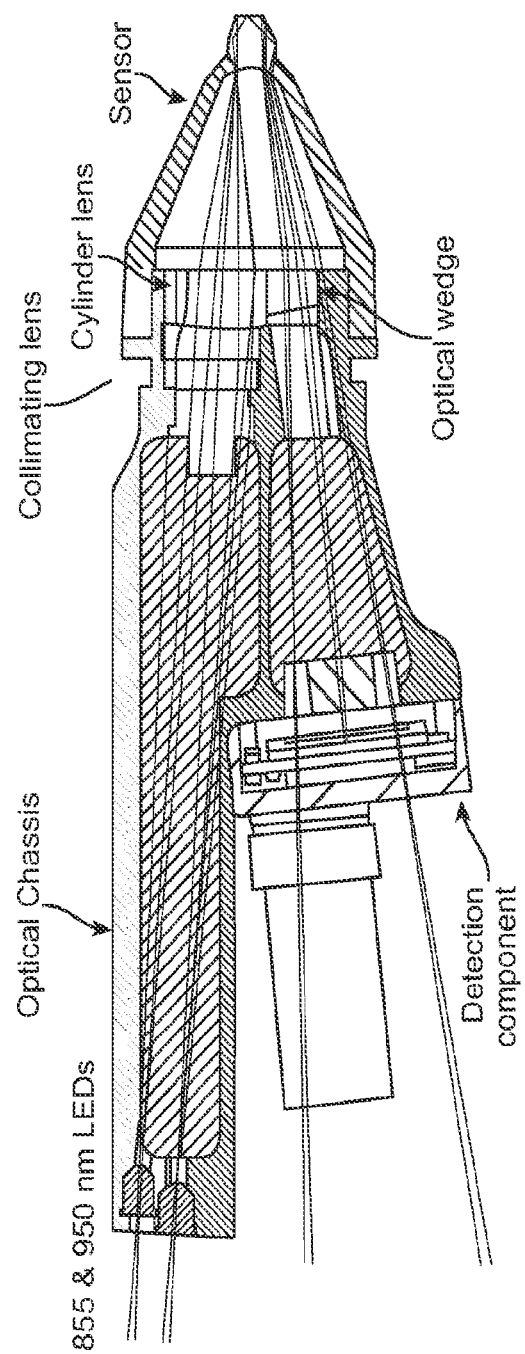
FIG. 35 is another illustration showing various light paths moving through a plurality of optical chassis components and a sensor.

FIG. 35 depicts a side view of an optical chassis and a sensor in accordance with embodiments of the invention. In this illustration, various light paths originating at an LED and traveling through the system are depicted. The depicted embodiment includes 855 nm and 950 nm wavelength LED optical sources and a sensor. In addition, the illustration depicts a cylinder lens, a collimating lens, an optical wedge, and a detection component (e.g., a XIMEA® imager). In this depicted embodiment, the sensor is operably coupled to the optical chassis.

Figure 36:
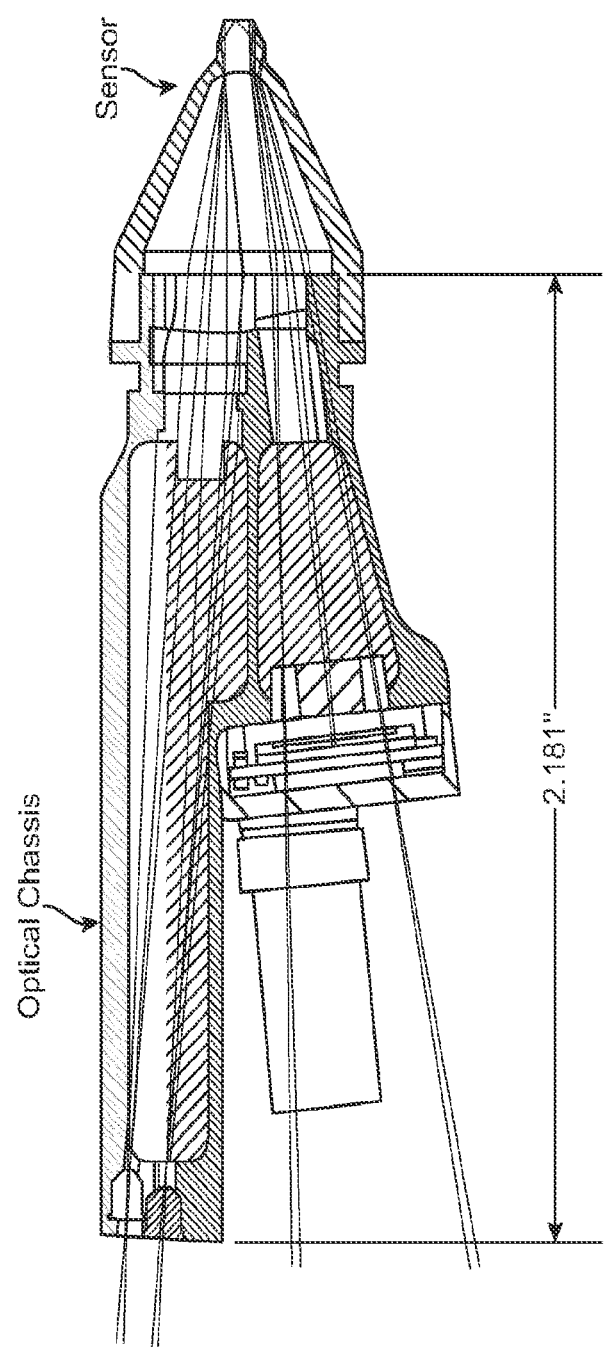
FIG. 36 is another illustration showing various light paths moving through a plurality of optical chassis components and a sensor. The overall length of the depicted optical chassis is 2.181 inches.

FIG. 36 depicts a side view of an optical chassis and a sensor in accordance with embodiments of the invention. In this depicted embodiment, the length of the optical chassis is approximately 2.181 inches.

Figure 37:
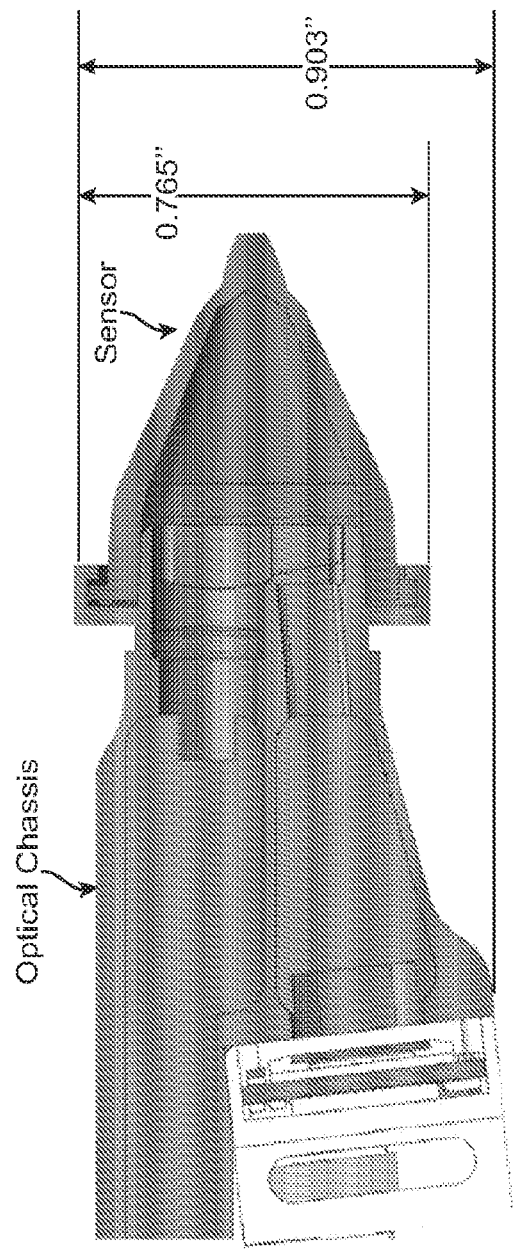
FIG. 37 is a side view illustration of an optical chassis and a sensor. The overall height of the depicted optical chassis is 0.903 inches. The diameter of the depicted sensor is 0.765 inches.

FIG. 37 depicts a side view of an optical chassis and a sensor in accordance with embodiments of the invention. In this depicted embodiment, the height of the optical chassis is approximately 0.903 inches, and the diameter of the sensor is approximately 0.765 inches.

Figure 38:
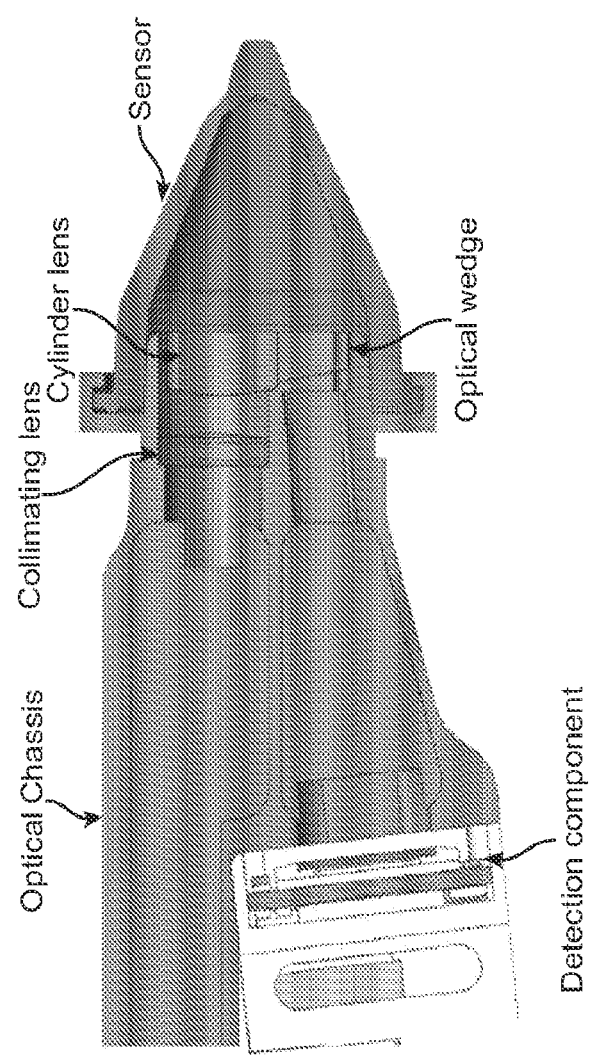
FIG. 38 is another side view illustration of an optical chassis and a sensor.

FIG. 38 depicts a side view of the optical chassis and a sensor that are depicted in FIG. 37. In the depicted embodiment, the optical chassis includes a collimating lens, a cylinder lens, an optical wedge and a detection component (e.g., a XIMEA® imager).

Figure 39:
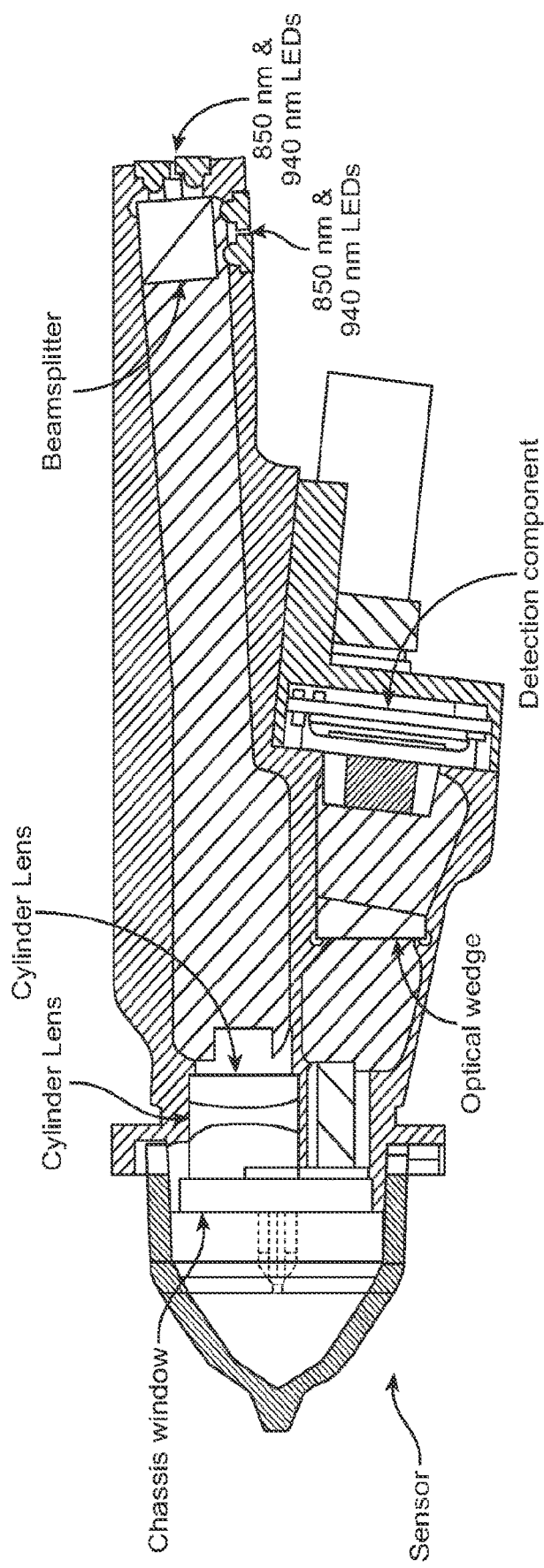
FIG. 39 is another side view illustration of an optical chassis and a sensor.

FIG. 39 depicts a side view of an optical chassis and a sensor in accordance with embodiments of the invention. In the depicted embodiment, the optical chassis includes a chassis window, two cylinder lenses, a beam splitter, 850 and 940 nm wavelength LEDs, an optical wedge, and a detection component (e.g., a XIMEA® imager).

Figure 40:
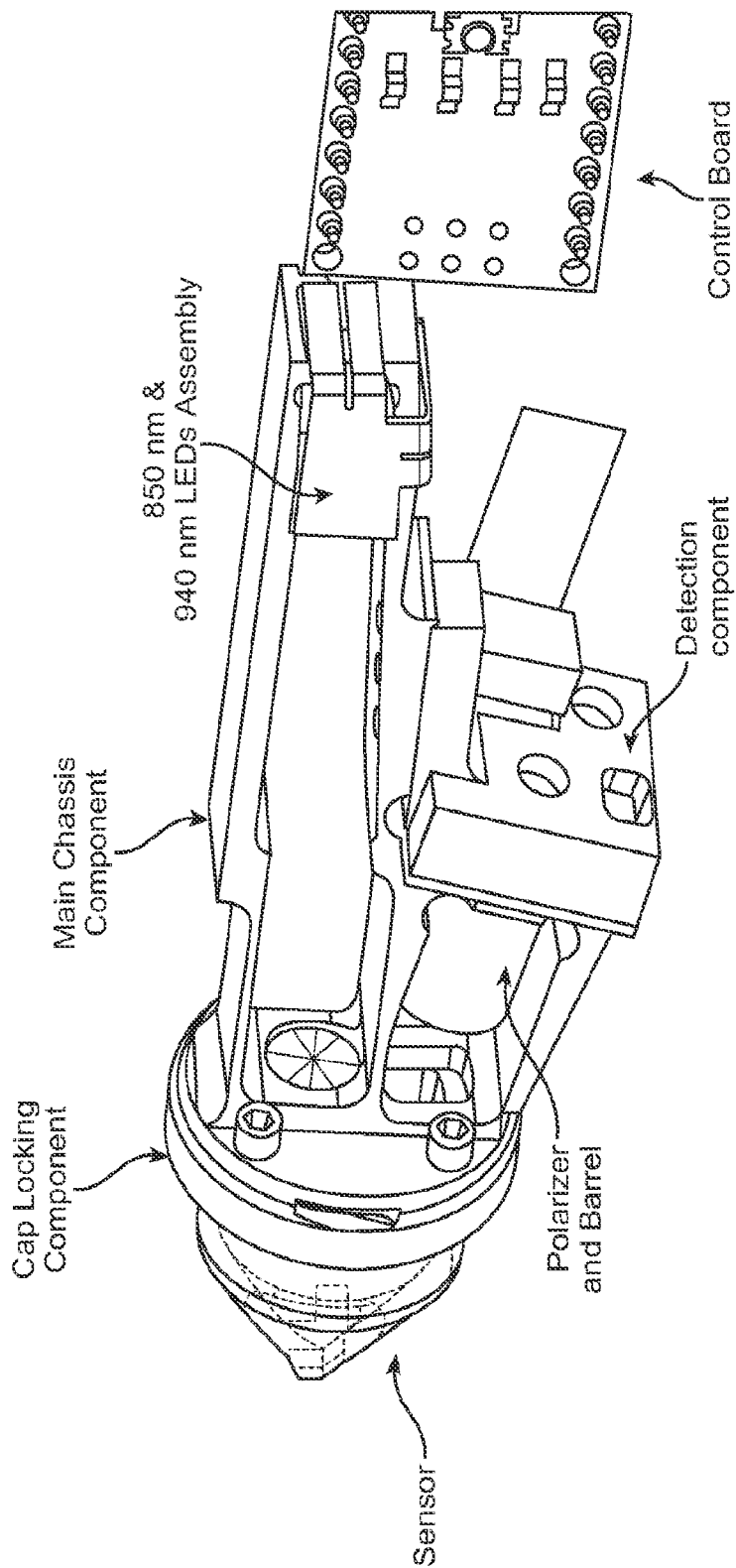
FIG. 40 is a perspective illustration of an optical chassis and a sensor.

FIG. 40 is a perspective illustration of an optical chassis and a sensor in accordance with embodiments of the invention. In the depicted embodiment, the optical chassis includes 850 and 940 nm wavelength LEDs, a sensor cap locking component, a polarizer and barrel, a control board, and a detection component (e.g., a XIMEA® imager assembly).

Figure 41:
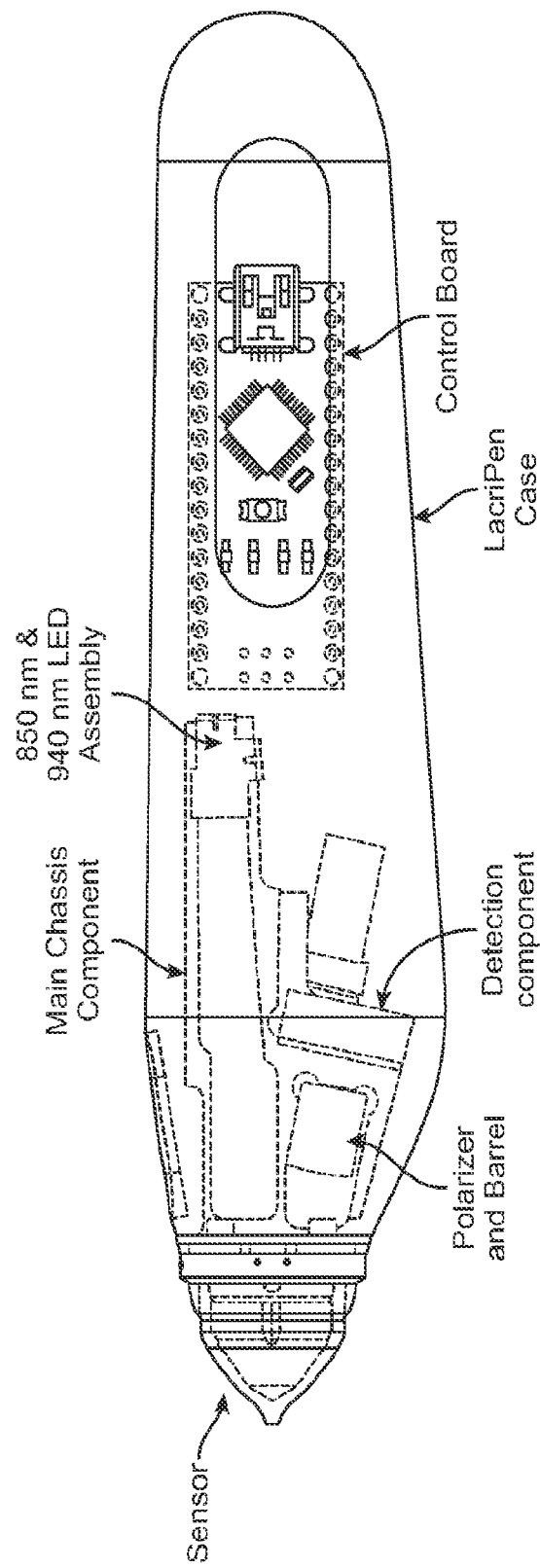
FIG. 41 is another side view illustration of an optical chassis and a sensor.

FIG. 41 is a side view of an optical chassis and a sensor in accordance with embodiments of the invention. In the depicted embodiment, the optical chassis includes 850 and 940 nm wavelength LEDs, a polarizer and barrel, a control board, a detection component (e.g., a XIMEA® imager assembly) and a case (LacriPen Case) that surrounds the optical chassis components.

Figure 46:
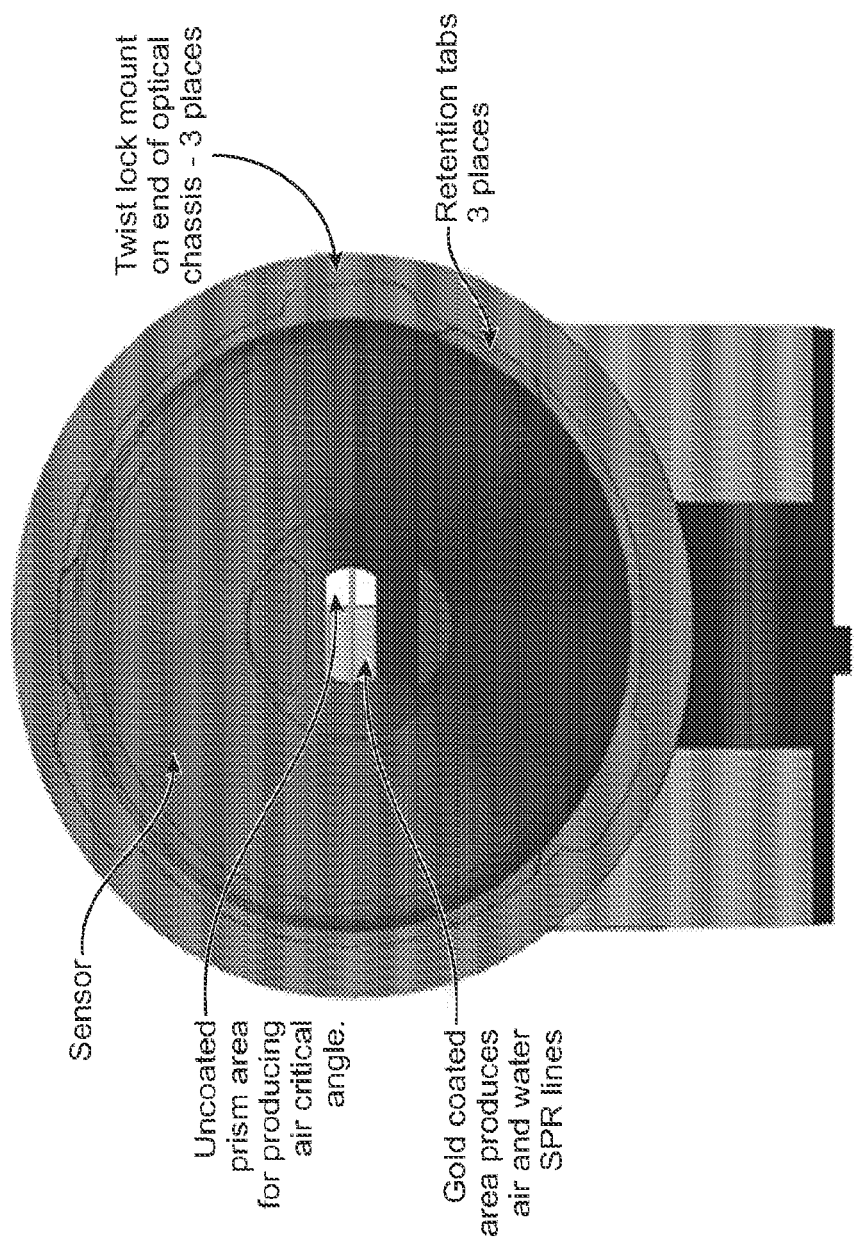
FIG. 46 is and end view illustration of a sensor and an optical chassis.

FIG. 46 is a top, end view of a sensor that is removably coupled to an optical chassis. In the depicted embodiment, the sensing surface of the sensor is shown, comprising a coated surface (gold coated area) and a non-coated surface (uncoated prism area). The depicted sensor also includes three retention components, or retention tabs, that are configured to removably couple the sensor to the optical chassis. The depicted sensor is configured to twist lock with the optical chassis.

Figure 48:
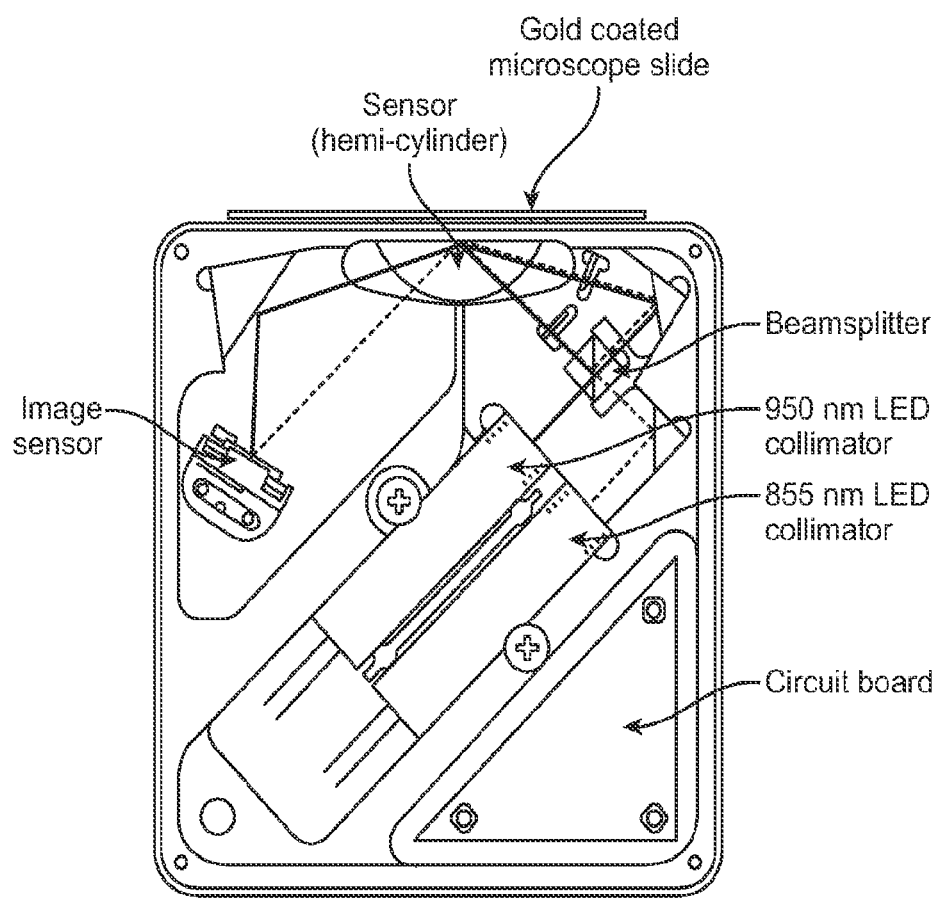
FIG. 48 is an illustration of a benchtop system comprising a sensor and an optical chassis comprising various components.

FIG. 48 is an illustration of a benchtop system in accordance with embodiments of the invention. In this depicted embodiment, the system includes a hemi-cylinder sensor, a gold coated microscope slide, an image sensor, a beam splitter, 950 and 855 nm wavelength LED optical sources and collimators, and a circuit board. The depicted embodiment is disposed in a square housing and is configured to be disposed on, e.g., a laboratory benchtop during use.

Figure 49:
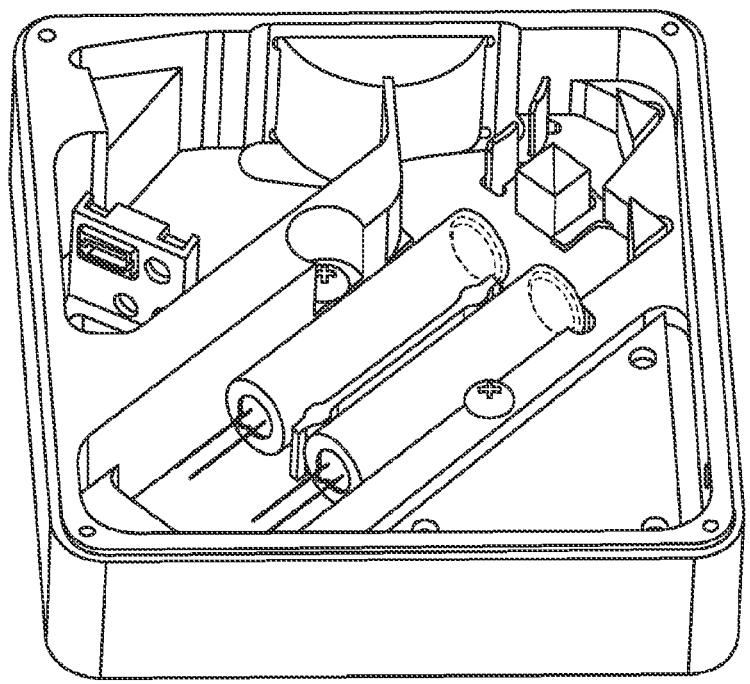
FIG. 49 is a perspective illustration of a benchtop system.

FIG. 49 is a perspective view of the benchtop system depicted in FIG. 48.

Figure 50:
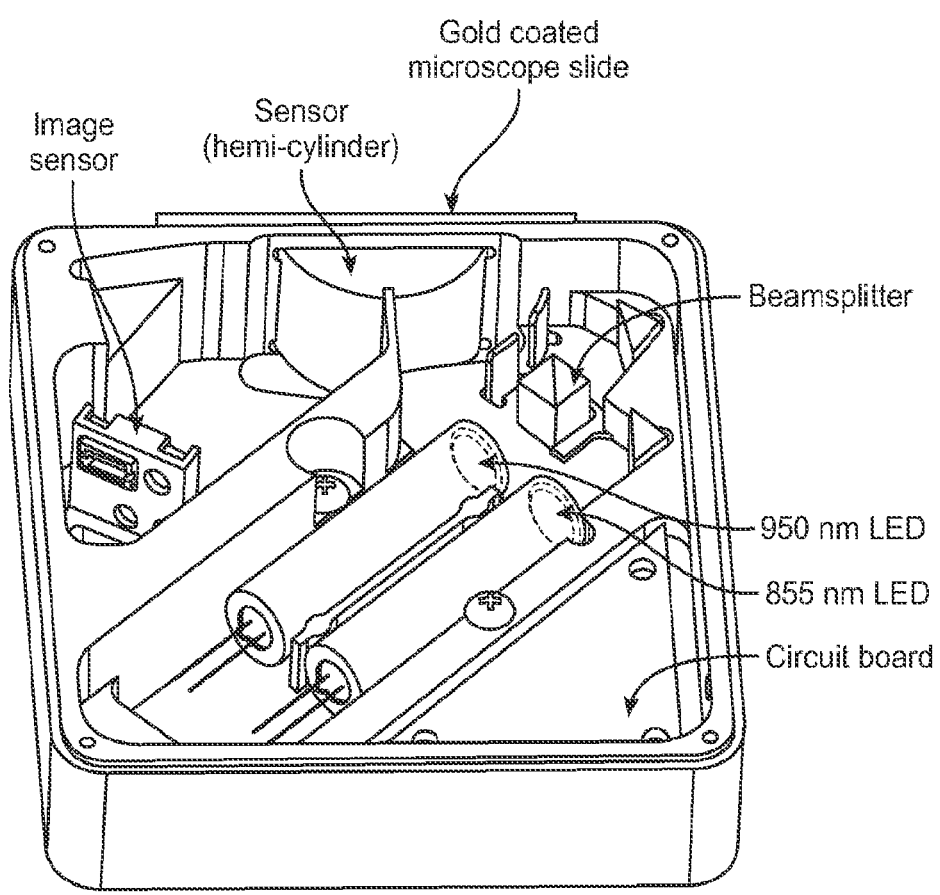
FIG. 50 is another perspective illustration of a benchtop system.

FIG. 50 is a labeled perspective view of the benchtop system depicted in FIGS. 48 and 49. The depicted embodiment shows a hemi-cylinder sensor, a gold coated microscope slide, an image sensor, a beam splitter, 950 and 855 nm wavelength LEDs, and a circuit board.

Figure 51:
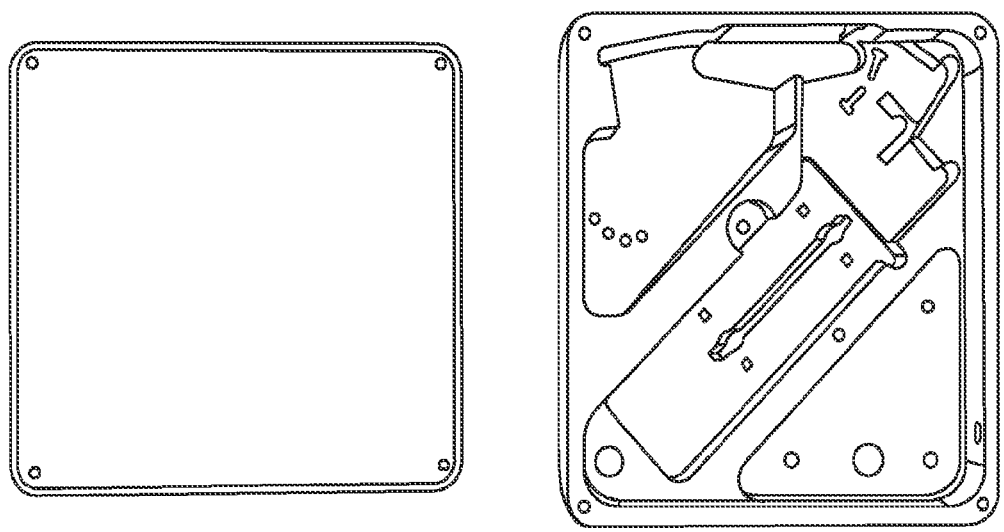
FIG. 51 is an image of an outer casing component that can be used in conjunction with a benchtop system as illustrated in FIGS. 48-50.

FIG. 51 is an image of a housing and an accompanying cover plate that can be used to house a benchtop system as described in FIGS. 48-50.

Methods of Use

Aspects of the invention include methods of analyzing a sample using the subject sensors and systems to determine, e.g., the osmolarity of the sample. As depicted in FIG. 1, the average osmolarity of tears in normal eyes differs from the average osmolarity of tears in dry eyes, and as such, can serve as a diagnostic predictor of dry eye disease. The subject methods involve contacting a sensing surface of a sensor with a medium to be tested (e.g., a reference medium, or a test sample having an unknown osmolarity) for a sufficient period of time to carry out one or more of the subject methods. In some embodiments, a subject method can be carried out in a time period that is about 90 seconds or less, such as 80 seconds, 70 seconds, 60 seconds, 50 seconds, 40 seconds, 30 seconds, 20 seconds, 10 seconds, 5 seconds, 4 seconds, 3 second, 2 second, or 1 second or less, such as 0.5 seconds, 0.4 seconds, 0.3 seconds, 0.2 seconds, or 0.1 seconds or less, such as about 0.09 seconds, 0.08 seconds, 0.07 seconds, 0.06 seconds, 0.05 seconds, 0.04 seconds, 0.03 seconds, 0.02 seconds, or 0.01 seconds or less, such as about 0.009 seconds, 0.008 seconds, 0.007 seconds, 0.006 seconds, 0.005 seconds, 0.004 seconds, 0.003 seconds, 0.002 seconds, or 0.001 seconds or less.

In some embodiments, the subject methods involve determining the osmolarity of a biological sample obtained from a patient or subject. The information can be used to assist a care giver in diagnosing the patient or subject with a condition or disorder (e.g., dry eye disease) based on the results of the analysis. For example, in some embodiments, if a tear film of a patient is determined to have an osmolarity or salinity value in a particular range, then the care giver can diagnose the patient with dry eye disease.

The subject methods can be used to determine the osmolarity of any suitable biological sample. Biological samples that can be analyzed using the subject methods include, without limitation: blood, plasma, serum, sputum, mucus, saliva, urine, feces, gastric and digestive fluid, tears, nasal lavage, semen, vaginal fluid, lymphatic fluid, interstitial fluids derived from tumorous tissue, ascites, cerebrospinal fluid, sweat, breast milk, synovial fluid, peritoneal fluid, and amniotic fluid.

Any suitable volume of sample can be used in conjunction with the subject methods. In some embodiments, the volume of a sample ranges from about 5 nanoliters (nL) up to about 1 milliliter (mL), such as about 25, 50, 75, or 100 nL, such as about 200, 300, 400, 500, 600, 700, 800, 900 or 1,000 nL, such as about 5, 25, 50, 75 or 100 microliters (µL), such as about 200, 300, 400, 500, 600, 700, 800, 900 or 1,000 µL. In some embodiments, a sensing surface of a sensor is contacted directly to a sample, e.g., is placed in direct contact with the sample. In some embodiments, a sensing surface of a sensor is contacted directly to a biological sample without having to physically separate the sample from the patient. For example, in some embodiments, a sensing surface is contacted directly to a tear fluid of a patient while the tear fluid remains in or on the patient's eye. In some embodiments, a sensing surface is contacted directly to a patient's blood (e.g., in an open wound) without physically separating the blood from the patient. In some embodiments, a sensing surface is contacted directly to a patient's saliva without physically removing the saliva from the patient's mouth.

Aspects of the methods involve contacting a sensing surface of a sensor with a sample (e.g., a biological sample) and directing an optical signal having a first wavelength to interact with the sensing surface at a first incident angle and over a first time interval to generate a signal (e.g., an SPR signal) in response. In some embodiments, the methods involve directing a second optical signal having a second wavelength to interact with the sensing surface at the first incident angle over a second time interval while the sensing surface is in contact with a sample. In some embodiments, the first and second time intervals are the same. In some embodiments, the first and second time intervals are different. In some embodiments, the first and second optical signals are directed to interact with the sensing surface concurrently, whereas in some embodiments, the first and second optical signals are directed to interact with the sensing surface in a gated manner.

Aspects of the methods further involve generating a series of images of the SPR signals over the time intervals, and determining a series of pixel positions that correspond to a minimum value of the SPR signals over the time intervals. In some embodiments, the pixel positions that correspond to the minimum value of the SPR signals over the time intervals are used to generate a mathematical function that plots the pixel position of the minimum value of the SPR signals versus time, referred to herein as an SPR function. In some embodiments, the methods involve comparing the SPR function to the pixel position of at least one reference feature to generate a reference-corrected SPR function. In certain embodiments, the methods involve comparing one or more characteristics of a first SPR function, which is generated from a first optical signal having a first wavelength, to one or more characteristics of a second SPR function, which is generated from a second optical signal having a second wavelength. In some embodiments, the characteristic of the function is a derivative of the function. In some embodiments, the characteristic of the function is a plateau value of the function.

Aspects of the methods involve contacting a sensing surface of a sensor with a reference medium and directing an optical signal having a first wavelength to interact with the sensing surface at a second incident angle to generate a signal (e.g., an SPR signal or a critical angle signal) in response. In some embodiments, the methods involve directing one or more optical signals having different wavelengths to interact with the sensing surface at the second incident angle while the sensing surface is in contact with the reference medium.

Aspects of the methods involve measuring critical angle signals as well as SPR signals that are generated from a sensing surface while the sensing surface is in contact with a reference medium. In some embodiments, an SPR signal is generated by directing an optical signal to interact with a coated region of a sensing surface. In some embodiments, a critical angle signal is generated by directing an optical signal to interact with a non-coated region of a sensing surface. In some embodiments, the methods involve directing first and second optical signals having different wavelengths to interact with a coated region of a sensing surface to generate first and second SPR signals. In some embodiments, the methods involve directing first and second optical signals having different wavelengths to interact with a non-coated region of a sensing surface to generate first and second critical angle signals.

In some embodiments, the methods involve first contacting a sensing surface of a sensor with a reference medium (e.g., air) and determining an SPR delta pixel value and/or a critical angle delta pixel value, as described above, and then contacting the sensing surface with a test sample (e.g., a biological sample), and determining the osmolarity of the test sample using one or data analysis procedures as described herein.

In some embodiments, the methods involve directing an optical signal to interact with a sensing surface at one or more incident angles. For example, in some embodiments, the methods involve directing a first optical signal to interact with a sensing surface at a first incident angle, and directing a second optical signal to interact with a sensing surface at a second incident angle. In some embodiments, the methods involve directing one or more optical signals to interact with a sensing surface at a different incident angle, depending on the type of medium that is in contact with the sensing surface. For example, in some embodiments, the methods involve contacting a sensing surface with a test sample (e.g., a biological sample) and directing one or more optical signals to interact with the sensing surface at a first incident angle, and contacting the sensing surface with a second medium (e.g., a reference medium) and directing one or more optical signals to interact with the sensing surface at a second incident angle. In some embodiments, the methods involve first contacting the sensing surface with a reference medium (e.g., air) to calibrate the sensor, verify one or more quality parameters of the sensor, or to obtain one or more reference values from the reference medium, and then contacting the sensing surface with a test sample (e.g., a biological sample, e.g., a tear fluid) and determining the osmolarity of the test sample.

In certain embodiments, the methods involve directing optical signals of different wavelengths to interact with a sensing surface. As reviewed above, the subject systems are configured to generate optical signals having any wavelength ranging from about 300 to about 1,500 nm. In some embodiments, the methods involve generating a first optical signal having a wavelength of about 855 nm, and generating a second optical signal having a wavelength of about 950 nm. In some embodiments, a plurality of optical signals can be directed to interact with a sensing surface simultaneously. For example, in some embodiments, two or more optical signals having different wavelengths are directed to interact with a sensing surface simultaneously. In some embodiments, a plurality of optical signals can be directed to interact with a sensing surface in a gated manner.

Aspects of the methods involve measuring changes in the intensity of one or more optical signals that are reflected from the sensing surface as a function of time while a test sample (e.g., a biological sample) is in contact with the sensing surface. Without being held to theory, the inventors have determined that as components of the sample (e.g., proteins within a biological sample) interact with the sensing surface (e.g., adsorb onto the sensing surface), the refractive index close to the sensing surface changes, altering the angle of the minimum reflected light intensity, or SPR angle. The change in the SPR angle, and/or the rate of change of the SPR angle, is proportional to the concentration and molecular weight of the components of the sample. The position of the minimum reflected light intensity, or minimum value of the SPR signal, can therefore be measured as a function of time, and the resulting data can be analyzed to determine one or more characteristics of the sample, such as the osmolarity of the sample, by comparison to a calibration data set.

Aspects of the methods involve signal processing of one or more signals that are received from a sensing surface (e.g., one or more SPR signals and/or critical angle signals). In some embodiments, a system includes signal processing capabilities that are configured to process a signal prior to analysis. For example, in some embodiments, the methods involve processing a signal to reduce noise prior to analysis. In some embodiments, the methods involve applying a Gaussian blur algorithm to a signal to reduce the amount of noise in the signal. In some embodiments, the methods involve applying low pass filtering to a signal to reduce the amount of noise in the signal.

Aspects of the methods involve detecting a signal using a detection component. In some embodiments, a detection component is configured to generate one or more images that are based on a signal received from a sensing surface. In some embodiments, a detection component is configured to generate a plurality of images from one or more signals that are received by an imaging component. For example, in some embodiments, a detection component is configured to generate a plurality of images per second once a sample (e.g., a reference medium or a test medium) has been placed in contact with a sensing surface of a sensor. In some embodiments, a detection component is configured to generate a plurality of images per second, such as 10, 20, 30, 40, 50, 60, 70, 80, 90, or a 100 or more images per second. In some embodiments, a detection component is configured to generate a video of one or more optical signals that are received from a sensor. In some embodiments, a detection component is configured to capture one or more image frames of a video, and to subject the one or more image frames to further processing, as described further below.

In some embodiments, a detection component has a field of view, and an image can be generated from a region of interest (ROI) within the field of view. In certain embodiments, the methods involve capturing data from a plurality of signals from a sensing surface in a single image frame. Capturing data from a plurality of signals in a single image frame provides an internal reference that can be used in the analysis of a sample.

Aspects of the methods involve data processing of an image that is generated from a detection component. In some embodiments, data processing involves applying a coordinate system (e.g., an x,y coordinate system) to an image. In some embodiments, each pixel, or a portion thereof, within a generated image can be assigned a specific x,y coordinate value. In some embodiments, each pixel within an image can be assigned a numerical value related to the intensity or color of light in the pixel. For example, in some embodiments, each pixel in an image is assigned a gray-scale value. In some embodiments, each pixel in an image is assigned a color value. In some embodiments, data processing involves performing a mathematical operation on a plurality of pixels. For example, in some embodiments, data processing involves calculating an average gray-scale value of a plurality of pixels. In some embodiments, data processing involves calculating an average gray-scale value of a column of pixels at a particular x coordinate on an image.

Aspects of the methods involve generating mathematical functions based on the data that is captured in an image using a detection component. For example, in some embodiments, the data from an image can be processed and transformed into a function that can be analyzed and manipulated mathematically using standard techniques. In some embodiments, an image is analyzed by determining the average gray-scale value of a column of pixels at each x coordinate, and the resulting data is converted into a function, or curve, that mathematically represents a signal from which the data was obtained. Once generated, the function can be analyzed or manipulated mathematically to determine its characteristics. In some embodiments, a plurality of pixel positions are plotted as a function of time to generate a time-based function representing, e.g., a change in the minimum value of an SPR signal as a function of time.

In some embodiments, a function can be analyzed to determine a minimum value or a maximum value using standard techniques. For example, in some embodiments, a first and/or second derivative of a function can be determined and used to calculate a relative minimum or relative maximum of the function. In some embodiments, a function can be smoothed using standard techniques, thereby reducing or diminishing noise in the data.

Aspects of the methods involve analyzing a function that is derived from an SPR signal in order to identify a pixel position corresponding to a minimum value of the function. The minimum value of the function corresponds to a reflectivity minimum of an SPR signal, and can be used in analyzing a sample (e.g., determining the osmolarity of a sample).

Aspects of the methods involve analyzing a function that is derived from a critical angle signal in order to identify a pixel position corresponding to a maximum value of the function. The pixel position corresponding to the maximum value of the function can be used to determine the critical angle of the sensor.

In some embodiments, aspects of the methods involve analyzing data that is obtained from a reference feature. In some embodiments, the reference feature is an opto-mechanical reference (OMR) feature, and the data that is obtained from the OMR is one or more pixel positions from a reference signal that is generated by the OMR. For example, in some embodiments, an OMR creates a reference signal that can be analyzed to determine one or more parameters of a sample. In certain embodiments, a reference signal created by an OMR can be used as a fixed reference signal against which changes in an SPR minimum value (e.g., the number of pixels by which the SPR minimum value is moved, or shifted) can be measured when a sensing surface of a sensor is contacted with a sample, or is contacted with a plurality of different samples (e.g., an air sample and a water sample, an air sample and a tear fluid sample, etc.). In certain embodiments, a reference signal created by an OMR can be used as a fixed reference signal that can be compared across different sample types (e.g., air and water, air and tear film, water and tear fluid, etc.). In some embodiments, a reference feature is a data value obtained from one or more SPR signals, or one or more critical angle signals. For example, in some embodiments, a sensing surface of a sensor is contacted with a reference medium, and one or more SPR signals are generated. A pixel position corresponding to a minimum value of the one or more SPR signals, or a comparison of such minimum values, can be used as a reference feature. In some embodiments, one or more critical angle signals are generated from a sensor, and a pixel position corresponding to a maximum value of the one or more critical angle signals, or a comparison of such maximum values, can be used as a reference feature.

Aspects of the methods involve comparing pixel positions corresponding to various features of the above-described mathematical functions. For example, in some embodiments, a method involves comparing a pixel position of a minimum value of a function derived from a first SPR signal to the pixel position of a minimum value of a function derived from a second SPR signal to determine an SPR delta pixel value. The SPR delta pixel value represents the distance between the minimum values of the first and second SPR signals. In some embodiments, the methods involve comparing a pixel position of a maximum value of a function derived from a first critical angle signal to the pixel position of a maximum value of a function derived from a second critical angle signal to determine a critical angle delta pixel value. The critical angle delta pixel value represents the distance between the maximum values of the first and second critical angle signals.

In some embodiments, the methods involve mathematically manipulating a delta pixel value to account for one or more external conditions that can impact the operation of a subject sensor. For example, in some embodiments, the methods involve multiplying or dividing a delta pixel value by a correction factor in order to account for an external condition. As reviewed above, in some embodiments, a subject system can include an environmental analysis component that can be used to measure one or more characteristics of the environment in which the sensor is operating.

In some embodiments, the methods involve verifying a quality parameter of a sensor. For example, in some embodiments, one or more characteristics of a signal that is generated by a sensor is evaluated to determine whether the sensor is of sufficient quality for use. In some embodiments, one or more characteristics of an SPR signal is evaluated to determine whether the sensor is of sufficient quality for use. In certain embodiments, a contrast value, shape, or dimension (e.g., height, width, or depth) of an SPR signal (or a data set or function derived therefrom) is evaluated to determine if the sensor is of sufficient quality for use. In some embodiments, one or more characteristics of a critical angle signal is evaluated to determine whether the sensor is of sufficient quality for use. In certain embodiments, a contrast value, shape, or dimension (e.g., height, width, or depth) of a critical angle signal (or a data set or function derived therefrom) is evaluated to determine if the sensor is of sufficient quality for use. In some embodiments, the methods can be used to verify whether a sensor has, e.g., a sufficient thickness of a semitransparent film and/or adhesion layer on the sensing surface, or a sufficient purity of a material in the semitransparent film and/or adhesion layer.

Aspects of the methods involve comparing one or more data values (e.g., one or more delta pixel values, one or more corrected delta pixel values) to a calibration data set in order to determine a characteristic of a sample (e.g., an osmolarity of a sample). In some embodiments, a system can include a plurality of calibration data sets that can be used for different purposes. In some embodiments, a system includes a calibration data set that includes osmolarity values as a function of delta pixel values, and the methods involve comparing a delta pixel value to the calibration data set to determine the osmolarity of a sample. In some embodiments, a system includes a calibration data set that includes quality parameter values, and the methods involve comparing one or more characteristics of a signal that is generated by a sensor to the calibration data set to determine whether the sensor is of sufficient quality for use. In some embodiments, a system includes a calibration data set that includes correction factors for various external environment parameters, and the methods involve comparing a measured external environment parameter to the calibration data set to determine an appropriate correction factor, and then mathematically manipulating a delta pixel value to apply the correction factor.

In some embodiments, a method involves operably connecting a sensor to an optical chassis. In certain embodiments, a method involves removably coupling a sensor to an optical chassis, carrying out an analysis method, as described herein, and then removing the sensor from the optical chassis. In some embodiments, the methods involve aseptically coupling a sensor to an optical chassis. In some embodiments, the methods involve aseptically de-coupling a sensor from an optical chassis.

Aspects of the methods involve the analysis of any suitable sample. In some embodiments, a sample is a gaseous or a liquid medium. In certain embodiments, a medium can be a calibration medium, having a known osmolarity value. For example, in some embodiments, the methods involve contacting a sensor with a medium having a known osmolarity, directing one or more optical signals to interact with the sensing surface, and detecting one or more signals resulting therefrom (e.g., detecting an SPR signal or a critical angle signal). In some embodiments, a sample can be a reference medium (e.g., a medium against which a test medium or sample will be compared). In some embodiments, a reference medium can be air (e.g., the air in a room where the sensor is used). In some embodiments, a sample is a liquid medium, e.g., water. In some embodiments, a sample can be a biological sample, as described above. In some embodiments, the methods involve contacting a sensing surface of a sensor with a sample, and maintaining contact between the sample and the sensing surface while at least some of the method steps are carried out.

In a preferred embodiment, a method involves contacting a sensing surface of a sensor with a tear fluid from a subject. A first optical signal having a wavelength of about 855 nm is directed to interact with the sensing surface at an incident angle of about 64 degrees to generate a first SPR signal over a first time interval. The first SPR signal is detected over the first time interval with the detection component. A plurality of images of the signal are recorded over the first time interval, and the pixel position corresponding to the minimum value of the SPR signal is plotted as a function of time to generate a first time-based SPR function.

Next, a second optical signal having a wavelength of about 950 nm is directed to interact with the sensing surface at the same incident angle of about 64 degrees to generate a second SPR signal over a second time interval. The second SPR signal is detected over the second time interval with the detection component. A plurality of images of the signal are recorded over the second time interval, and the pixel position corresponding to the minimum value of the second SPR signal is plotted as a function of time to generate a second time-based SPR function.

Next, the first and second time-based SPR functions are compared to at least one reference feature to a generate a first and a second reference-corrected SPR function. One or more characteristics of the first and second reference-corrected SPR functions are then analyzed to determine the osmolarity of the tear fluid. In some embodiments, the reference feature comprises a pixel position of one or more OMR features.

In one preferred embodiment, the methods further comprise contacting the sensing surface of a sensor with air as a reference medium and directing a first optical signal having a wavelength of about 855 nm to interact with the sensing surface at an incident angle of about 42 degrees to generate a third SPR signal. The third SPR signal is detected with a detection component that generates an image from the signal. The image of the signal is processed to generate a mathematical function that represents the third SPR signal, and which does not substantially vary with respect to time. The pixel position corresponding to the minimum value of the function is determined.

Next, a second optical signal having a wavelength of about 950 nm is directed to interact with the sensing surface at the same incident angle of about 42 degrees to generate a fourth SPR signal. The fourth SPR signal is detected with a detection component that generates an image from the signal. The image of the signal is processed to generate a mathematical function that represents the fourth SPR signal, and which does not substantially vary with respect to time. The pixel position corresponding to the minimum value of the function is determined.

The pixel positions corresponding to the minimum values of the third and fourth SPR signals are then compared to determine an SPR delta pixel value. In some embodiments, the pixel position corresponding to the minimum value of the third or fourth SPR signal is used as a reference feature that the first and a second reference-corrected SPR functions are compared to. In some embodiments, the SPR delta pixel value is used as a reference feature that the first and a second reference-corrected SPR functions are compared to. In some embodiments, a combination of the pixel positions of the minimum values of the third and/or fourth SPR signals, and/or the SPR delta pixel value, is used as a reference feature that the first and a second reference-corrected SPR functions are compared to.

In one preferred embodiment, the methods further comprise contacting the sensing surface of a sensor with air as a reference medium and directing a first optical signal having a wavelength of about 855 nm to interact with the sensing surface at an incident angle of about 42 degrees to generate a first critical angle signal. The first critical angle signal is detected with a detection component that generates an image from the signal. The image of the signal is processed to generate a mathematical function that represents the first critical signal, and which does not substantially vary with respect to time. The pixel position corresponding to the maximum value of the function is determined.

Next, a second optical signal having a wavelength of about 950 nm is directed to interact with the sensing surface at the same incident angle of about 42 degrees to generate a second critical angle signal. The second critical angle signal is detected with a detection component that generates an image from the signal. The image of the signal is processed to generate a mathematical function that represents the second critical angle signal, and which does not substantially vary with respect to time. The pixel position corresponding to the maximum value of the function is determined.

The pixel positions corresponding to the maximum values of the first and second critical angle signals are then compared to determine a critical angle delta pixel value. In some embodiments, the pixel position corresponding to the maximum value of the first or second critical angle signal is used as a reference feature that the first and a second reference-corrected SPR functions are compared to. In some embodiments, the critical angle delta pixel value is used as a reference feature that the first and a second reference-corrected SPR functions are compared to. In some embodiments, a combination of the pixel positions of the maximum values of the first and/or second critical angle signals, and/or the critical angle delta pixel value, is used as a reference feature that the first and a second reference-corrected SPR functions are compared to.

Figure 52:
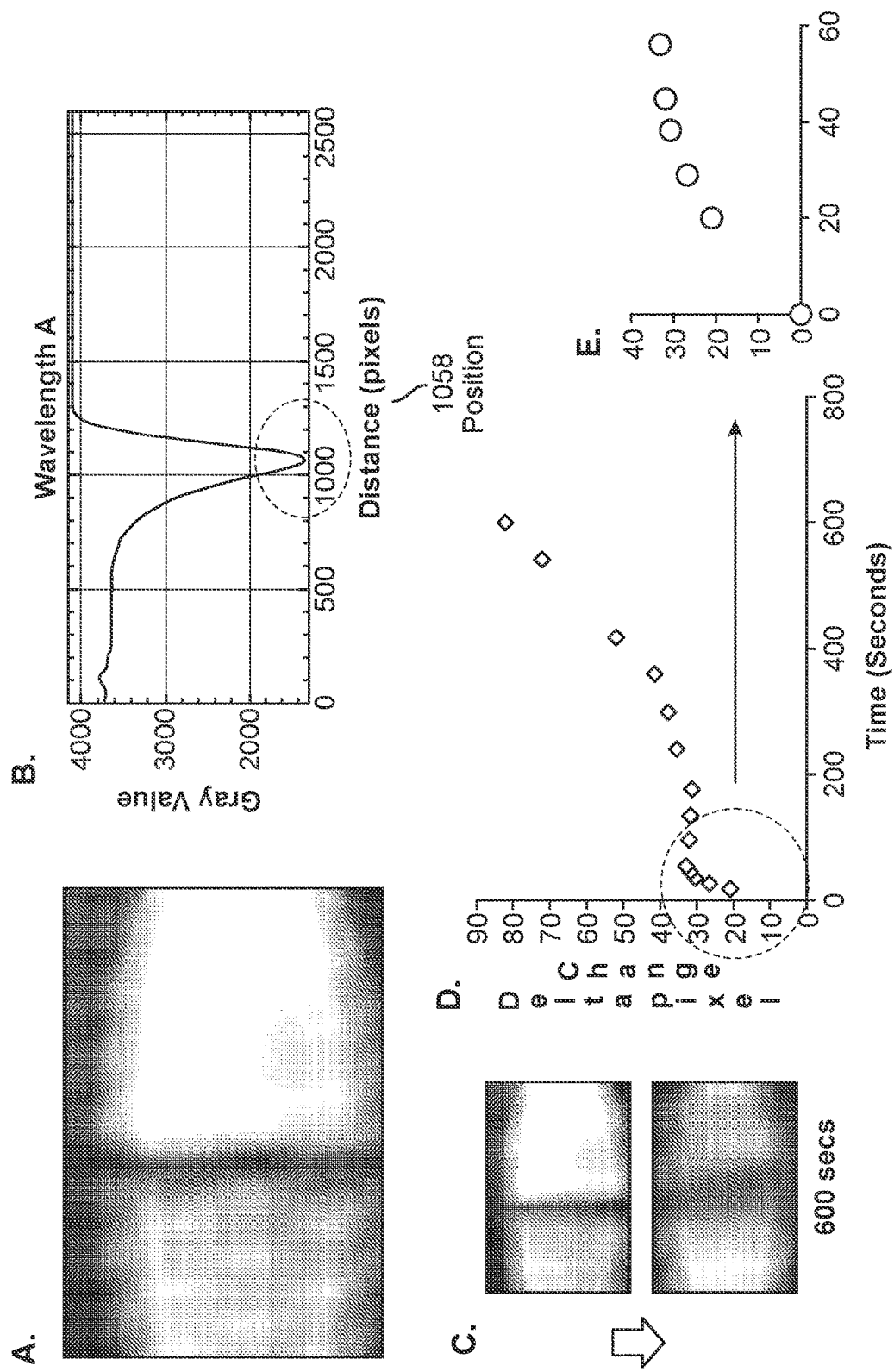
FIG. 52, Panels A-E show images and graphs of SPR signals collected over different time intervals using the methods described herein.

Turning now to FIG. 52, Panel A is an image of an SPR signal acquired with air as the reference medium in contact with the sensing surface of the sensor. Panel B is a graph of grey value as a function of pixel position for the optical signal shown in Panel A. Panel C provides two images of an SPR signal acquired at two different times, t=0 and t=600 seconds. Panel D is a graph showing the pixel position of the minimum value of the SPR signal shown in Panel C as a function of time after the sensing surface was contacted with a biological sample (e.g., a tear fluid). Panel E is a graph showing a close-up view of the pixel position of the minimum value of the SPR signal shown in Panel D over a time interval of 60 seconds and obtained using an optical signal having a wavelength of 855 nm, and corrected by subtracting the pixel position at t=0 seconds from the pixel position of the minimum value of the SPR signal measured at each indicated time point.

Figure 53:
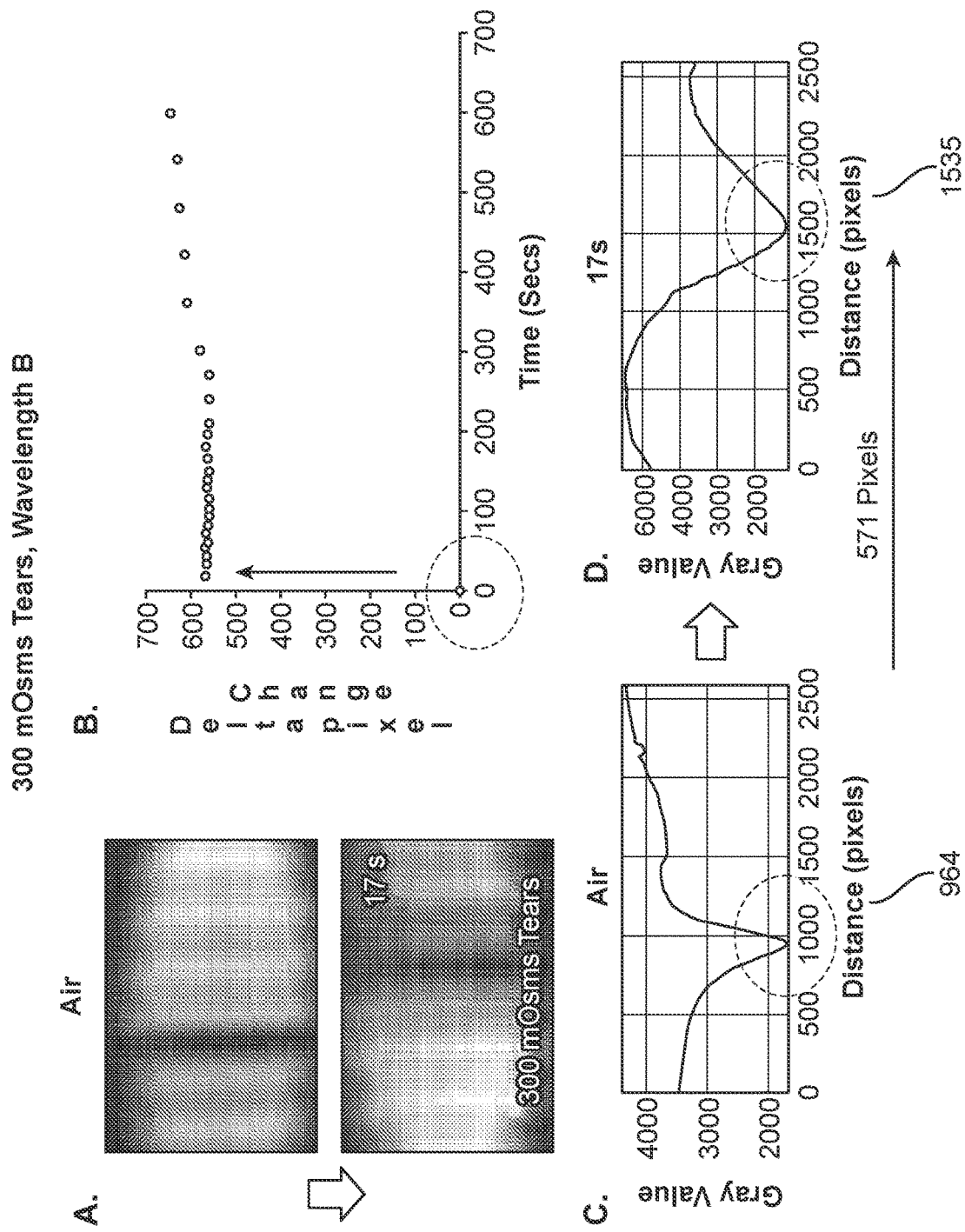
FIG. 53 Panels A-D show images and graphs of SPR signals collected over different time intervals using the methods described herein.

FIG. 53 shows a plurality of data from air and from a sample of tear fluid having an osmolarity of 300 mOsm/L. Panel A, top, shows an image of an SPR signal acquired with air as the reference medium in contact with the sensing surface. Panel A, bottom, shows an image of an SR signal acquired with the tear fluid in contact with the sensing surface for 17 seconds. The shift to the right of the vertical black line, which represents the minimum value of the SPR signal, can be seen. Panel B is a graph showing the change in delta pixel value for the sample of as a function of time following contact of the sensing surface with the tear fluid. The delta pixel value changed rapidly, following contact of the sensing surface with the tear solution. Panel C is a graph showing grey value as a function of pixel position for the air SPR signal. The pixel position corresponding to the minimum value of the SPR signal is circled. Panel D is a graph showing grey value as a function of pixel position for the tear fluid SPR signal taken 17 seconds after the tear fluid was contacted with the sensing surface. The change in delta pixel value between the circle positions in Panel C and Panel D is approximately 571 pixels. This change in pixel position can be used as a data point in a calibration data set for determining the osmolarity of tear fluid.

Figure 54:
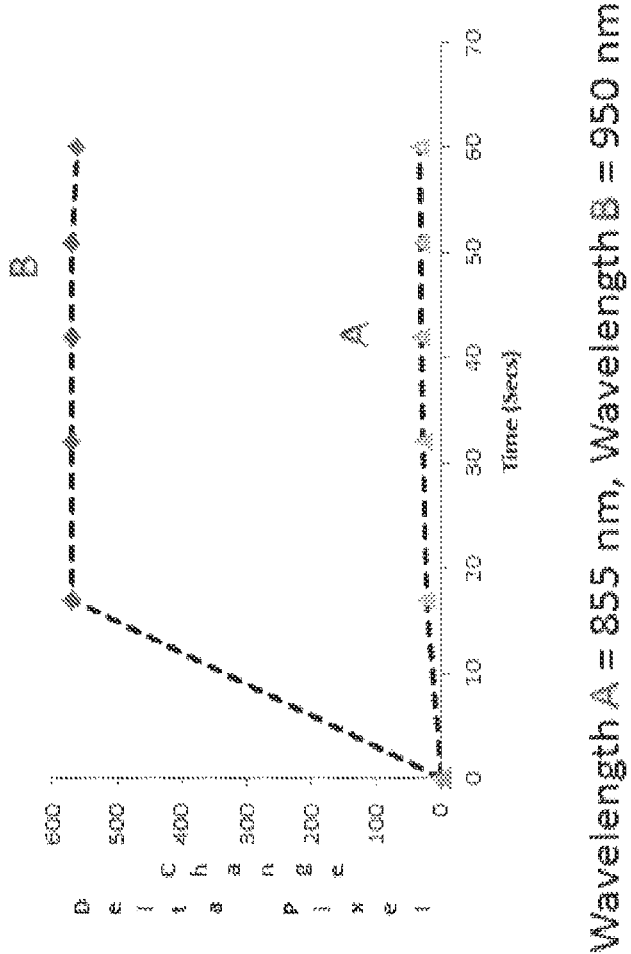
FIG. 54 is a graph showing delta pixel value as a function of time for two different SPR signals that were obtained from a sample of tear fluid having an osmolarity of 300 mOsm/L.

FIG. 54 is a graph showing delta pixel value as a function of time for two different SPR signals that were obtained from a sample of tear fluid having an osmolarity of 300 mOsm/L. The first optical signals has a wavelength of 850 nm and second optical signal has a wavelength of 950 nm. The results demonstrate a significant different in the delta pixel value obtained from the two different optical signals.

Figure 55:
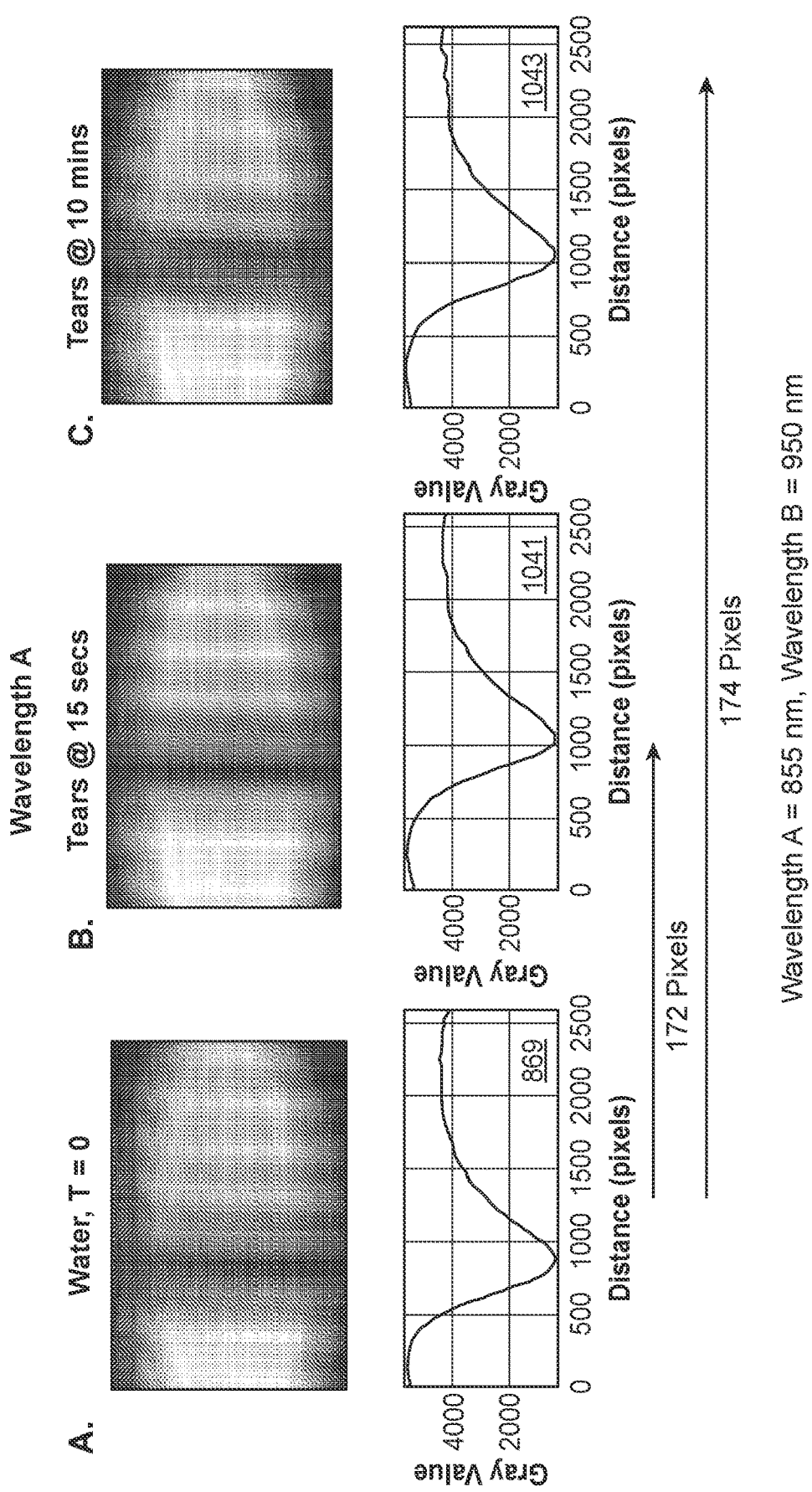
FIG. 55 is a collection of images and graphs showing data obtained from water and from a sample of tear fluid having a protein content that is 80% of the protein content of normal tears, using the methods described herein.

FIG. 55 is a collection of images and graphs showing data obtained from water and from a sample of tear fluid having a protein content that is 80% of the protein content of normal tears, using an optical signal having a wavelength of 855 nm. Panel A, top, shows an image of an SPR signal obtained from water at time zero. The vertical black line representing the SPR minimum value can be seen. Panel A, bottom, shows a graph of grey value as a function of pixel position for the image shown in Panel A, top. The SPR minimum occurs at a pixel position of 869.

Panel B, top, shows an image of an SPR signal obtained from the tear fluid at 15 seconds after the tear fluid is contacted with the sensing surface. The vertical black line representing the SPR minimum value can be seen. Panel B, bottom, shows a graph of grey value as a function of pixel position for the image shown in Panel B, top. The SPR minimum occurs at a pixel position of 1041.

Panel C, top, shows an image of an SPR signal obtained from the tear fluid at 10 minutes after the tear fluid is contacted with the sensing surface. The vertical black line representing the SPR minimum value can be seen. Panel C, bottom, shows a graph of grey value as a function of pixel position for the image shown in Panel C, top. The SPR minimum occurs at a pixel position of 1043.

Below the Panels, the change in pixel position of 172 pixels between water and the tear fluid after 15 seconds is shown, and the change in pixel position of 174 pixels between water and the tear fluid after 10 minutes is shown. The SPR signal from the tear fluid reached a plateau value, and the pixel position corresponding to the minimum value of the SPR signal did not substantially change between 15 seconds and 10 minutes.

Figure 56:
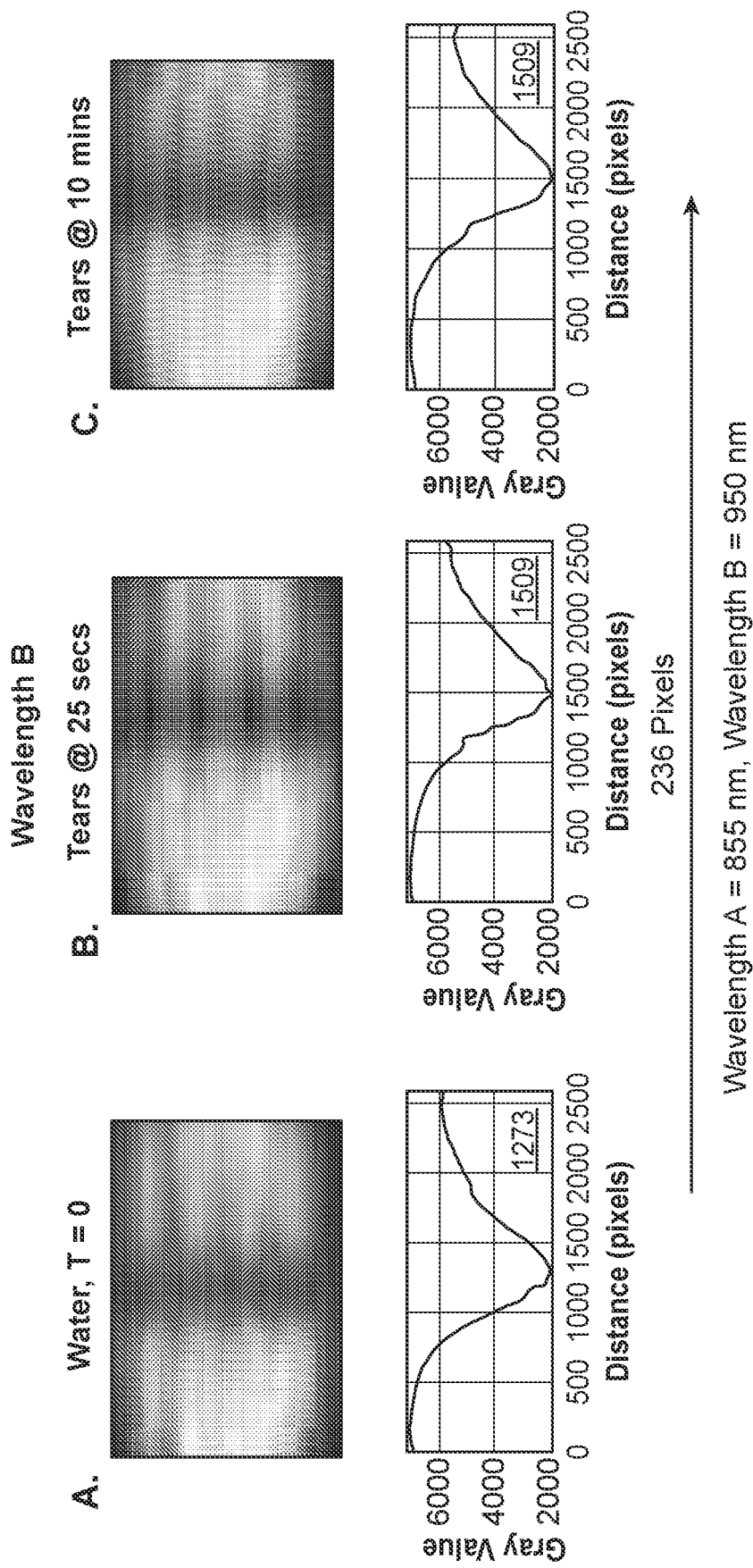
FIG. 56 is a collection of images and graphs showing data obtained from water and from a sample of tear fluid having a protein content that is 80% of the protein content of normal tears, using the methods described herein.

FIG. 56 is a collection of images and graphs showing data obtained from water and from a sample of tear fluid having a protein content that is 80% of the protein content of normal tears, using an optical signal having a wavelength of 950 nm. Panel A, top, shows an image of an SPR signal obtained from water at time zero. The vertical black line representing the SPR minimum value can be seen. Panel A, bottom, shows a graph of grey value as a function of pixel position for the image shown in Panel A, top. The SPR minimum occurs at a pixel position of 1273.

Panel B, top, shows an image of an SPR signal obtained from the tear fluid at 25 seconds after the tear fluid is contacted with the sensing surface. The vertical black line representing the SPR minimum value can be seen. Panel B, bottom, shows a graph of grey value as a function of pixel position for the image shown in Panel B, top. The SPR minimum occurs at a pixel position of 1509.

Panel C, top, shows an image of an SPR signal obtained from the tear fluid at 10 minutes after the tear fluid is contacted with the sensing surface. The vertical black line representing the SPR minimum value can be seen. Panel C, bottom, shows a graph of grey value as a function of pixel position for the image shown in Panel C, top. The SPR minimum occurs at a pixel position of 1509.

Below the Panels, the change in pixel position of 236 pixels between water and the tear fluid after 25 seconds and 10 minutes is shown. The SPR signal from the tear fluid reached a plateau value, and the pixel position corresponding to the minimum value of the SPR signal did not substantially change between 25 seconds and 10 minutes.

Figure 57:
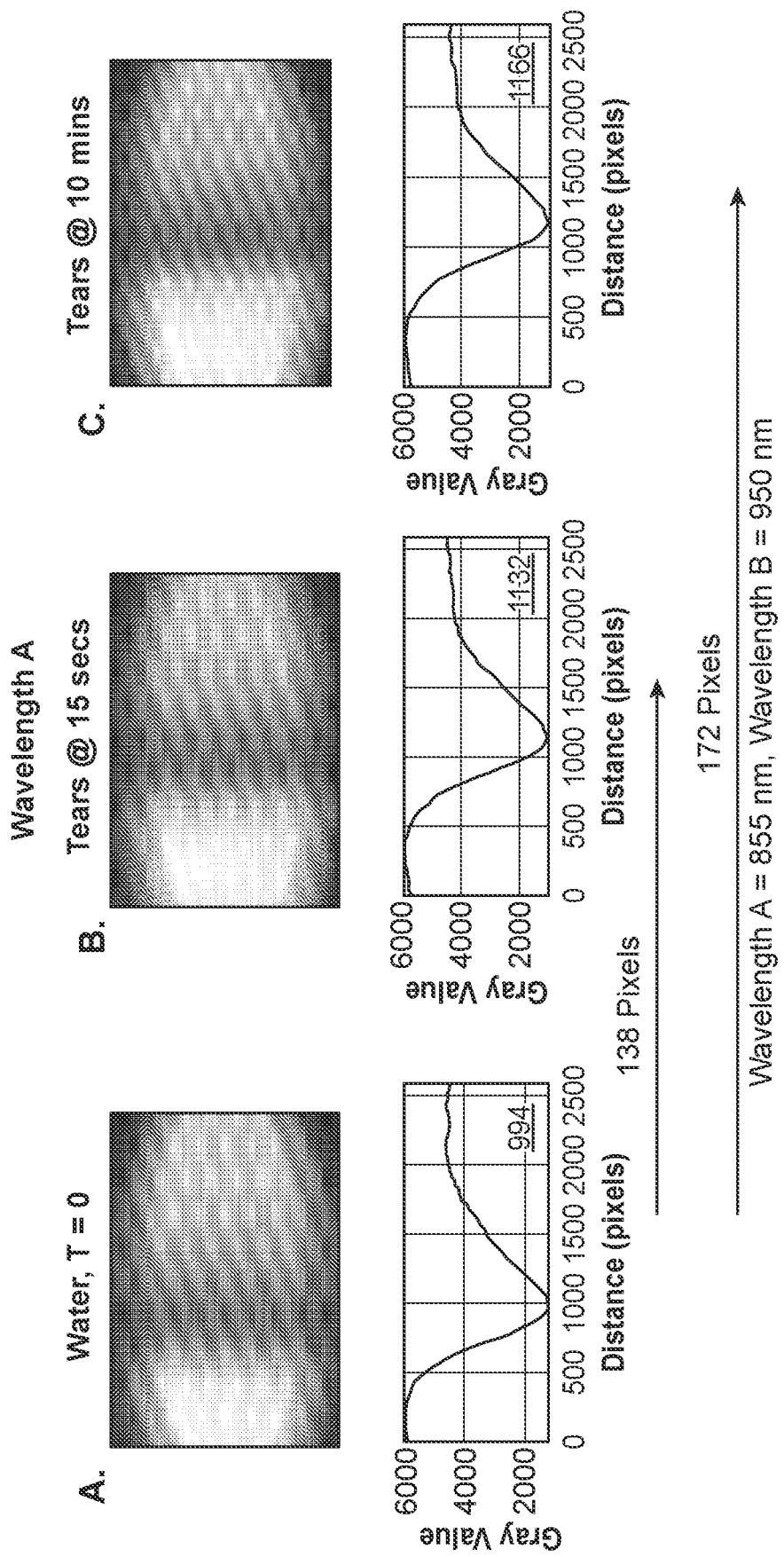
FIG. 57 is a collection of images and graphs showing data obtained from water and from a sample of tear fluid having a protein content that is 120% of the protein content of normal tears, using the methods described herein.

FIG. 57 is a collection of images and graphs showing data obtained from water and from a sample of tear fluid having a protein content that is 120% of the protein content of normal tears, using an optical signal having a wavelength of 855 nm. Panel A, top, shows an image of an SPR signal obtained from water at time zero. The vertical black line representing the SPR minimum value can be seen. Panel A, bottom, shows a graph of grey value as a function of pixel position for the image shown in Panel A, top. The SPR minimum occurs at a pixel position of 994.

Panel B, top, shows an image of an SPR signal obtained from the tear fluid at 15 seconds after the tear fluid is contacted with the sensing surface. The vertical black line representing the SPR minimum value can be seen. Panel B, bottom, shows a graph of grey value as a function of pixel position for the image shown in Panel B, top. The SPR minimum occurs at a pixel position of 1132.

Panel C, top, shows an image of an SPR signal obtained from the tear fluid at 10 minutes after the tear fluid is contacted with the sensing surface. The vertical black line representing the SPR minimum value can be seen. Panel C, bottom, shows a graph of grey value as a function of pixel position for the image shown in Panel C, top. The SPR minimum occurs at a pixel position of 1166.

Below the Panels, the change in pixel position of 138 pixels between water and the tear fluid after 15 seconds is shown, and the change in pixel position of 172 pixels between water and the tear fluid after 10 minutes is shown.

Figure 58:
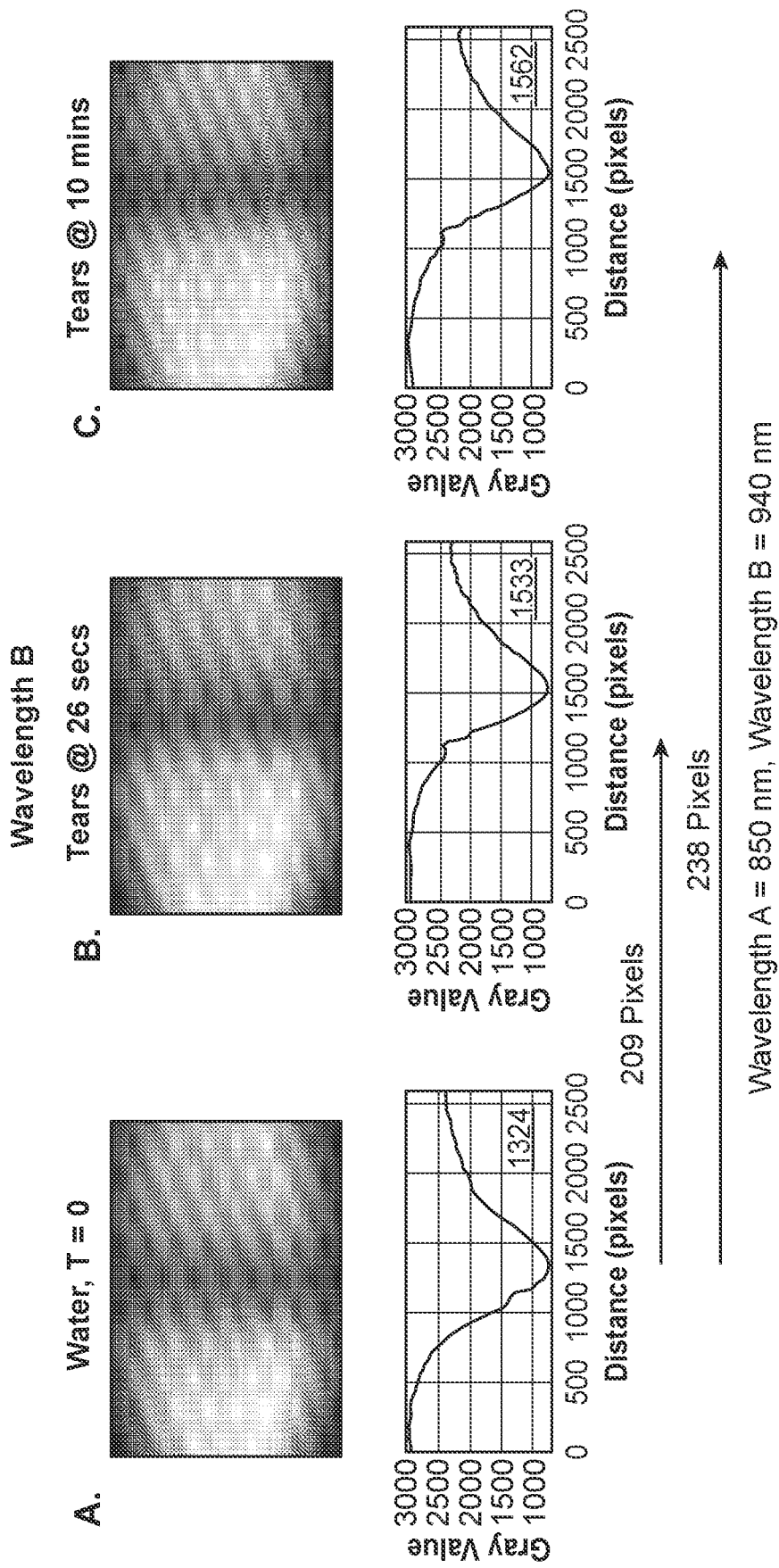
FIG. 58 is a collection of images and graphs showing data obtained from water and from a sample of tear fluid having a protein content that is 120% of the protein content of normal tears, using the methods described herein.

FIG. 58 is a collection of images and graphs showing data obtained from water and from a sample of tear fluid having a protein content that is 120% of the protein content of normal tears, using an optical signal having a wavelength of 950 nm. Panel A, top, shows an image of an SPR signal obtained from water at time zero. The vertical black line representing the SPR minimum value can be seen. Panel A, bottom, shows a graph of grey value as a function of pixel position for the image shown in Panel A, top. The SPR minimum occurs at a pixel position of 1324.

Panel B, top, shows an image of an SPR signal obtained from the tear fluid at 26 seconds after the tear fluid is contacted with the sensing surface. The vertical black line representing the SPR minimum value can be seen. Panel B, bottom, shows a graph of grey value as a function of pixel position for the image shown in Panel B, top. The SPR minimum occurs at a pixel position of 1533.

Panel C, top, shows an image of an SPR signal obtained from the tear fluid at 10 minutes after the tear fluid is contacted with the sensing surface. The vertical black line representing the SPR minimum value can be seen. Panel C, bottom, shows a graph of grey value as a function of pixel position for the image shown in Panel C, top. The SPR minimum occurs at a pixel position of 1562.

Below the Panels, the change in pixel position of 209 pixels between water and the tear fluid after 26 seconds is shown, and the change in pixel position of 238 pixels between water and the tear fluid after 10 minutes is shown.

Figure 59:
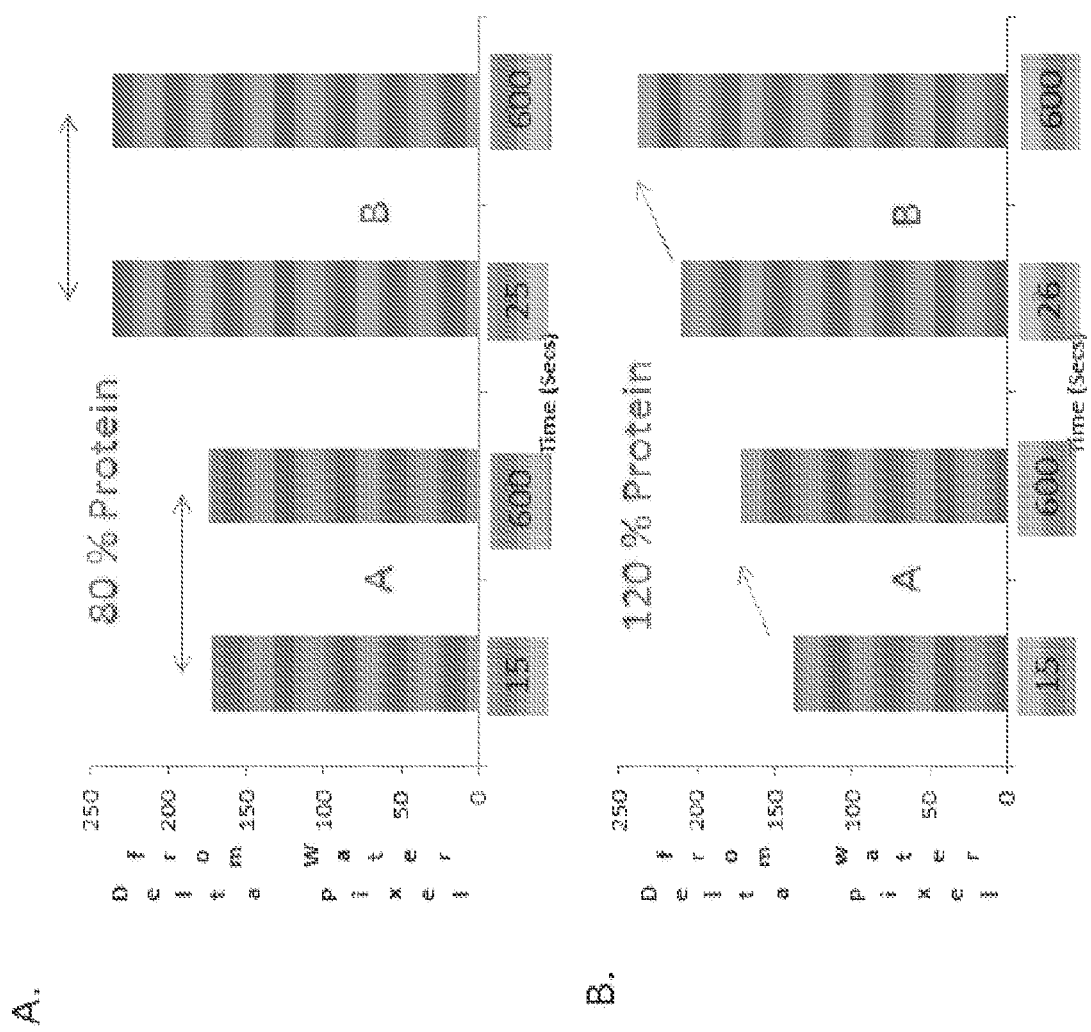
FIG. 59 is a set of graphs showing the results from a comparative analysis of a sample of tear fluid having a protein content that is 80% of the protein content of normal tears, and a sample of tear fluid having a protein content that is 120% of the protein content of normal tears, using the subject methods.

FIG. 59 is a comparative analysis of a sample of tear fluid having a protein content that is 80% of the protein content of normal tears, and a sample of tear fluid having a protein content that is 120% of the protein content of normal tears. Panel A shows the sample having 80% of the protein content of normal tears, which was analyzed using an optical signal having wavelength A (855 nm) and wavelength B (950 nm). The bar graph in Panel A shows the change in delta pixel value for the 80% protein sample at the first wavelength between 15 seconds and 600 seconds, and at the second wavelength between 25 seconds and 600 seconds. The data show that for the 80% protein tear fluid, there was very little change in the delta pixel value as a function of time for either wavelength, and that the second wavelength created a greater response in delta pixel value as compared to the first wavelength.

Panel B shows the sample having 120% of the protein content of normal tears, which was analyzed using an optical signal having wavelength A (855 nm) and wavelength B (950 nm). The bar graph in Panel B shows the change in delta pixel value for the 120% protein sample at the first wavelength between 15 seconds and 600 seconds, and at the second wavelength between 25 seconds and 600 seconds. The data show that for the 120% protein tear fluid, there was a greater change in the delta pixel value as a function of time for both wavelengths, and that the second wavelength created a greater response in delta pixel value as compared to the first wavelength.

Figure 60:
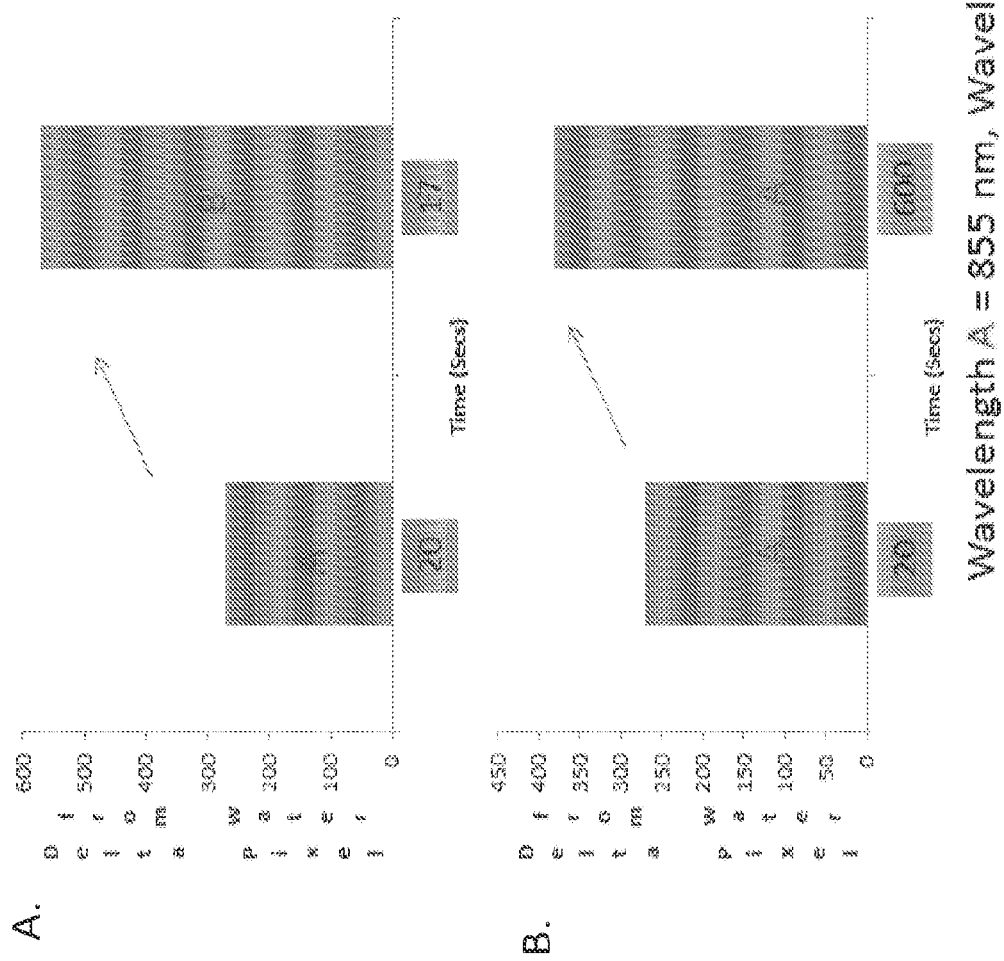
FIG. 60 is a set of graphs showing the results from a comparative analysis of a normal tear fluid sample using the subject methods.

FIG. 60 is an analysis of a tear fluid having 100% of the protein in normal tears (i.e., a normal tear fluid sample), analyzed at two different wavelengths (855 nm and 950 nm), and over shorter and longer time intervals. Panel A is a bar graph showing delta pixel value for the same sample when analyzed using wavelength A (855 nm) for 20 seconds and wavelength B (950 nm) for 17 seconds. At these shorter time intervals, wavelengths A and B provide different delta pixel values, which are clearly distinguished from one another. Panel B is a bar graph showing delta pixel value for the same sample when analyzed using wavelength A (855 nm) for 20 seconds and wavelength A (855 nm) for 600 seconds. The change in delta pixel value as a function of time at the same wavelength can clearly be seen.

Figure 61:
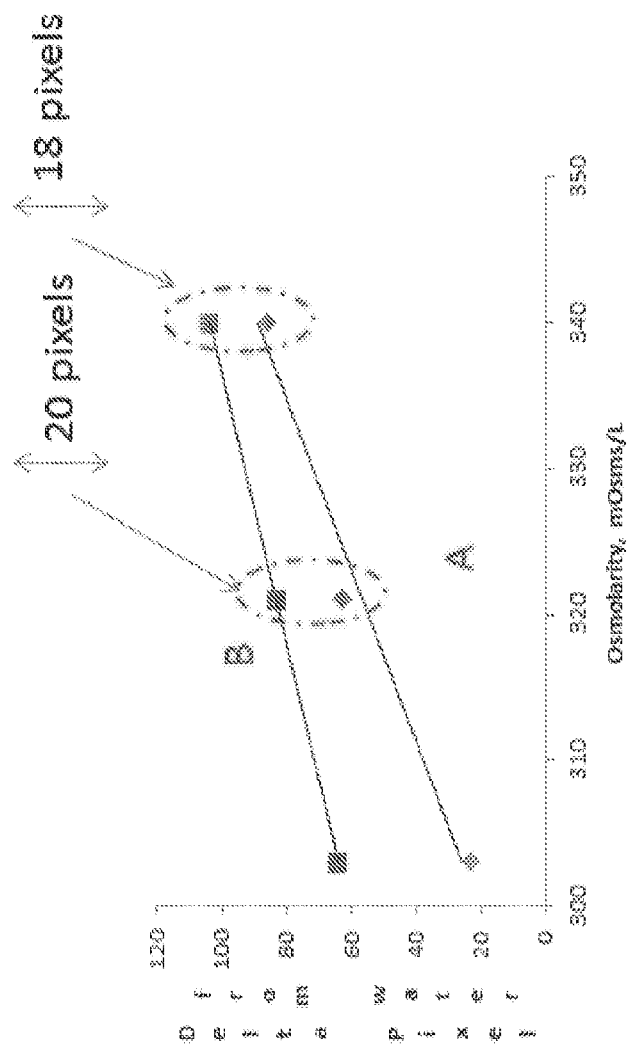
FIG. 61 is a graph showing the delta pixel value of a salt solution as a function of osmolarity, analyzed using two different wavelengths.

FIG. 61 is a graph showing the delta pixel value of a salt solution as a function of osmolarity. The lower series (diamonds) was obtained using wavelength A (855 nm) and the upper series (squares) was obtained using wavelength B (950 nm). At an x axis position corresponding to 320 mOsm/L, the difference in the y values of the two series is 20 pixels, as shown. At an x axis position corresponding to 340 mOsm/L, the difference in the y values of the two series is 18 pixels, as shown. This data demonstrates that different changes in delta pixel value are observed for samples having different osmolarities as a function of the wavelength that is used to conduct the analysis.

The following examples are provided to aid the understanding of the present invention, the true scope of which is set forth in the appended claims. It is understood that modifications can be made in the procedures set forth without departing from the spirit of the invention.

EXAMPLES

Example 1: Reduction of Optical Noise in a Sensor Using a Point Source LED

Figure 3:
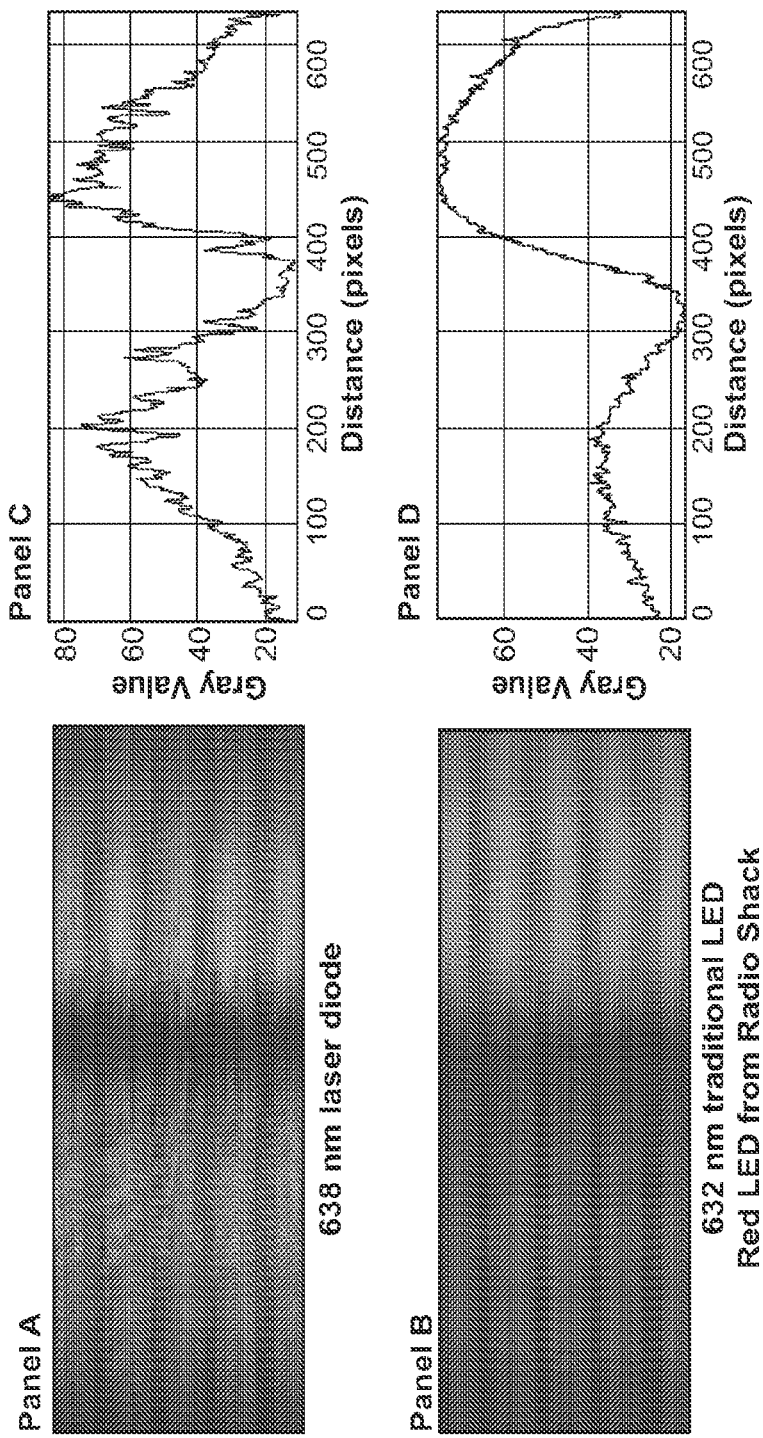
FIG. 3, Panel A is an image generated using a 638 nm wavelength laser, and Panel B is an image generated using a 632 nm wavelength traditional LED. Panel C is a graph showing a larger amount of noise from the laser diode image. Panel D is a graph showing a lower amount of noise from the LED. The graph in Panel D is noticeably smoother than the graph in Panel C.

Optical noise reduction was achieved in a system by using a point source LED as an optical signal generating component. FIG. 3 illustrates clearly that a 638 nm laser diode has substantially higher optical noise than a red LED (632 nm nominal wavelength), as depicted graphically in the each of the charts to the right of their corresponding SPR images. Use of a point source LED instead of a laser diode thus reduced the optical noise in the system.

Example 2: Optimizing Resolution of SPR Signal Measurement

Figure 4:
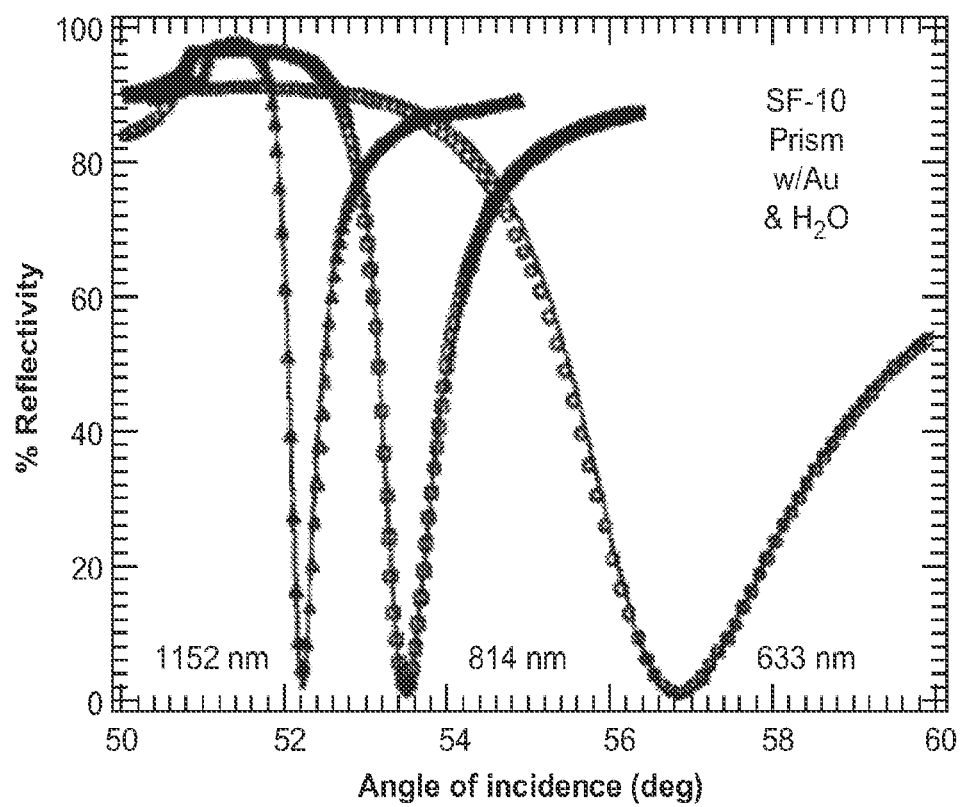
FIG. 4 is a graph comparing precent reflectivity as a function of angle of incidence for three different optical signals that have different wavelengths. The longer wavelength optical signals have narrower (sharper) SPR line widths.
Figure 5:
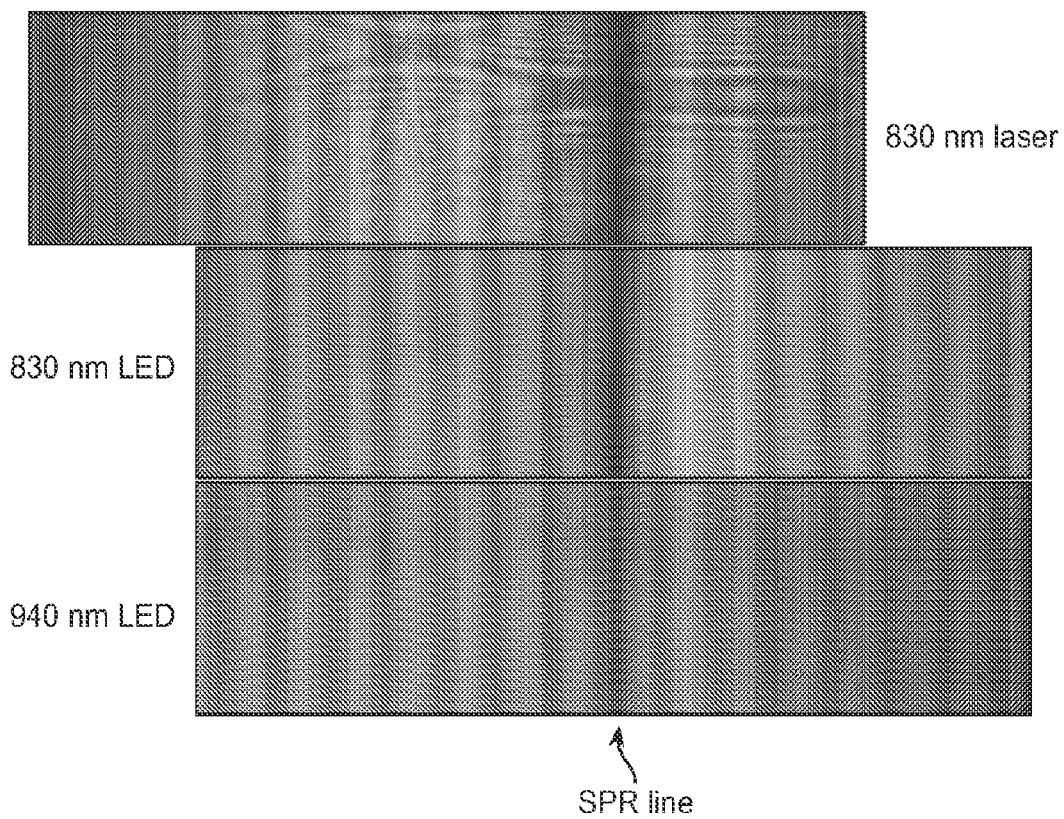
FIG. 5 is a collection of three different images demonstrating the difference in image quality for different optical sources with different wavelengths. The width of the SPR line is narrower for light having a larger wavelength.

As shown in FIG. 4, longer wavelength optical signals produce narrower SPR line widths. FIG. 5 illustrates the narrowing of the SPR line with increasing wavelength as verified experimentally using a simple SPR set-up on an optical table. The decrease of the SPR line width with increasing wavelength is readily apparent to the naked eye.

Figure 6:
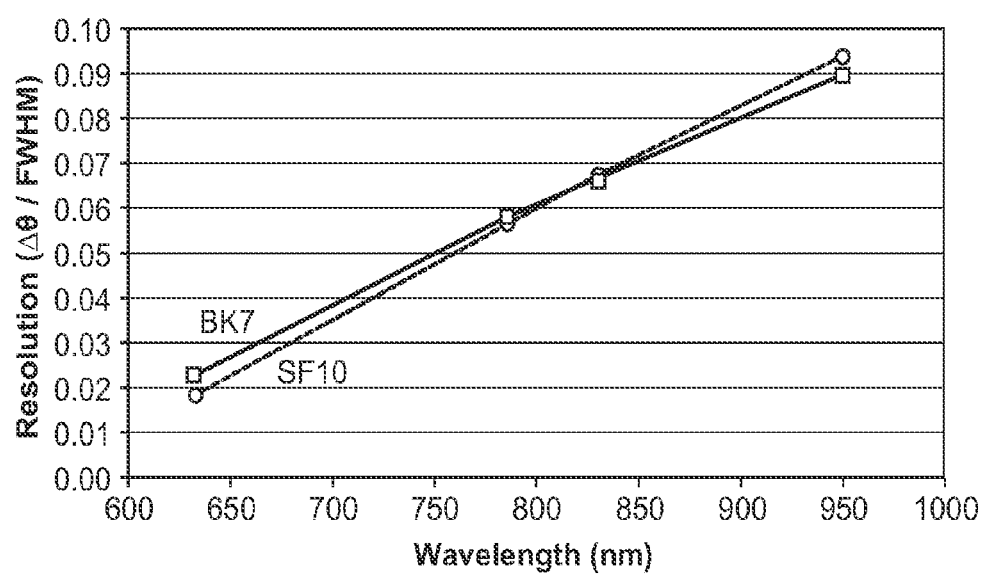
FIG. 6 is a graph showing resolution as a function of wavelength for a high index of refraction glass (SF10, refractive index ~1.72) and a lower index of refraction glass (BK7, refractive index ~1.52). The graph shows that there is little difference between the different materials.

It was unclear whether the narrower SPR line width at longer wavelengths would provide higher SPR resolution in the subject systems, since the angular shift of the SPR minima decreases with longer wavelengths. Consequently, calculations of the angular shift $\Delta\theta$ of the SPR minima for a change in index of refraction by 0.001 refractive index units ("RIU") and the full width at half maximum ("FWHM") of the SPR line were performed using an online SPR calculator provided by the Research Group of Prof. Robert M. Corn at the Dept. of Chemistry, University of California, Irvine (http://unicorn.ps.uci.edu/calculations/fresnel/fcform.html). The ratio of these two quantities (i.e. $\Delta\theta$/FWHM) was defined as the SPR resolution. The result of the calculations was that the improvement of resolution at a wavelength of 950 nm as compared to 635 nm was in the range of 4 to 5 times. These calculations also showed that there was a negligible difference in resolution obtained using either high index glass (SF10, n ~1.72) or a lower index glass (BK7, n ~1.52) (see FIG. 6).

Prior to these calculations, the popular scientific folklore was that high index prisms provided substantially better SPR performance than lower index prisms. As a consequence, this well-established scientific folklore taught away from using injection molded optical plastics as disposable SPR prisms, since optical plastics generally have relatively low refractive indices. Thus, based on the above calculations, injection molded optical plastics can be used as disposable SPR prisms in the subject sensors and systems, thereby reducing cost of goods.

Example 3: Derivative Signal Processing

Measurement of tear osmolarity to 1.0 mOsm/L corresponds to determination of the index of refraction of the tear solution to about 1 part in $10^{-5}$ RIU. A common engineering rule of thumb is that the precision of a measurement should exceed the targeted precision by about a factor of 10. Consequently it is desirable in a tear osmolarity measurement device to have an ultimate index of refraction precision of about 1 part in $10^{-6}$ RIU.

Figure 7:
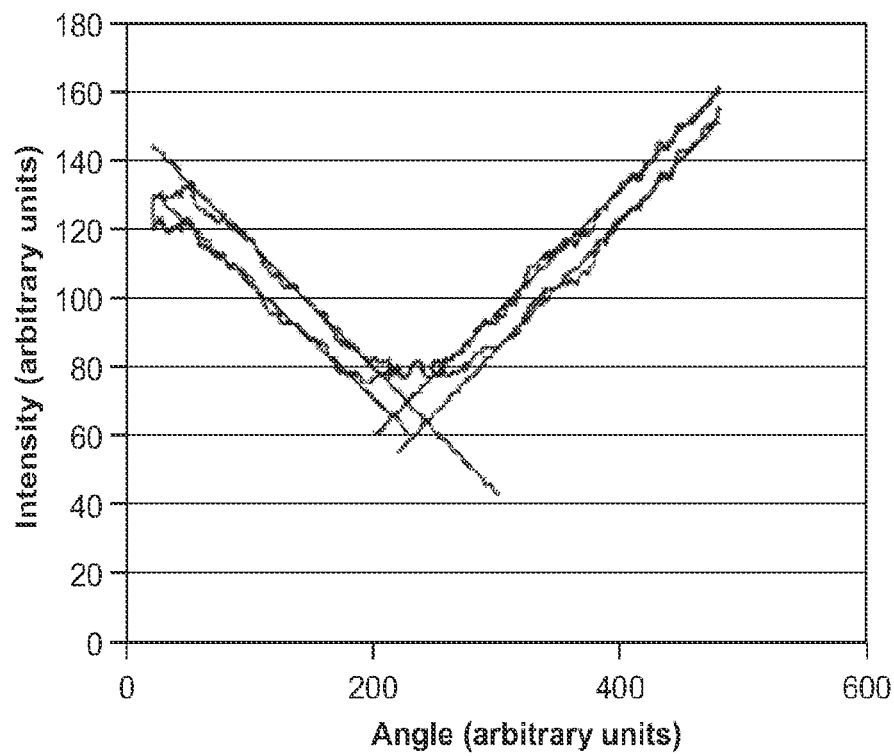
FIG. 7 is a graph demonstrating the straight line fit approach for determining a minimum value of an SPR curve.

Various techniques for determining the location of a SPR line minimum are known in the art. One technique is to fit straight lines to the falling and rising edges of an SPR line, and is depicted in FIG. 7. A brief description of the technique is found in U.S. Pat. No. 7,395,103, the disclosure of which is herein incorporated by reference in its entirety. Another technique, described as a centroid method, is also disclosed in U.S. Pat. No. 7,395,103.

It is well known that the points at which the derivative of a function is zero represent either local maxima or minima of the function. Scientific folklore dismisses use of derivatives to find either the maxima or minima of real world data, since any real world data contains noise. The commonly held belief is that taking the derivative of noisy data will result in unacceptable noise in the derivative data, thus precluding accurate determination location of the derivative zero crossings.

In practice there are three effects that can counteract the effects of noise of derivative signal processing for finding the exact location of the minima of an SPR curve. The first is to begin with a very low noise SPR line image. Here, this was accomplished by careful optical design, and by using LEDs rather than lasers for the optical source. Second, moving from visible light sources to near infrared light sources results in considerably narrower SPR lines for which the rate of change of intensity near the SPR minima is rapid, resulting in large derivative signals relative to any noise in the signal. Finally, any residual noise in the image of the SPR line can be minimized by suitable low pass filtering. Here, a Gaussian blur algorithm was used to diminish any residual image noise to acceptable levels.

Figure 8:
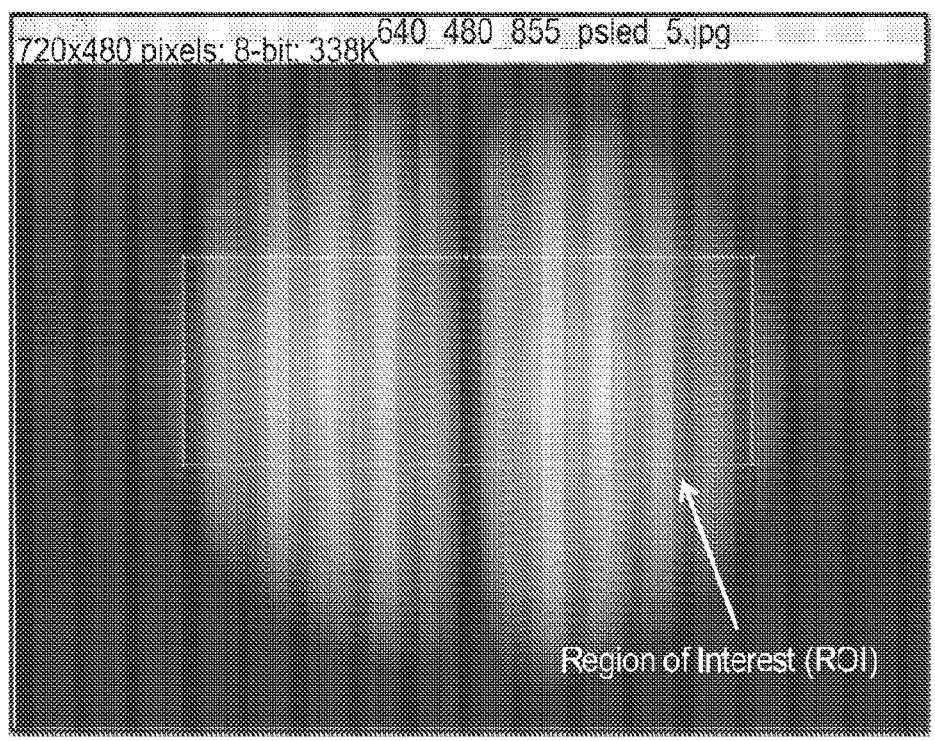
FIG. 8 is an SPR line image acquired using a video imager. A region of interest within the image is outlined with the depicted rectangle.
Figure 9:
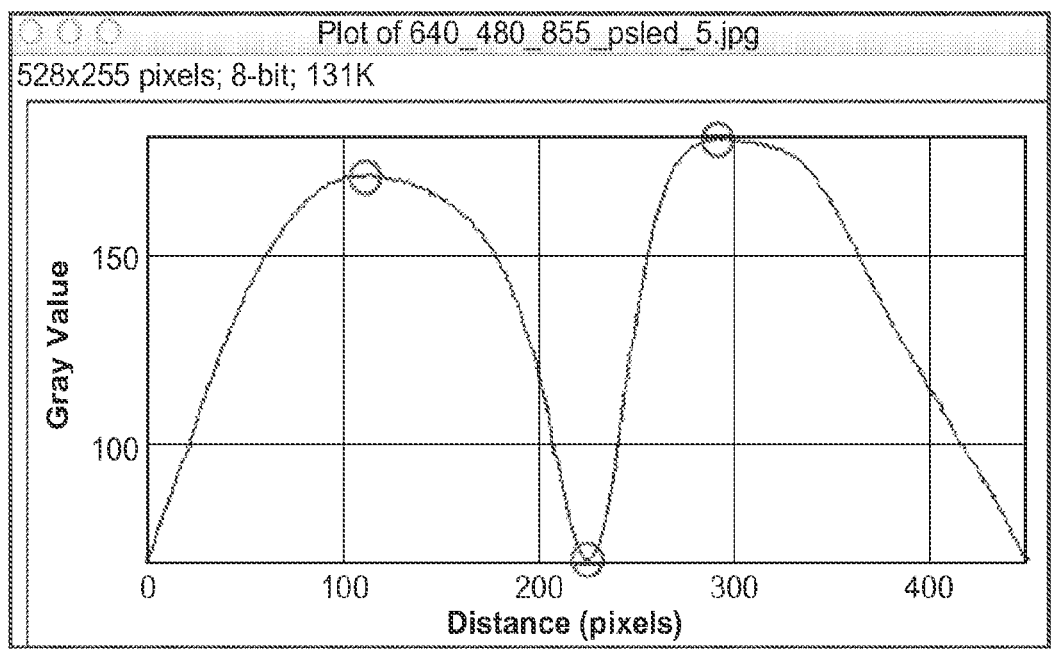
FIG. 9 is a graph showing the gray scale value as a function of pixel position for the region of interest depicted in FIG. 8. The graph was generated corresponding to the average of the vertical column pixel intensity in the region of interest along the X direction.
Figure 10:
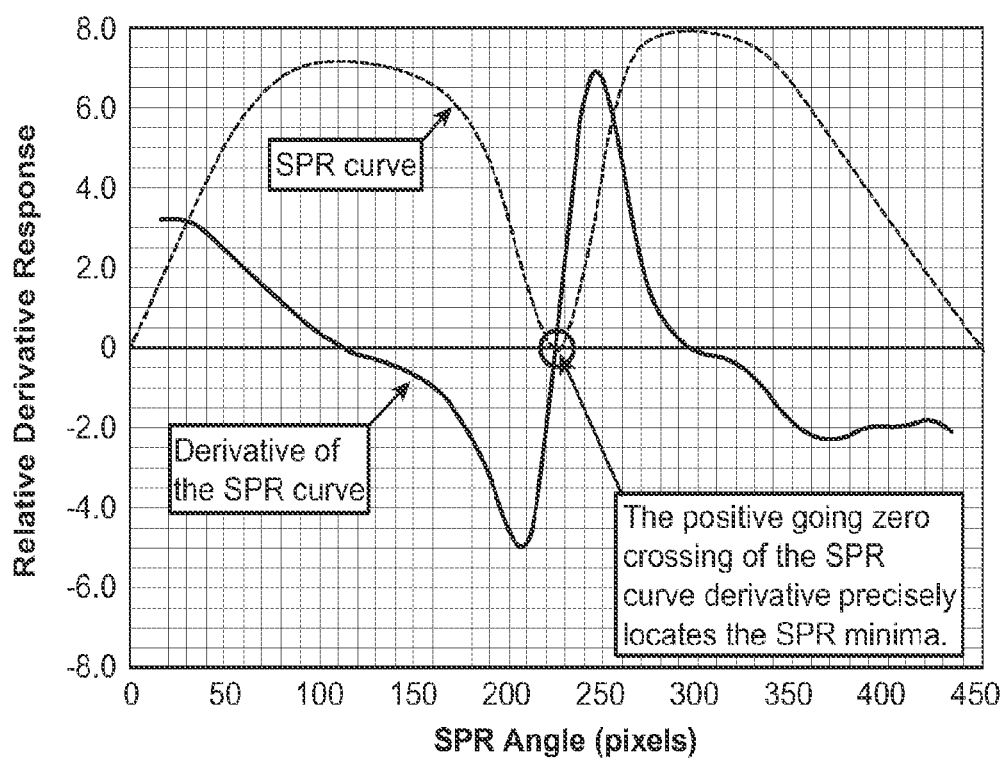
FIG. 10 is a graph showing the SPR curve depicted in FIG. 9 (dotted line) as well as the derivative of the SPR curve (solid line) as a function of SPR angle (pixels). The zero crossing of the derivative of the SPR curve is circled.

FIG. 8 presents a typical SPR line image obtained using an 855 nm point source LED as the light source. This image was acquired using a 640×480 video imager. The image was imported into the application ImageJ image processing software developed at the U.S. National Institutes of Health. Next, 25 pixels of Gaussian blur was applied to the image and an appropriate region of interest was defined for the image, as denoted by the rectangle in FIG. 8. Within this region of interest ("ROI") a plot profile was generated corresponding to the average of the vertical column pixel intensity in the image along the X direction. The result of these operations is shown in FIG. 9, which is an ImageJ Plot Profile of the region of interest. Finally, data from the plot profile curve can be differentiated numerically using well known mathematical techniques in order to find the positive going zero crossing of the derivative which precisely defines the location of the minima of the SPR line (as shown in FIG. 10). Note that the derivative curve shown in FIG. 10 is actual data derived from the SPR image in FIG. 8. The derivative curve is extremely smooth and exhibits no obvious noise artifacts.

Figure 11:
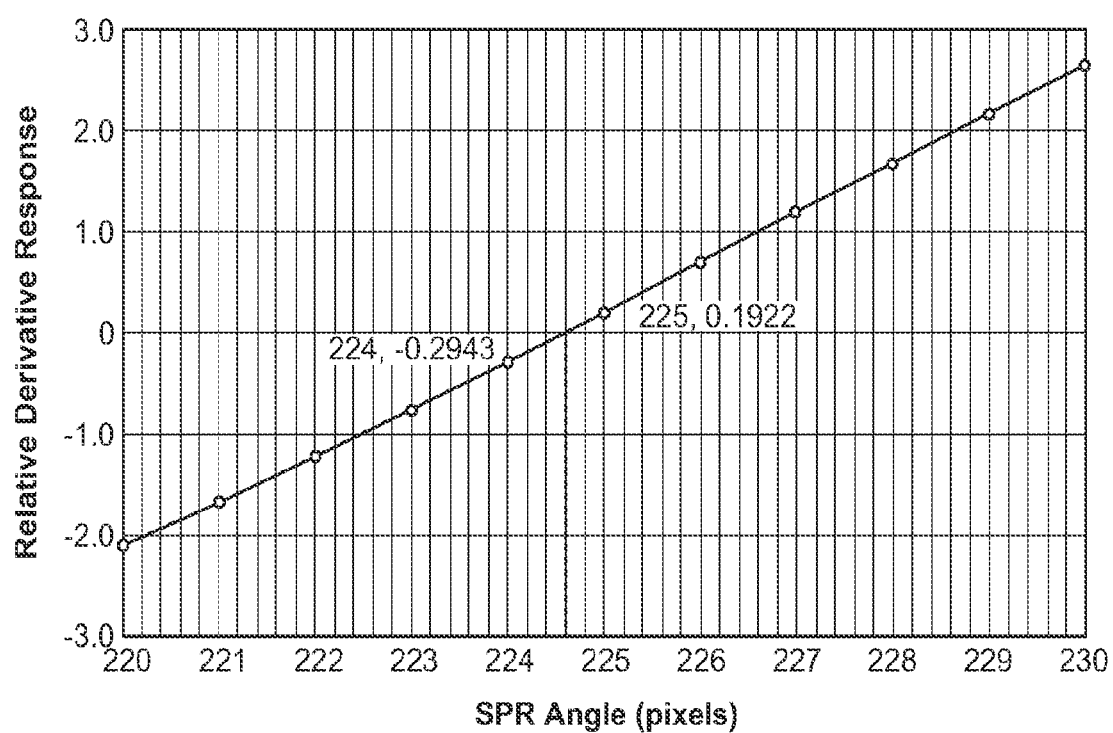
FIG. 11 is a graph showing the location of the zero crossing of the derivative of the SPR curve depicted in FIG. 10 to a fraction of a pixel value.
Figure 12:
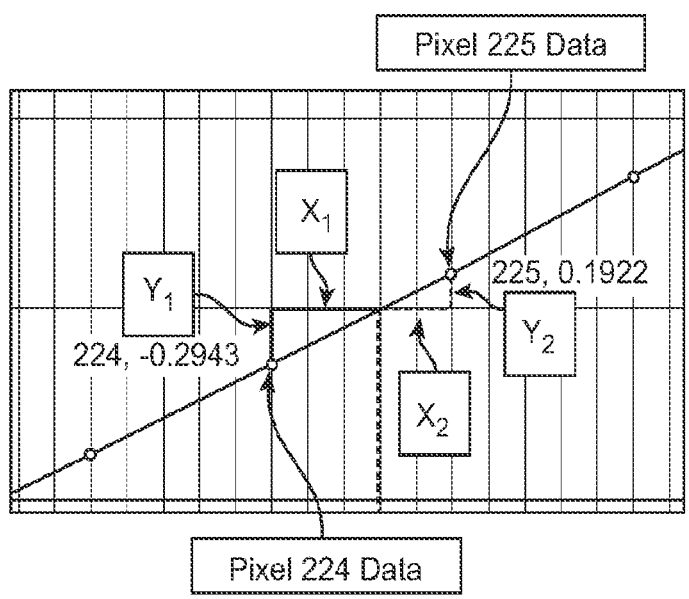
FIG. 12 is a graph showing determination of the exact coordinate of the zero crossing point using a linear interpolation technique.

In practice, due to the low level of noise in in the derivative data, the zero crossing of the SPR line's derivative can be located to within a fraction of a pixel using interpolation techniques. FIG. 11 illustrates the relative value of the derivative of the SPR image in FIG. 8. Note that there is very little noise in the derivative and that over the limited range from 220 pixels to 230 pixels the derivative is nearly linear. The zero crossing of the derivative occurs between pixel 224 and 225, with coordinates of (224, −0.2943) at pixel 224 and (225, 0.1922) at pixel 225. From these values, the exact coordinate of the zero crossing can be determined by linear interpolation, as shown in the geometry illustrated in FIG. 12. For this example, the zero crossing occurs precisely at the coordinate (244.6049, 0.0).

Figure 14:
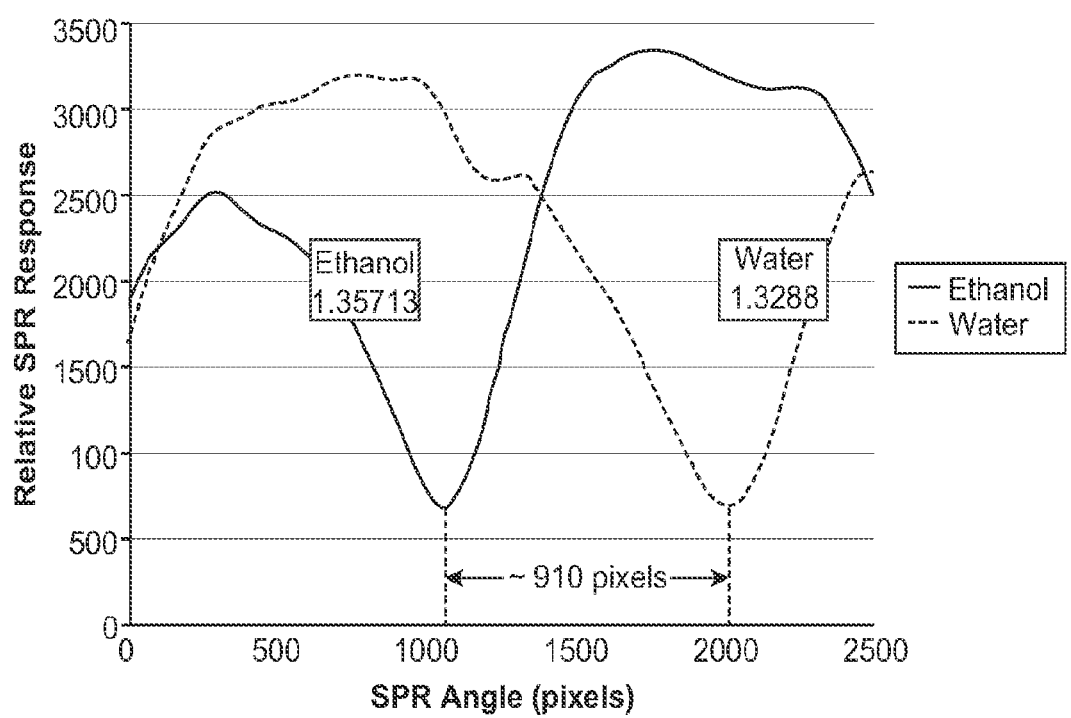
FIG. 14 is a graph showing a relative SPR response for ethanol and for deionized water. The difference in pixel position for the two media is shown as approximately 910 pixels.
Figure 15:
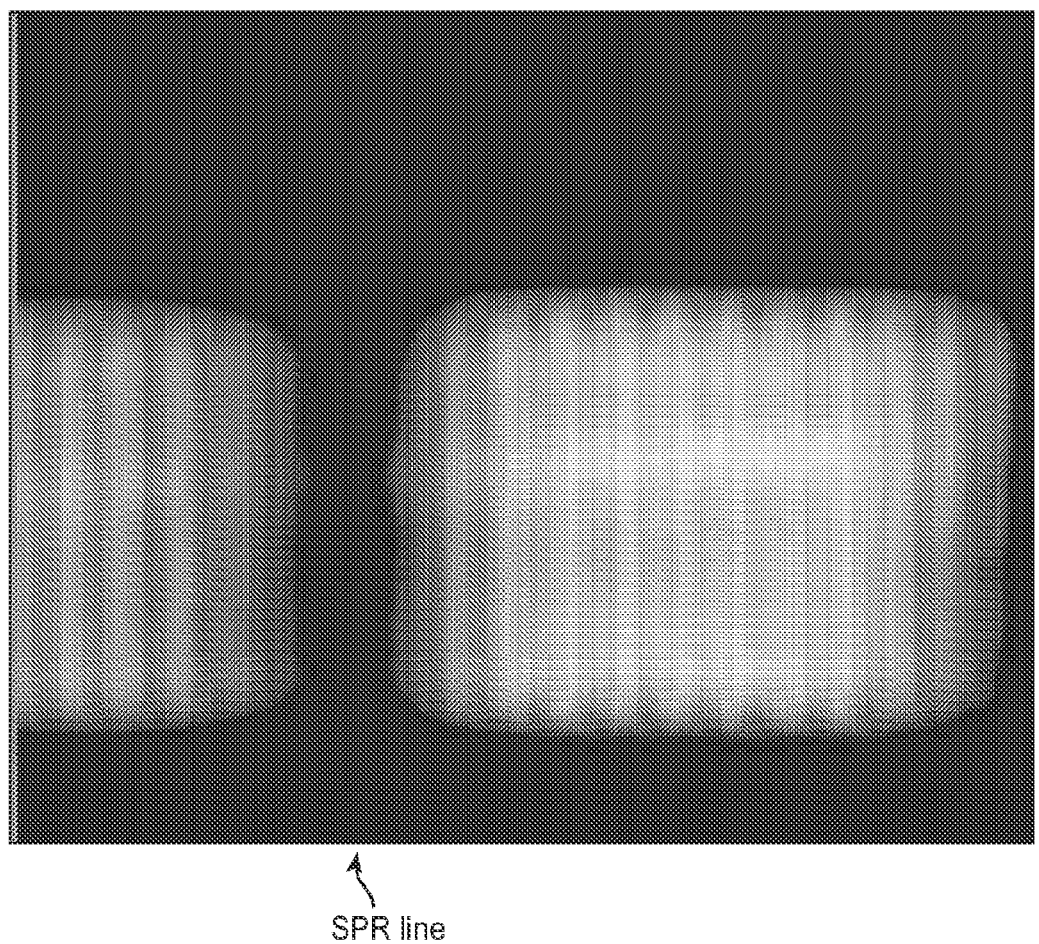
FIG. 15 is an image showing raw SPR data for an ethanol solution.
Figure 16:
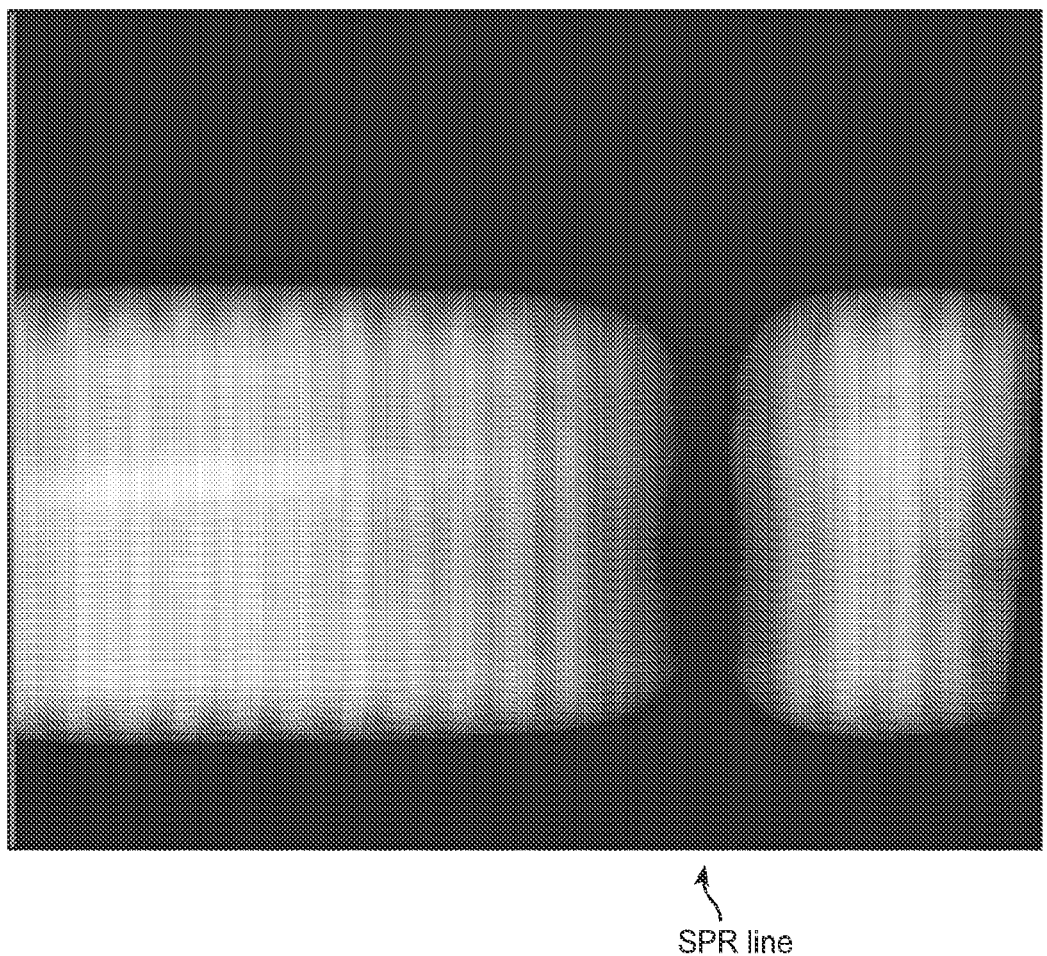
FIG. 16 is an image showing raw SPR data for an deionized water solution.

FIG. 13 presents the location of the SPR minima for 10 SPR images sequentially acquired at approximately 1.0 second intervals. There were no changes in the SPR set-up or other test conditions between each image acquisition other than time, so that variations in the location of the SPR minima are largely due to the random optical and electronic noise present in each acquired image. The images represented by these data were acquired using an Aptina MT9P031 five megapixel grayscale image sensor comprised of 2592 horizontal×1944 vertical 2.2 μm square pixels. A separate calibration step, illustrated in FIG. 14, entailed measuring the SPR line minima pixel locations for ethanol and deionized water corresponding to a separation of approximately 910 pixels. The index of refraction differential between these two liquids is $\Delta n=1.35713$ (ethanol)− 1.3288 (DI water)=0.02833. The result that the $\Delta n$ per pixel is $3.113\times10^{-5}$ RIU (FIG. 14). The raw SPR images for the ethanol and deionized water SPR lines used in this calibration are shown in FIG. 15 and FIG. 16, respectively.

Returning to FIG. 13, the overall range of the zero crossing points over the 10 samples is 0.2662 pixel or ±0.1331 pixel total range about the mean pixel value. This corresponds to an overall uncertainty of the index of refraction of $\pm 4.143\times10^{-6}$ R.

Figure 17:
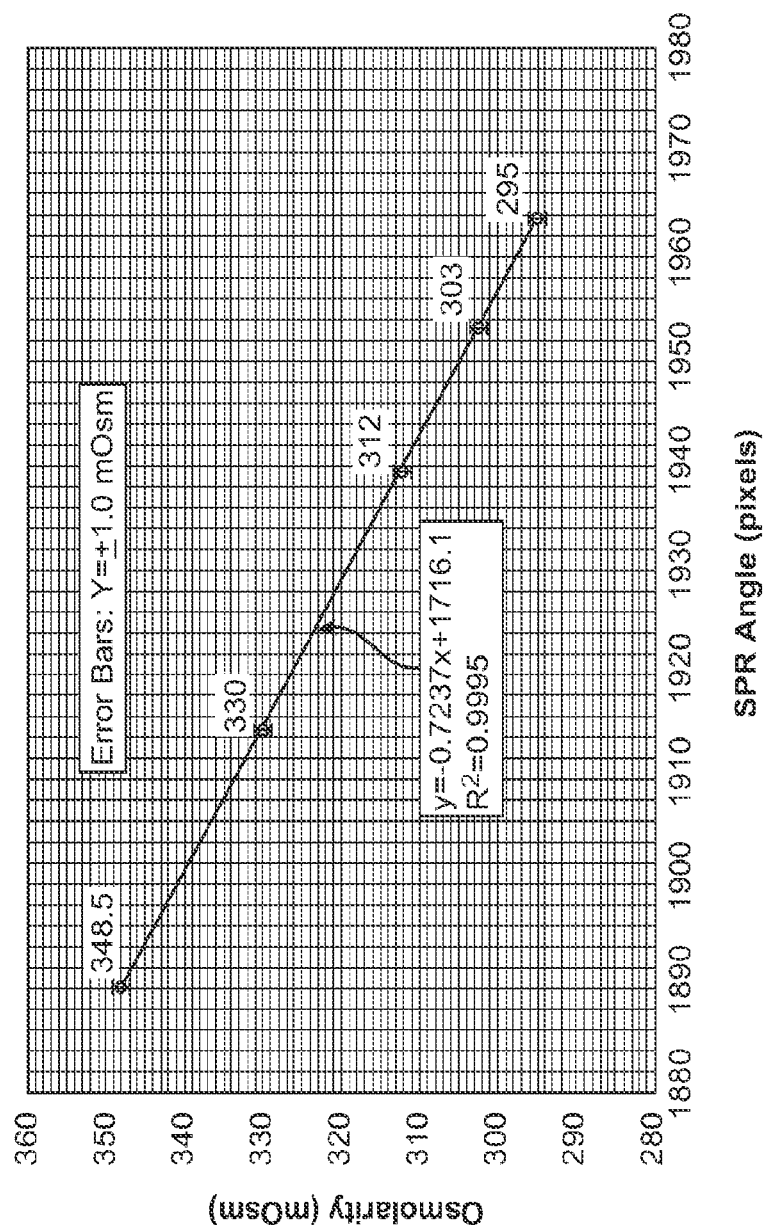
FIG. 17 is a graph showing osmolarity as a function of SPR angle (pixels) acquired and analyzed using the derivative signal processing technique.

FIG. 17 depicts SPR osmolarity data acquired and analyzed using the derivative signal processing described above. A series of five precision calibrated saline solutions were measured with a miniature optical breadboard SPR instrument comprised of a gold coated high index glass SPR prism, an 855 nm point source LED and the Aptina MT9P031 five megapixel image sensor. The data captured with this breadboard and processed using the derivative signal processing technique demonstrated ±1.0 mOsm/L precision over an osmolarity range from 295 mOsm/L to 348.5 mOsm/L. The saline solutions were independently calibrated using the freezing point depression osmolarity measurement technique that also has a stated precision of ±1.0 mOsm/L. Clearly the agreement between the freezing point depression method and the SPR technique is within the limits of experimental error.

Figure 18:
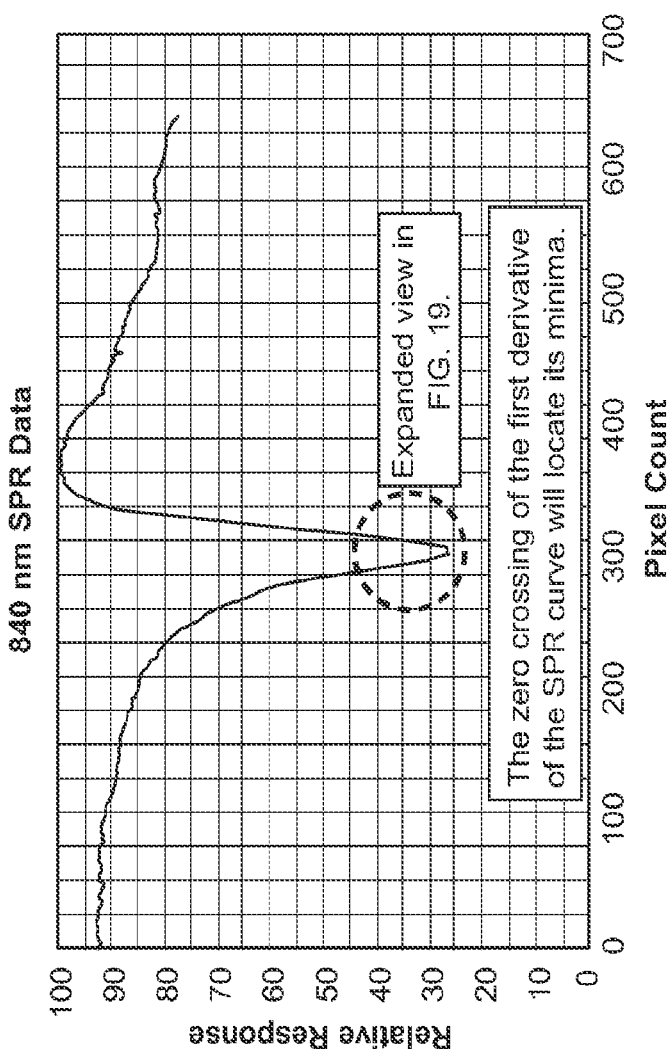
FIG. 18 is a graph showing relative response as a function of pixel count that was generated using a curve fitting technique.
Figure 19:
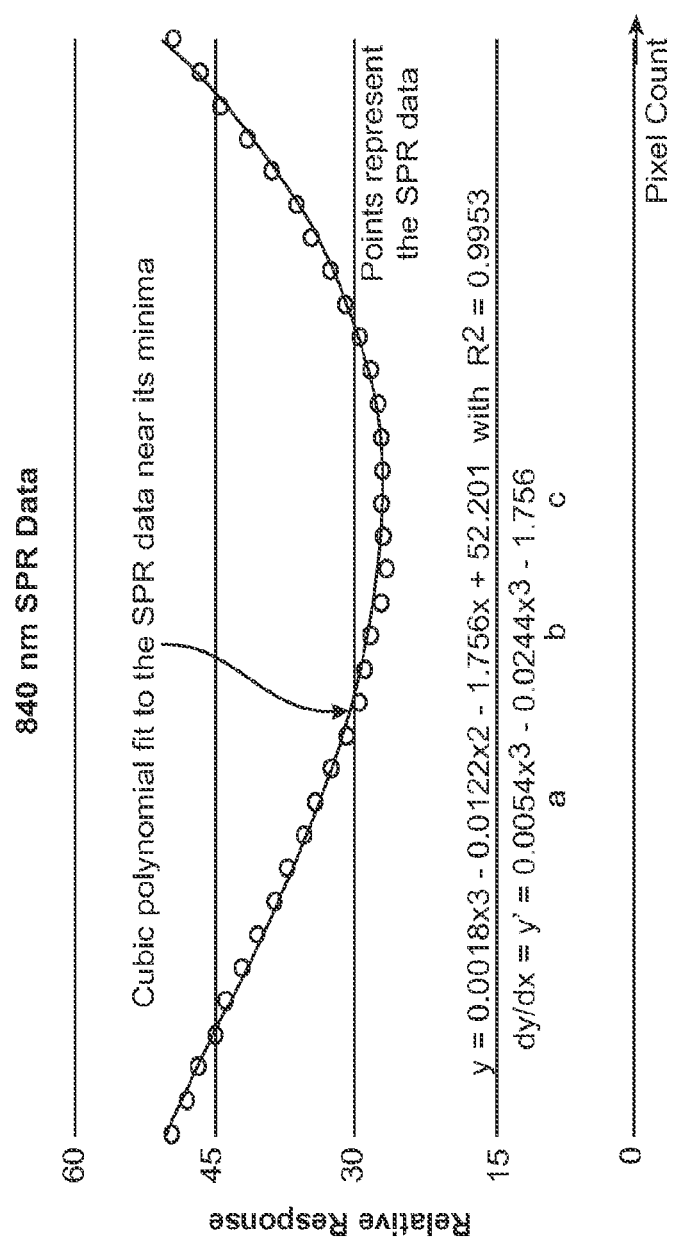
FIG. 19 is a graph showing relative response as a function of pixel count that was generated by fitting a cubic polynomial to the SPR curve.

An alternative approach to using low pass filtering (e.g., Gaussian blur) for noise reduction in the derivative signal processing is to use curve fitting in the region of the SPR minimum to average out noise in the SPR image. FIG. 18 is an SPR line used to demonstrate this approach to derivative signal processing. It should be noted that the SPR line profile in FIG. 18 is distinctly non-symmetric, with the slope on the left hand side of the SPR minima being substantially less (and opposite in sign) than the slope on the right hand side of the minima. While it is tempting to think of fitting the minima of the SPR line minima to a parabola, in practice this results in a poor fit and low $R^2$ value. The consequence is that location of the zero crossing found in this manner is displaced from the actual location of the SPR minima. A more accurate approach is to fit a cubic to the SPR line in the vicinity of its minima as illustrated in FIG. 19. Generally this results in a $R^2$ value near unity. The resulting cubic equation can then be differentiated, set to zero and solved using the quadratic equation to find the location of the SPR minimum, as further described in FIG. 20.

Example 4: Self-Calibration Sensor Theory

SPR-based analysis can provide extremely precise measurements of the change of refractive index of a medium (e.g., a gas or a liquid) in contact with the exterior gold surface of the SPR prism. With suitable care, changes of index of refraction in the range of 1 part in $10^{-6}$ RIU can be obtained under carefully controlled laboratory conditions (see FIG. 13). The premise of using SPR for tear osmolarity measurements is that tear osmolarity and tear index of refraction are linearly related. Saline osmolarity is quite linear with respect to the angular movement of a SPR line, with the linearity shown to be in range off 5.0 mOsm/L to ±1 mOsm/L and measurement precision in the range of ±4 $10^{-6}$ RIU. The data illustrating ±1.0 mOsm/L linearity for several precision saline solutions is shown in FIG. 17.

It should be noted that precisely fitting a line to a series of precision calibrated saline solutions is a much easier problem than is the problem of accurately and precisely determining the salinity (i.e. the index of refraction) of an unknown saline solution. The first case simply requires determination of the slope of the calibration curve. The second case requires determining both the slope and the y-intercept point. Without the aid of external reference solutions, this second case is extremely difficult to accomplish. External reference solutions are not practical, since contamination of the gold sensing surface of the SPR instrument is extremely likely to occur.

FIG. 13 provides data from which the RIU per pixel can be calculated $-\Delta n=1.35713-1.3288=0.02853$ RIU corresponds to 910 pixels, or $\Delta n$/pixel=$3.113\times10$-6 RIU/pixel. The slope of the osmolarity v. pixel count chart in FIG. 17 is 0.7257 pixel s/mOsm/L. Multiplying these two factors together yields a calibration constant of 1.0 mOsm/L=$2.25\times 10^{-5}$ RIU. Typically, the engineering rule of thumb is that calibration accuracy of any measurement should be about a factor of 10 better than the desired accuracy required within a single measurement. Thus the absolute calibration accuracy required to accurately measure 1.0 mOsm/L tear osmolarity requires a calibration accuracy of the SPR device to +$2.25\times10^{0.6}$ RIU. Note that this is higher calibration accuracy than has been demonstrated by the reproducibility data in FIG. 13 as obtained under controlled laboratory conditions. This implies that reliable tear osmolarity measurements with an accuracy of ±1.0 mOsm/L may be difficult to obtain in routine practice.

Figure 21:
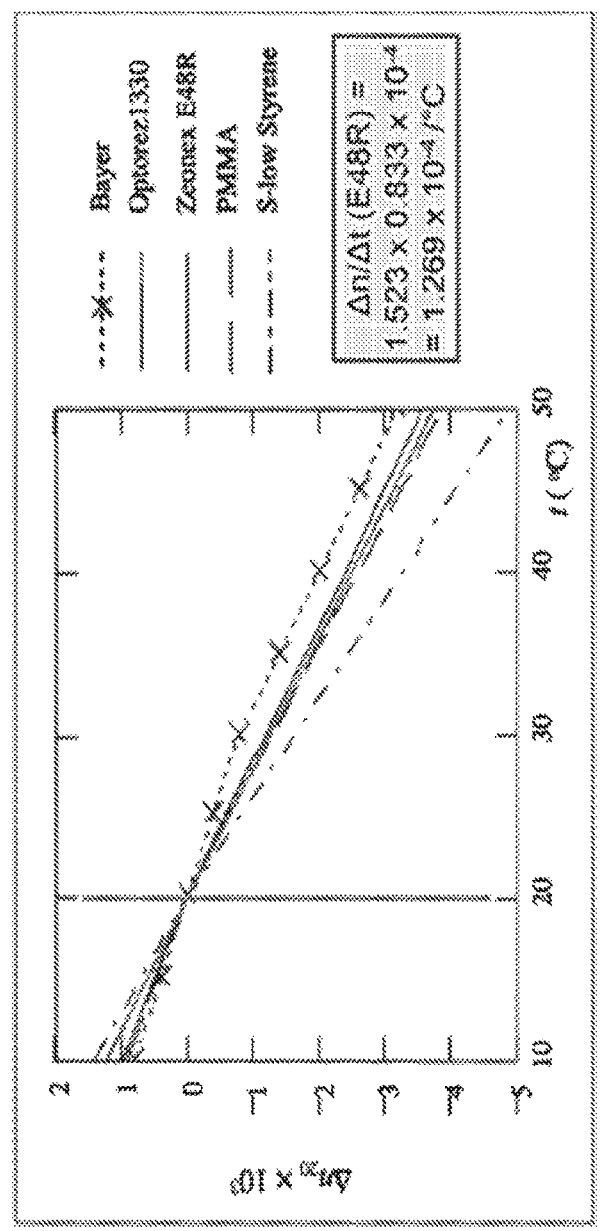
FIG. 21 is a graph showing the relative change of the index of refraction with temperature for a variety of example materials.

FIG. 21 illustrates the relative change of the index of refraction with temperature (i.e., $\Delta n/\Delta t$) for several common optical plastics. Note that ZEONEX® E48R ("E48R"), a low birefringence optical plastic manufactured by Zeon Corporation (Japan), with an index of refraction of 1.523 in the near infrared, is an optical polymer well suited for molding optical SPR prisms. Note that E48R has a $\Delta n/\Delta t$ that is approximately $1.269\times10^{-4}$ RIU/° C. and is similar to that of the other optical plastics illustrated in FIG. 21. As a consequence, the change in the index of refraction of ZEONEX® E48R per degree centigrade is approximately 28 times (i.e. $1.269\times10^{-4} \div 4.50\times10^{-6}$) greater than the resolution required to accurately and repeatably measure osmolarity to ±1.0 mOsm/L. In practice, this implies that the temperature of the E48R SPR prism would have to be either maintained within, or measured to an accuracy of about 0.036° C. Either of these conditions is impractical to achieve in an ordinary clinical office environment. Consequently, an extremely precise means of temperature calibration is required in order to achieve the desired accuracy of the tear osmolarity measurement.

Example 5: Self-Calibrating Sensor Concept 1

A basic self-calibrating SPR sensor concept evolved from the illustrations in FIG. 22 and FIG. 23. FIG. 22 depicts a single piece injection molded sensor formed in an optical grade plastic. This one piece sensor concept was intended to utilize kinematic mounting features to constrain it in six degrees of freedom to assure each and every sensor was precisely and repeatably aligned to the optical chassis of the system. As shown in FIG. 23, the concept envisioned a sensor comprised of three segments—a base portion provides the precision kinematic mechanical interface to the optical chassis, an SPR prism portion with a gold (or protected silver) coated SPR sensing surface for measuring tear osmolarity, and finally, a "skirt" portion to provide the transition between the SPR prism portion and the base portion. The prism portion provides for self-calibration by implementing means for obtaining both an optical critical angle transition and an air SPR line, preferably at two separate wavelengths of approximately 850 nm and 950 nm, as well as another separate SPR line that was to appear when the gold coated sensor surface of the SPR prism was wetted by the tear fluid.

FIG. 24 illustrates a concept of an SPR sensor that uses ellipsoidal surfaces to image light from an LED source onto the sensing surface. As shown in FIG. 25, in order to be able to produce both an air SPR line and a tear (or water) SPR line, there must be light incident on the sensing surface at about 42.0° to produce the air SPR line and at approximately 64.4° to produce a tear SPR line. This is achieved by imaging light from a point source LED using an elliptical surface to relay an image of the LED onto the sensing surface (e.g., a gold coated sensing surface) of the transparent elliptically shaped reflector. The angles of incidence of the LED light on the internal elliptically shaped surface are such that total internal reflectance occurs for the LED light. Light reflected by the gold coated SPR sensing surface is then reflected back toward the point source LED by the left hand elliptically shaped inner surface and is intercepted by a beamsplitter that reflects returning light to an image sensor that detects the location of the SPR line. For the case of a rotationally symmetric ellipsoidal sensor, the SPR line is actually an SPR circle centered on the rotational axis of the ellipsoidal surface Following the analysis of the elliptical sensor, a series of prismatic cap configurations were developed and analyzed using ZEMAX® optical design software. These various configurations are illustrated in FIG. 26 and FIG. 27. Generally, each of these concepts utilizes two internal transmitting facets on the inside of the cap and either 3 or 5 external facets that served to totally internally reflect light along the inside of the prism portion of the cap. These sensor concepts were able to provide images of the critical angle between air and E48R (ZEONEX® E48R material having a refractive index of approximately 1.5305), an air SPR line, and a tear SPR line. In one sensor concept, the critical angle and air SPR line are both captured in one image frame, and the tear SPR line is captured in a subsequent image frame. In another sensor concept, all three lines are captured in a single image frame.

Example 6: Analysis of Self-Calibrating Sensor

FIG. 28 contains a set of layout sketches for a sensor based on output from the ZEMAX® optical design software. FIG. 28, Panel C, depicts a close-up view of the sensor tip as comprised of two refracting facets (denoted by circled red numbers 1 and 7) that are disposed on an internal surface of the sensor, four external facets that are uncoated and reflect light via total internal reflection (denoted as surfaces 2, 3, 5 and 6) and a fifth surface partially coated with a gold stripe which is the SPR surface (denoted as surface 5 or the sensing surface). The gold coated portion of surface 5 provides the SPR line for both air and the tear osmolarity SPR measurements and the uncoated portion of surface 5 provides the Air critical angle transition. Both the air critical angle transition and the air SPR line must be obtained prior to surface 5 becoming wet by tear fluid.

The sketch in the upper left of FIG. 28 depicts the entire optical layout of the sensor and system. Four LEDs serve as the optical sources, two operable at nominally 855 nm and two operable at nominally 950 nm. Both sets of LEDs are comprised of an 855 nm LED and a 950 nm LED, each of which can be independently actuated. The two beams from the first set of 855 nm and 950 nm LEDs are combined into a single beam via a small dichroic beamsplitter (not shown) so as to propagate along a common beam path as illustrated by the upper ray bundles originating from the first set of LEDs. Considering first the case in which the 855 nm LED in the first set is actuated, the beam depicted as the upper bundle of rays is directed through a window and cylinder lens and then through refracting facet 7 toward facet 6. At facet 6 the light beam is reflected by total internal reflection toward facet 4, the sensor surface. The design of the cylinder lens is such that the light beam is nominally focused to a line on facet 4. The mid-point of the cone angle of the light incident on the sensor surface is nominally 42 degrees, which allows acquisition of both the air critical angle transition and the air SPR minima in a single image frame. At the sensor surface, the light beam depicted by the upper (light grey) ray bundle interacts with the gold and the air contacting the gold to form an air SPR line and an air critical angle transition for the wavelength of 855 nm.

After the light beam interacts at the sensing surface the light grey ray bundle light beam is reflected from facet 4 toward facet 2 at which point it is totally internally reflected toward and through refracting facet 1 and proceeds to impinge on the 2D CMOS imaging array. In the depicted embodiment, the imaging array is a grayscale version of the APTINA® MT9P031 1/2.5-Inch 5 Mp CMOS Digital Image Sensor comprised of 2592×1944 active pixels. The imager converts incident light into a digital electronic signal comprised of the digital data representing the intensity of the light at each of the 2592×1944 active pixels in the imaging array. These data can then be processed using the derivative signal processing techniques described above to find the exact location of the air critical angle transition and the air SPR minima angle.

Once the air critical angle transition and the air SPR minima angle are detected on the imaging array, the 855 nm LED is deactivated and the 950 nm LED is activated and a similar process is followed to acquire a set of air critical angle transition and air SPR minima angle at the 950 nm wavelength. The combination of these data comprise the automatic air calibration sequence that occurs each time the system is brought out of its "sleep" mode.

In a similar manner, light from the second set of 855 nm and 950 nm LED are combined and propagated through the system along the path illustrated by the dark gray bundle of rays shown in FIG. 28. The primary difference between the first set of LEDs and the second set is that light from the second set of LEDs is totally internally reflected by facet 5 on the way to impinging on the sensor facet and is totally internally reflected by facet 3 on its way to the imager. The effect of this difference is that the mid-point of the cone of light from the second set of LEDs is incident on the sensor surface at a nominal angle of approximately 64.4°. This nominal angle of incidence enables generation of SPR data for liquids such as water and tear fluid. As is the case for the first set of LEDs it is possible to obtain SPR data at 855 nm and 950 nm by simply alternating the actuation of the 855 nm and 950 nm LEDs.

Figure 29:
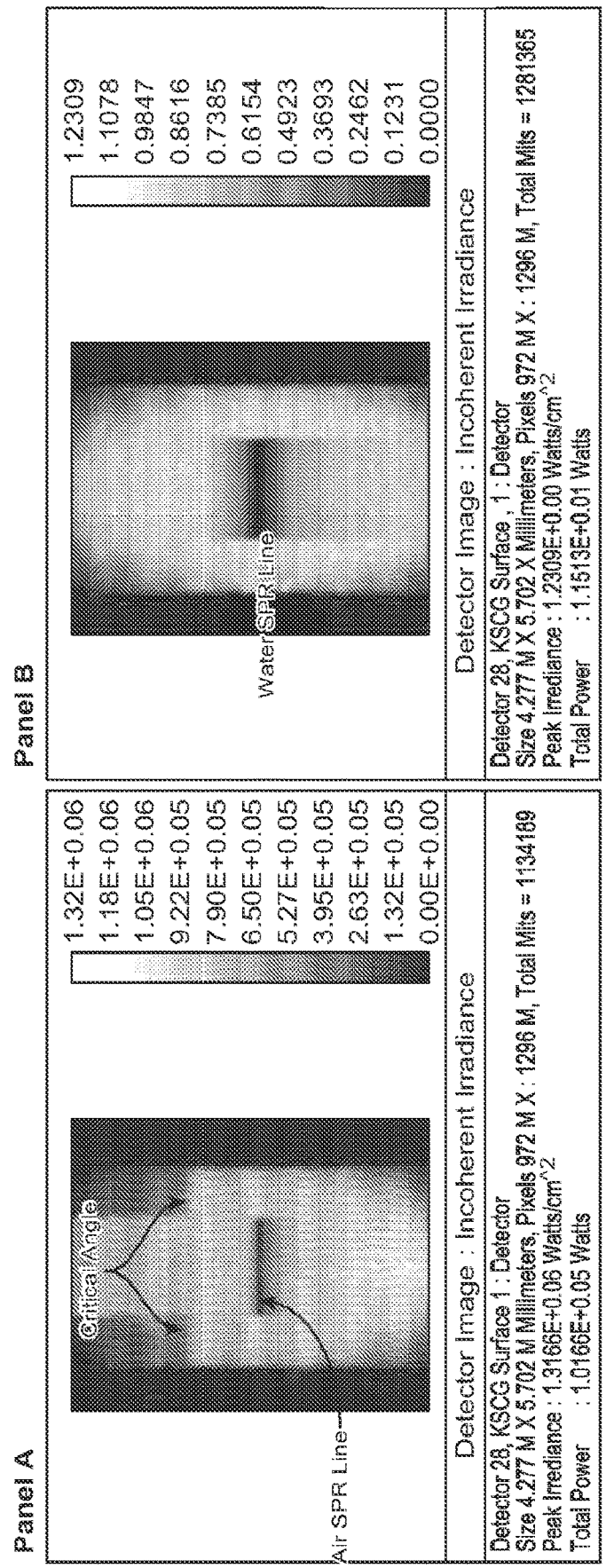
FIG. 29, Panel A shows a simulation of an air SPR line (obtained from a coated region of the sensing surface) and the critical angle transition (obtained from a non-coated region of the sensing surface) using one LED from a first set of LEDs from a dry sensing surface (in contact with air). Panel B illustrates an SPR line obtained using one LED from a second set of LEDs when the sensing surface has been contacted with water or tear fluid.

FIG. 29, Panel A illustrates the ZEMAX® simulation of the air SPR line and the critical angle transition using one LED from the first set of LEDs and before surface 5 is wet with water (or tear fluid). FIG. 29, Panel B illustrates the SPR line obtained using one of the LEDs from the second set under the condition that surface 5 has been wet with water (or tear fluid).

Example 7: Snell's Law and Critical Angle Transition

Figure 30:
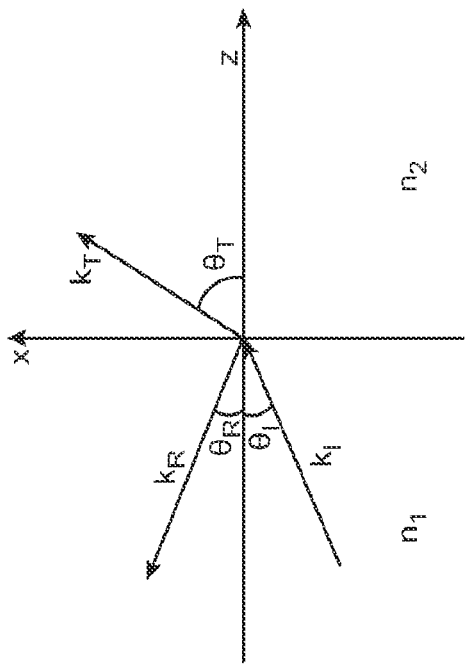
FIG. 30 illustrates the geometry of Snell's Law (the law of refraction) and the critical angle of a substrate.

Acquisition of accurate and precise critical angle data is an important aspect of the calibration of the subject sensors and systems. FIG. 30 illustrates the geometry of Snell's Law (the law of refraction) and the critical angle. FIG. 30 shows the simple case of Snell's Law and the critical angle for a single interface. A more involved optical thin film analysis shows that as long as the incident media has an index of $n_1$ and the emergent media has an index of $n_2$, then the critical angle is always given by $\theta_C = \text{Sin}-1(n_2/n_1)$, independent of the number of plane parallel layers between the incident media and the emergent media. Thus the critical angle is invariant with respect to the materials between the incident media and the emergent media—it is solely dependent on the values of $n_1$ and $n_2$. As a consequence, measurement of the location of the critical angle provides an important calibration factor for SPR measurements.

Figure 31:
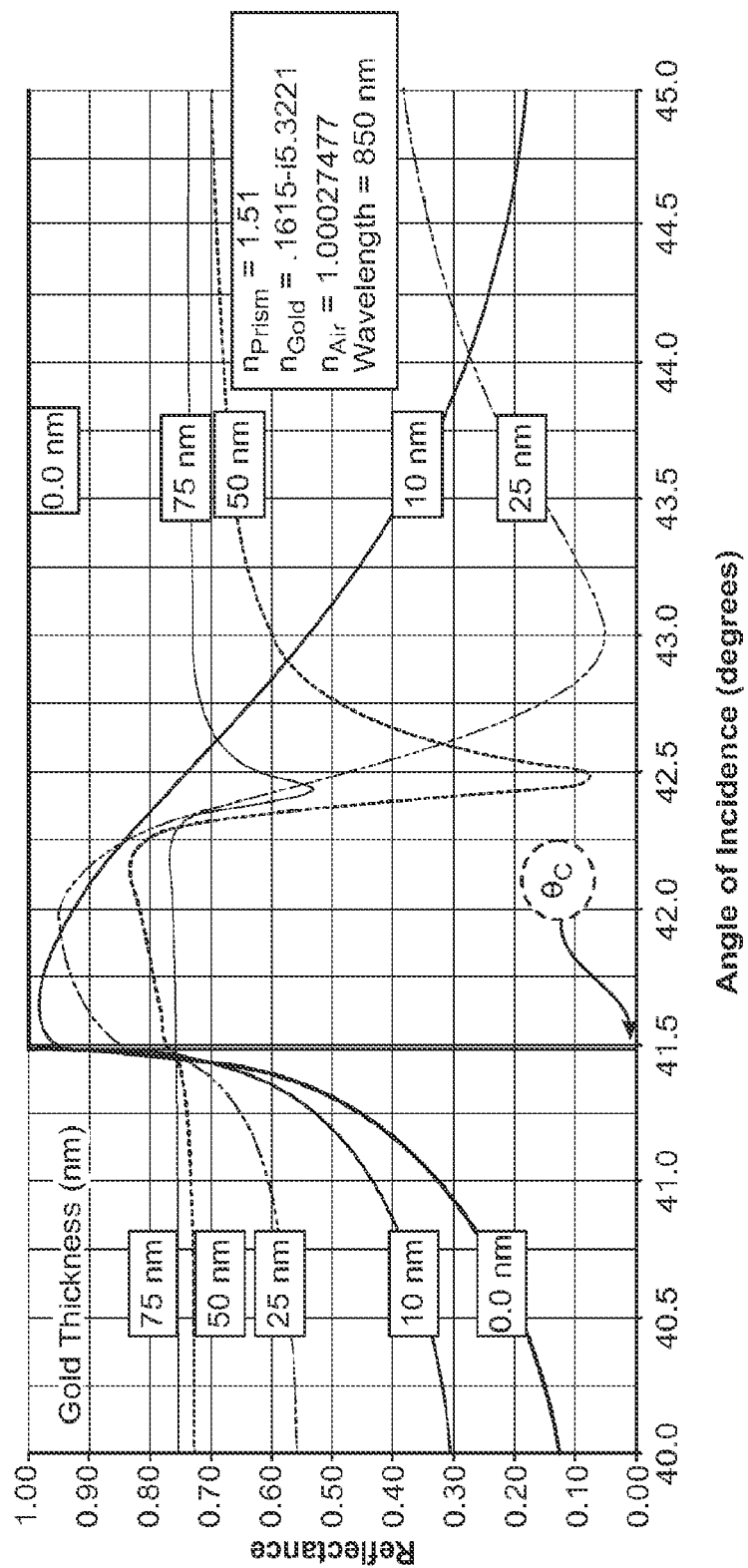
FIG. 31 is a graph of reflectance as a function of angle of incidence for a plurality of sensing surfaces having different thicknesses of gold film. The critical angle ($\theta_c$) remains constant, and is independent of the thickness of the gold film.

FIG. 31 illustrates the location of the critical angle for a gold layer on an incident medium with an index of refraction of 1.51. The emergent medium is air with an index of refraction of 1.00027477. The gold thickness is varied from zero thickness to a thickness of 75 nm. As shown in the chart of reflectance versus angle of incidence, the critical angle remains stationary at 41.4757° throughout this range of gold thickness. Since air is only weakly dispersive with respect to wavelength and temperature (and its index is well characterized for both wavelength and temperature) the primary contributor to the shift of the critical angle will be the index of refraction of the incident media—in the case of the subject systems, this is the index of refraction of the sensor, and any mechanical mounting tolerances of the sensor to the optical chassis. Consequently, by making critical angle measurements at 855 nm and 950 nm, and given the known and well characterized wavelength and thermal dispersion of the ZEONEX® E48R sensor material, it is possible to set up two equations and two unknowns to characterize the mounting angle of the sensor and the index of refraction of the E48R at the time of measurement.

Example 8: Self-Calibrating Sensor Concept 2

FIG. 32 depicts the optical layout of sensor concept 2. This concept is considerably simpler than sensor concept 1, utilizing two LEDs, one at 855 nm and a second at 950 nm, combined into a single beam using a beamsplitter (not illustrated), a single collimating lens, a single cylinder lens that doubles as the window for the optical chassis, a sensor comprised of two internal facets and three external facets, and an image detector. Light from either the 855 nm LED or the 950 nm LED follow essentially the same optical path. In operation, light from the active 855 nm LED is collimated by the collimating lens and then focused by the cylindrical lens into a line on the sensor facet 3. After passing through the cylindrical lens, the beam is refracted by facet 5 across the central axis of the sensor and is reflected by the uncoated facet 2. The angle of incidence of the beam on facet 2 is approximately 42.0°, so that an air critical angle transition will be produced at this surface. The reflected beam from facet 2 is incident on the gold coated sensor facet 3 at an angle of incidence of approximately 64.4° so as to produce an SPR minimum for either water or tear fluid near the central angle of the focused cone of light. The thickness of the gold on facets 3 and 4 is approximately 45 to 50 nm. After reflecting from the sensor surface 3, the beam is incident on gold coated facet 4 and an angle of incidence of approximately 42°, so as to produce an air SPR minimum upon reflection from this fourth facet. Finally the beam exits the sensor by refraction through facet 1, is realigned parallel to the optical axis of the system by passing through the cylindrical lens, and is subsequently incident on the 2593× 1944 pixel APTINA® imager described previously.

In a similar manner, SPR and critical angle data can be collected at the 950 nm wavelength by deactivating the 855 nm LED and activating the 950 nm LED. The path taken by the 950 nm light is virtually identical in this case.

Figure 33:
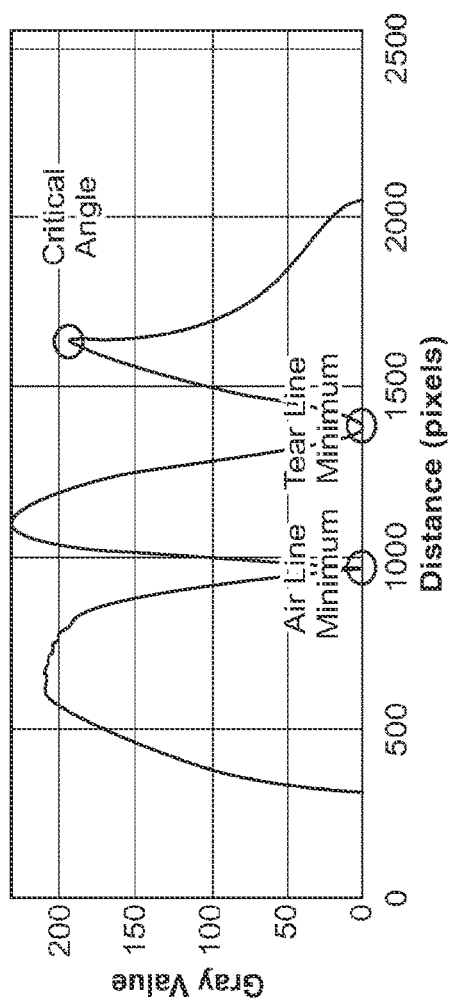
FIG. 33, Panel A is a simulated image showing data from a tear fluid sample. The air SPR line and tear SPR line are shown, as well as the critical angle line. Panel B is a graph showing gray-scale value as a function of pixel position for the image in Panel A. The minimum gray-scale value corresponding to the air and tear SPR lines are shown, as well as the maximum gray-scale value corresponding to the critical angle line.
Figure 33:
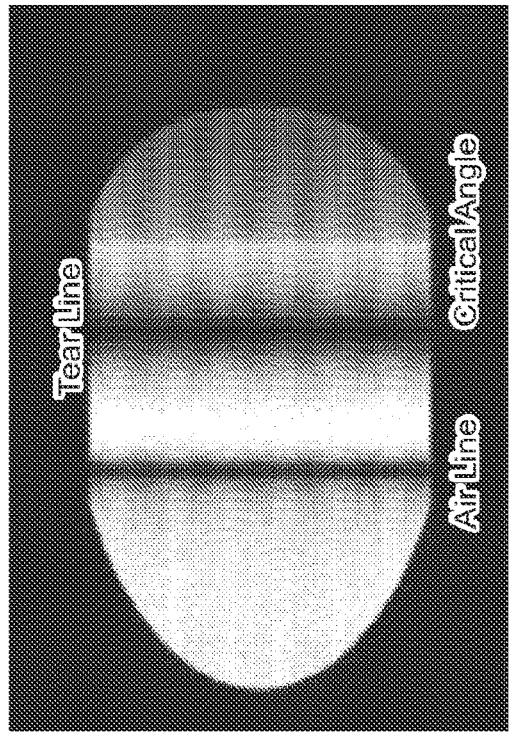

FIG. 33 illustrates a ZEMAX® simulation of the performance of sensor concept 2, depicting its potential to produce an air critical angle transition, a tear SPR line and an air SPR line in a single image. In principle, sensor concept 2 can generate a full set of air critical angle transition, tear SPR minima and air SPR minima data within a single captured frame, as depicted in FIG. 33.

Example 9: Analysis of Self-Calibrating Sensor Concept 1

FIG. 34 shows a further developed illustration of sensor concept 1. FIG. 34 illustrates the physical size of both the LEDs and the imager as offered mounted on a circuit board with support chips by XIMEA®. It should be noted that in comparison to the optical layout in FIG. 28, the layout in FIG. 34 has been inverted top to bottom for the purpose of providing a more direct line of sight over the top of the system to the tip of the sensor so that the physician taking the osmolarity measurement can more readily place the sensing surface of the sensor onto the tear film of the eye.

Referring still to FIG. 34, light from an LED that is emitted in the general direction of the sensor is collimated by the collimating lens and is focused by a cylinder lens and enters the internal hollow portion of the sensor. Inside the sensor, the light focused by the cylinder lens is refracted by the top inner facet of the sensor and is subsequently internally reflected by three of the five external facets of the sensor. The second of the three facets is the sensing surface at which the cylindrically focused light comes to focus and interacts with the sensing surface gold coating and the media in contact with the external surface of the gold. The internal reflection by the surface following the sensor surface, and the subsequent refraction by the lower inner facet primarily serve to direct the light exiting the sensor in the general direction of the image sensor. An optical wedge, which may be omitted, serves to direct the axis of the exiting beam closer to the physical axis of the system so as to lower its vertical profile.

FIG. 35 illustrates in more detail the structure for mounting the sensor on the machined aluminum optical chassis that supports the LEDs, optical components and the imager in their proper locations for creating and imaging the SPR lines and the critical angle transitions. FIG. 36 illustrates the length dimension of the optical chassis and FIG. 37 and FIG. 38 illustrate the chassis vertical dimensions, and also provide component call-outs and more detail regarding the mounting components that couple the sensor to the optical chassis.

FIG. 39 illustrates the configuration of the optical chassis when surface mount LEDs are used. This layout also depicts a cylinder lens bonded to a plane parallel disk of optical glass which serves as a window to prevent contaminants from entering the chain of optical components housed in the optical chassis. Bonding the cylinder lens to the window serves to permanently set its alignment with respect to the other optical components in the chassis. FIG. 39 also shows the location of a polarizer and its barrel. The polarizer is used to form the SPR and critical angle transition images on the image sensor. Finally the position of the beamsplitter that combines the light from the various LEDs in the system is illustrated. FIG. 40 is a similar illustration of the chassis in a perspective view.

FIG. 41 portrays the optical and sensor chassis mounted in its exterior housing and also indicates the location of a control board that is used to detect switch closures and activate the LEDs in the optical chassis in the appropriate sequence.

FIGS. 42-47 provide more detailed illustrations of the sensor. FIG. 42 and FIG. 43 illustrate the three retention components that are located 120° apart and upon which are three small protrusions that serve to engage a first inner surface of the bayonet mounting feature of the optical chassis. These flexures and protrusions bias the sensor so that the three kinematic mount points depicted in FIG. 44 are forced into contact with a second inner surface of the bayonet mounting feature in a kinematic fashion. FIG. 45 shows an exterior end view of a sensor in accordance with embodiments of the invention. In this illustration, the retention components no longer have a slot, which was found (using a mold flow analysis software application) to cause difficulty in completely filling the tabs during the injection molding process. FIG. 46 illustrates an exterior end view of a sensor in its mating bayonet feature of the optical chassis. FIG. 47 is a simulation of the appearance of a sensor as it would appear when molded in ZEONEX® E48R optical polymer. The sensing surface and a plurality of facets are identified.

Example 10: Benchtop Sensor System

FIG. 48 is an illustration of a desktop, or benchtop, system. As shown in FIG. 48, the benchtop system comprises two LED collimators, in this example one operational at a nominal wavelength of 855 nm and the other at 950 nm. The LED collimators are comprised of a point source LED, followed by a circular sheet polarizer and then an appropriate collimating lens. The depicted components are housed in brass housings. Note that the wavelengths of the collimators need not be 855 nm and 950 nm, but can be any pair of wavelengths that are appropriate for the sensor and the test media being analyzed.

As shown in FIG. 48, light from the 855 nm LED collimator is incident on the reflective hypotenuse of a 90° prism and is reflected toward the beamsplitter. At the beamsplitter, a portion of the 855 nm beam is transmitted through the beamsplitter and subsequently through a cylinder lens and into the SPR hemi-cylinder shaped sensor and is ultimately focused onto the gold coated external sensing surface of a gold coated microscope slide that has been index matched to the hemi-cylinder. The angle of incidence of this 855 nm beam on the surface of the gold is in the range of the critical angle at 855 nm so that an 855 nm air critical angle transition and an air SPR line can be generated. In a similar manner, a portion of the beam from the 950 nm LED collimator can be reflected by the beamsplitter, focused by the cylinder lens, enter the hemi-cylinder and impinge on the gold coated sensing surface, also at an angle in the range of the critical angle at 950 nm so that a 950 nm air critical angle transition and air SPR line can be generated.

In a similar fashion, the 855 nm beam that is reflected by the beamsplitter and the 950 nm beam transmitted through the beamsplitter are combined, reflect from a second reflective hypotenuse of a 90° prism, pass through a second cylinder lens, enter the hemi-cylinder and are incident on the gold coated microscope slide at angles in the range of the SPR minimum and thus generate 855 nm and 950 nm SPR lines for fluids such as water solutions, tear fluids, etc.

Light reflected from the gold coated microscope slide passes through and exits the hemi-cylinder in the general direction toward the image detector and is analyzed by a desktop or laptop computer generally using the signal processing techniques described above.

FIG. 49 is a perspective view of a benchtop system without component labels, and FIG. 50 is a perspective view with component labels. It should be noted that the optical chassis of the depicted benchtop system is formed by computer numerical control (CNC) machining its internal and external features from a solid billet of aluminum. This provides an extremely stable and precise optical chassis, and all critical components that require precise alignment are mounted via kinematic mounting features machined into the chassis. Consequently, there is no need for adjustable optical mounts or other similar adjustments in order to align the optical system. FIG. 51 is a photo of the one piece optical chassis and its one piece CNC machined cover.

Example 11: Determination of Osmolarity of a Tear Fluid

A sensor comprising a sensing surface with a gold film was used to determine the osmolarity of a tear fluid. The sensor was connected to a system, and the sensing surface was contacted with air as a reference medium. An optical signal having a wavelength of 855 nm was directed to interact with the sensing surface at an incident angle of approximately 42 degrees. The SPR signal from the sensing surface was detected using a detection component (FIG. 52, Panel A), and the pixel position corresponding to the minimum value of the SPR signal in air was determined (FIG. 52, Panel B).

Next, a sample of tear fluid was obtained from Ursa BioScience (Abingdon, Md.) and a small volume of the sample was placed in contact with a sensing surface of the sensor. An optical signal having a wavelength of 855 nm was directed at the sensing surface at an incident angle of approximately 64 degrees. When the tear fluid was placed in contact with the sensing surface, an instantaneous change in the pixel position corresponding to the minimum value of the SPR signal was detected (FIG. 52, Panel D), relative to the pixel position corresponding to the minimum value of the SPR signal in air. The tear fluid was left in contact with the sensing surface for 600 seconds, and data was collected over this time interval. The pixel position corresponding to the minimum value of the SPR signal changed over time, eventually reaching a plateau value. FIG. 52, Panel E, shows a graph of the SPR delta pixel value, measured using an optical signal having a wavelength of 855 nm, and over a time interval of 60 seconds following contact of the sensing surface with the tear fluid. The graph in FIG. 52, Panel E has y-axis units of pixels and x-axis units of seconds. Each data point in the depicted graph was obtained by subtracting the pixel position corresponding to the minimum value of the SPR signal at t=0 from the pixel position corresponding to the minimum value of the SPR signal at each subsequent time point. A mathematical function was generated from the plotted data points depicted in FIG. 52, Panel E, and the function was then analyzed to determine the osmolarity of the tear fluid by comparison to a calibration data set.

Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

The invention claimed is:

1. A system comprising:
 (i) a sensor comprising a sensing surface, wherein the sensor is configured to:
  direct a first optical signal to interact with the sensing surface over a first range of incident angles; and
  direct a second optical signal to interact with the sensing surface over a second range of incident angles,
  wherein the first range of incident angles is different from the second range of incident angles; and
 (ii) an optical chassis comprising:
  an optical signal generating component;
  a detection component;
  a processor;
  a controller; and
  a non-transitory computer readable medium comprising instructions that, when executed by the processor, cause the controller to:
   direct an optical signal having a wavelength to interact with the sensing surface over the first range of incident angles to generate a first surface plasmon resonance (SPR) signal;
   generate an image of the first SPR signal using the detection component;
   determine a pixel position of a minimum value of the first SPR signal on the generated image;
   direct an optical signal having the wavelength to interact with the sensing surface over the second range of incident angles to generate a second SPR signal;
   generate a series of images of the second SPR signal over a time interval using the detection component;
   determine a series of pixel positions that correspond to a minimum value of the second SPR signal over the time interval; and
   compare the pixel position of the minimum value of the first SPR signal and the series of pixel positions that correspond to the minimum value of the second SPR signal over the time interval to a calibration data set.

2. The system according to claim 1, wherein the non-transitory computer readable medium further comprises instructions that, when executed by the processor, cause the controller to compare a pixel position that corresponds to a minimum value of at least one of the SPR signals to a reference feature.

3. The system of claim 2, wherein the reference feature comprises a pixel position of a maximum value of a critical angle signal.

4. The system according to claim 3, wherein the sensing surface comprises a coated region and a non-coated region, and wherein the critical angle signal is generated from the non-coated region.

5. The system of claim 1, wherein the reference feature comprises a pixel position of an opto-mechanical reference (OMR).

6. The system according to claim 1, wherein the first range of incident angles spans 40 to 45 degrees.

7. The system according to claim 1, wherein the sensor is configured to direct the first optical signal to interact with the sensing surface at a first incident angle of 42 degrees.

8. The system according to claim 1, wherein the second range of incident angles spans 62 to 67 degrees.

9. The system according to claim 1, wherein the sensor is configured to direct the second optical signal to interact with the sensing surface at a second incident angle of 64 degrees.

10. The system according to claim 1, wherein the wavelength is selected from the group consisting of: 855 nm and 950 nm.

11. The system according to claim 1, wherein the sensor is configured to be removably coupled to the optical chassis.

12. A method for determining the osmolarity of a sample, the method comprising:
 contacting a sensing surface of a system according to claim 1 with a reference medium;
 directing an optical signal having a wavelength to interact with the sensing surface over the first range of incident angles to generate a first surface plasmon resonance (SPR) signal;
 generating an image of the first SPR signal using the detection component;
 determining a pixel position of a minimum value of the first SPR signal on the generated image;
 contacting the sensing surface with a test medium;

directing an optical signal having the wavelength to interact with the sensing surface over the second range of incident angles to generate a second SPR signal;

generating a series of images of the second SPR signal over a time interval using the detection component;

determining a series of pixel positions that correspond to a minimum value of the second SPR signal over the time interval; and comparing the pixel position of the minimum value of the first SPR signal and the series of pixel positions that correspond to the minimum value of the second SPR signal over the time interval to a calibration data set.

13. The method according to claim 12, further comprising comparing a pixel position that corresponds to a minimum value of at least one of the SPR signals to a reference feature.

14. The method of claim 13, wherein the reference feature comprises a pixel position of a maximum value of a critical angle signal.

15. The method of claim 13, wherein the reference feature comprises a pixel position of an opto-mechanical reference (OMR).

16. The method according to claim 12, wherein the wavelength is selected from the group consisting of: 855 nm and 950 nm.

17. The method according to claim 12, wherein the reference medium is air.

18. The method according to claim 12, wherein the sample is a biological sample.

19. The method according to claim 18, wherein the biological sample is a tear fluid.

20. The method according to claim 12, wherein the time interval ranges from 0.001 seconds to 90 seconds.

* * * * *